(12) United States Patent
Lowe, Jr. et al.

(10) Patent No.: US 11,007,520 B2
(45) Date of Patent: May 18, 2021

(54) COVALENTLY MODIFIED SURFACES, KITS, AND METHODS OF PREPARATION AND USE

(71) Applicant: Berkeley Lights, Inc., Emeryville, CA (US)

(72) Inventors: Randall D. Lowe, Jr., Emeryville, CA (US); Alexander J. Mastroianni, Alameda, CA (US); Mark P. White, Orinda, CA (US); Gregory G. Lavieu, Vitry sur Seine (FR); Kristin G. Beaumont, New York, NY (US)

(73) Assignee: Berkeley Lights, Inc., Emeryville, CA (US)

( * ) Notice: Subject to any disclaimer, the term of this patent is extended or adjusted under 35 U.S.C. 154(b) by 251 days.

(21) Appl. No.: 16/196,649

(22) Filed: Nov. 20, 2018

(65) Prior Publication Data

US 2019/0275516 A1 Sep. 12, 2019

Related U.S. Application Data

(63) Continuation of application No. PCT/US2017/034832, filed on May 26, 2017.
(Continued)

(51) Int. Cl.
*B01L 3/00* (2006.01)
*C12M 3/06* (2006.01)
(Continued)

(52) U.S. Cl.
CPC ... *B01L 3/502707* (2013.01); *B01L 3/502715* (2013.01); *B01L 3/502761* (2013.01);
(Continued)

(58) Field of Classification Search
CPC ..... B01L 2300/0636; B01L 2300/0816; B01L 2300/0864; B01L 2300/088;
(Continued)

(56) References Cited

U.S. PATENT DOCUMENTS

| 5,814,200 A | 9/1998 | Pethig et al. |
| 6,294,063 B1 | 9/2001 | Becker et al. |

(Continued)

FOREIGN PATENT DOCUMENTS

| CN | 101275114 A | 10/2008 |
| CN | 101592627 A | 12/2009 |

(Continued)

OTHER PUBLICATIONS

Chen et al., "Regioselective Patterning of Multiple SAMs and Applications in Surface-Guided Smart Microfluidics," ACS Appl. Mater. Interfaces, 2014, 6(24):21961-21969.
(Continued)

*Primary Examiner* — Jennifer Wecker
(74) *Attorney, Agent, or Firm* — McNeill Baur PLLC

(57) ABSTRACT

In biosciences and related fields, it can be useful to modify surfaces of apparatuses, devices, and materials that contact biomaterials such as biomolecules and biological microobjects. Described herein are surface modifying and surface functionalizing reagents, preparation thereof, and methods for modifying surfaces to provide improved or altered performance with biomaterials.

38 Claims, 14 Drawing Sheets

Related U.S. Application Data

(60) Provisional application No. 62/342,131, filed on May 26, 2016, provisional application No. 62/345,603, filed on Jun. 3, 2016, provisional application No. 62/353,938, filed on Jun. 23, 2016, provisional application No. 62/411,191, filed on Oct. 21, 2016, provisional application No. 62/410,238, filed on Oct. 19, 2016.

(51) Int. Cl.
  *B81C 1/00* (2006.01)
  *G01N 33/543* (2006.01)

(52) U.S. Cl.
  CPC ......... *B81C 1/00206* (2013.01); *C12M 23/16* (2013.01); *G01N 33/54393* (2013.01); *B01L 2300/0636* (2013.01); *B01L 2300/088* (2013.01); *B01L 2300/0816* (2013.01); *B01L 2300/0864* (2013.01); *B81B 2201/058* (2013.01)

(58) Field of Classification Search
  CPC ......... B01L 3/502707; B01L 3/502715; B01L 3/502761; B81B 2201/058; B81C 1/00206; C12M 23/16; G01N 33/54393
  See application file for complete search history.

(56) References Cited

U.S. PATENT DOCUMENTS

| | | |
|---|---|---|
| 6,379,929 B1 | 4/2002 | Burns et al. |
| 6,565,727 B1 | 5/2003 | Shenderov |
| 6,773,566 B2 | 8/2004 | Shenderov |
| 6,815,664 B2 | 11/2004 | Wang et al. |
| 6,911,132 B2 | 6/2005 | Pamula et al. |
| 6,942,776 B2 | 9/2005 | Medoro |
| 6,958,132 B2 | 10/2005 | Chiou et al. |
| 6,977,033 B2 | 12/2005 | Becker et al. |
| 7,090,759 B1 | 8/2006 | Seul |
| 7,163,612 B2 | 1/2007 | Sterling et al. |
| 7,252,928 B1 | 8/2007 | Hafeman et al. |
| 7,314,708 B1 | 1/2008 | Heller et al. |
| 7,328,979 B2 | 2/2008 | Decre et al. |
| 7,547,380 B2 | 6/2009 | Velev |
| 7,699,969 B2 | 4/2010 | Manaresi et al. |
| 7,790,631 B2 | 9/2010 | Sharma et al. |
| 7,956,339 B2 | 6/2011 | Ohta et al. |
| 8,037,903 B2 | 10/2011 | Wang et al. |
| 8,093,064 B2 | 1/2012 | Shah et al. |
| 8,228,657 B2 | 7/2012 | Jones et al. |
| 8,349,276 B2 | 1/2013 | Pamula et al. |
| 8,350,243 B2 | 1/2013 | Lee et al. |
| 8,529,743 B2 | 9/2013 | Kim et al. |
| 8,531,082 B2 | 9/2013 | Lee et al. |
| 8,581,167 B2 | 11/2013 | Lean et al. |
| 8,679,843 B2 | 3/2014 | Faris et al. |
| 8,685,344 B2 | 4/2014 | Sudarsan et al. |
| 8,864,972 B2 | 10/2014 | Yamakawa et al. |
| 8,921,041 B2 | 12/2014 | Wang et al. |
| 9,068,281 B2 | 6/2015 | Wu et al. |
| 9,134,513 B2 | 9/2015 | Chen et al. |
| 9,144,806 B2 | 9/2015 | Chen et al. |
| 9,201,042 B2 | 12/2015 | Bhattacharya et al. |
| 9,403,172 B2 | 8/2016 | Short et al. |
| 9,744,533 B2 | 8/2017 | Breinlinger et al. |
| 10,723,988 B2 | 7/2020 | Lowe, Jr. et al. |
| 10,799,865 B2 | 10/2020 | Lowe, Jr. et al. |
| 2003/0008364 A1 | 1/2003 | Wang et al. |
| 2003/0047456 A1 | 3/2003 | Medoro |
| 2003/0175947 A1 | 9/2003 | Liu et al. |
| 2003/0198968 A1 | 10/2003 | Matson |
| 2003/0224528 A1 | 12/2003 | Chiou et al. |
| 2004/0072278 A1 | 4/2004 | Chou et al. |
| 2004/0191789 A1 | 9/2004 | Manaresi et al. |
| 2004/0197905 A1 | 10/2004 | Hafeman |
| 2004/0229349 A1 | 11/2004 | Daridon |
| 2004/0231987 A1 | 11/2004 | Sterling et al. |
| 2005/0089993 A1 | 4/2005 | Boccazzi et al. |
| 2005/0112548 A1 | 5/2005 | Segawa et al. |
| 2005/0129581 A1 | 6/2005 | McBride et al. |
| 2005/0164402 A1 | 7/2005 | Belisle et al. |
| 2005/0175981 A1 | 8/2005 | Voldman et al. |
| 2005/0221333 A1 | 10/2005 | Sundararajan et al. |
| 2005/0264351 A1 | 12/2005 | Armit |
| 2005/0274456 A1* | 12/2005 | Roitman ............... B32B 37/00 156/292 |
| 2005/0274612 A1 | 12/2005 | Segawa et al. |
| 2006/0091015 A1 | 5/2006 | Lau |
| 2006/0091755 A1 | 5/2006 | Carlisle |
| 2006/0097155 A1 | 5/2006 | Adachi et al. |
| 2006/0154361 A1 | 7/2006 | Wikswo et al. |
| 2006/0165565 A1 | 7/2006 | Ermakov |
| 2006/0175192 A1 | 8/2006 | Lin |
| 2006/0186048 A1 | 8/2006 | Tan |
| 2006/0226012 A1 | 10/2006 | Kanagasabapathi et al. |
| 2006/0240548 A1 | 10/2006 | Deutsch et al. |
| 2006/0263612 A1 | 11/2006 | Chen et al. |
| 2007/0023292 A1 | 2/2007 | Kim et al. |
| 2007/0095669 A1 | 5/2007 | Lau et al. |
| 2007/0138016 A1 | 6/2007 | Wang |
| 2007/0148763 A1 | 6/2007 | Huh et al. |
| 2007/0183934 A1 | 8/2007 | Diercks et al. |
| 2007/0242105 A1 | 10/2007 | Srinivasan et al. |
| 2007/0243634 A1 | 10/2007 | Pamula et al. |
| 2007/0264481 A1 | 11/2007 | DeSimone et al. |
| 2007/0292941 A1 | 12/2007 | Handique et al. |
| 2008/0003142 A1 | 1/2008 | Link et al. |
| 2008/0006535 A1 | 1/2008 | Paik et al. |
| 2008/0013092 A1 | 1/2008 | Maltezos et al. |
| 2008/0038810 A1 | 2/2008 | Pollack et al. |
| 2008/0124252 A1 | 5/2008 | Marchand et al. |
| 2008/0153134 A1 | 6/2008 | Wiyatno et al. |
| 2008/0223721 A1 | 9/2008 | Cohen et al. |
| 2008/0225378 A1 | 9/2008 | Weikert et al. |
| 2008/0257735 A1 | 10/2008 | Jeon et al. |
| 2008/0274513 A1 | 11/2008 | Shenderov et al. |
| 2008/0299539 A1 | 12/2008 | Lee et al. |
| 2008/0302732 A1 | 12/2008 | Soh et al. |
| 2008/0318203 A1 | 12/2008 | Tran et al. |
| 2009/0023608 A1 | 1/2009 | Hung et al. |
| 2009/0098541 A1 | 4/2009 | Southern et al. |
| 2009/0136912 A1 | 5/2009 | Kurokawa et al. |
| 2009/0170186 A1 | 7/2009 | Wu et al. |
| 2009/0192044 A1 | 7/2009 | Fouillet |
| 2010/0000366 A1 | 1/2010 | Nomura et al. |
| 2010/0000620 A1 | 1/2010 | Fouillet et al. |
| 2010/0003666 A1 | 1/2010 | Lee et al. |
| 2010/0009335 A1 | 1/2010 | Joseph et al. |
| 2010/0101960 A1 | 4/2010 | Ohta et al. |
| 2010/0181195 A1 | 7/2010 | Tello |
| 2010/0206731 A1 | 8/2010 | Lau et al. |
| 2010/0273681 A1 | 10/2010 | Cerrina et al. |
| 2011/0053151 A1 | 3/2011 | Hansen et al. |
| 2011/0053783 A1 | 3/2011 | Du et al. |
| 2011/0086377 A1 | 4/2011 | Thwar et al. |
| 2011/0095201 A1 | 4/2011 | Stolowitz |
| 2011/0108422 A1 | 5/2011 | Heller et al. |
| 2011/0117634 A1 | 5/2011 | Halamish et al. |
| 2011/0143964 A1 | 6/2011 | Zhou et al. |
| 2011/0186165 A1 | 8/2011 | Borenstein et al. |
| 2011/0220505 A1 | 9/2011 | Wang et al. |
| 2011/0262906 A1 | 10/2011 | Dimov et al. |
| 2011/0301058 A1 | 12/2011 | Cheng et al. |
| 2012/0009671 A1 | 1/2012 | Hansen et al. |
| 2012/0015347 A1 | 1/2012 | Singhal et al. |
| 2012/0024708 A1 | 2/2012 | Chiou et al. |
| 2012/0073740 A1 | 3/2012 | Hsieh |
| 2012/0118740 A1 | 5/2012 | Garcia et al. |
| 2012/0156675 A1 | 6/2012 | Lueerssen et al. |
| 2012/0208266 A1 | 8/2012 | Bookbinder et al. |
| 2012/0325665 A1 | 12/2012 | Chiou et al. |
| 2013/0026040 A1 | 1/2013 | Cheng et al. |
| 2013/0062205 A1 | 3/2013 | Hadwen et al. |

(56) References Cited

U.S. PATENT DOCUMENTS

| | | |
|---|---|---|
| 2013/0118901 A1 | 5/2013 | Pollack et al. |
| 2013/0118905 A1 | 5/2013 | Morimoto et al. |
| 2013/0146459 A1 | 6/2013 | Bazant et al. |
| 2013/0171546 A1 | 7/2013 | White et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0206597 A1 | 8/2013 | Wang et al. |
| 2013/0261021 A1 | 10/2013 | Bocchi et al. |
| 2013/0280485 A1 | 10/2013 | Coclite et al. |
| 2013/0288055 A1 | 10/2013 | Doshita et al. |
| 2013/0288065 A1 | 10/2013 | Chen et al. |
| 2013/0288254 A1 | 10/2013 | Pollack et al. |
| 2014/0016176 A1 | 1/2014 | Kodani et al. |
| 2014/0038279 A1 | 2/2014 | Ingber et al. |
| 2014/0057311 A1 | 2/2014 | Kamm et al. |
| 2014/0102900 A1 | 4/2014 | Akella et al. |
| 2014/0116881 A1 | 5/2014 | Chapman et al. |
| 2014/0124370 A1 | 5/2014 | Short et al. |
| 2014/0144518 A1 | 5/2014 | Bohringer et al. |
| 2014/0153079 A1 | 6/2014 | Hsieh |
| 2014/0154703 A1 | 6/2014 | Skelley et al. |
| 2014/0154791 A1 | 6/2014 | North et al. |
| 2014/0166484 A1 | 6/2014 | Chang et al. |
| 2014/0255976 A1 | 9/2014 | Chang et al. |
| 2014/0262783 A1 | 9/2014 | Chang et al. |
| 2014/0274771 A1 | 9/2014 | Elizazu et al. |
| 2014/0299472 A1 | 10/2014 | Chang et al. |
| 2014/0308688 A1 | 10/2014 | Grego et al. |
| 2014/0378339 A1 | 12/2014 | Lammertyn et al. |
| 2015/0018226 A1 | 1/2015 | Hansen et al. |
| 2015/0107995 A1 | 4/2015 | Sista et al. |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2015/0167043 A1 | 6/2015 | Goluch et al. |
| 2015/0306598 A1 | 10/2015 | Khandros et al. |
| 2015/0306599 A1 | 10/2015 | Khandros et al. |
| 2015/0352547 A1* | 12/2015 | Breinlinger .......... B01L 3/5027 435/395 |
| 2015/0377831 A1 | 12/2015 | Wheeler et al. |
| 2016/0067711 A1 | 3/2016 | Yoon et al. |
| 2016/0158748 A1 | 6/2016 | Wu et al. |
| 2016/0184821 A1 | 6/2016 | Hobbs et al. |
| 2016/0193604 A1 | 7/2016 | McFarland et al. |
| 2016/0199837 A1 | 7/2016 | Breinlinger et al. |
| 2016/0222224 A1 | 8/2016 | Haag et al. |
| 2016/0252495 A1 | 9/2016 | Ricicova et al. |
| 2016/0257918 A1 | 9/2016 | Chapman et al. |
| 2016/0312165 A1 | 10/2016 | Lowe, Jr. et al. |
| 2017/0021366 A1 | 1/2017 | Chapman et al. |
| 2017/0043343 A1 | 2/2017 | Khandros et al. |
| 2017/0173580 A1 | 6/2017 | Lowe, Jr. et al. |
| 2018/0099282 A1 | 4/2018 | Breinlinger et al. |
| 2018/0298318 A1 | 10/2018 | Kurz et al. |
| 2019/0240665 A1 | 8/2019 | Lionberger et al. |
| 2019/0275516 A1 | 9/2019 | Lowe, Jr. et al. |

FOREIGN PATENT DOCUMENTS

| | | |
|---|---|---|
| CN | 102296029 A | 12/2011 |
| EP | 1065378 A2 | 1/2001 |
| EP | 1065378 B1 | 4/2002 |
| EP | 2647434 B1 | 5/2017 |
| EP | 2570188 B1 | 8/2017 |
| JP | 2006220606 A | 8/2006 |
| KR | 20100008222 A | 1/2010 |
| KR | 20120066100 A | 6/2012 |
| TW | 550066 B | 9/2003 |
| WO | 2002088702 A2 | 11/2002 |
| WO | 2004012848 A2 | 2/2004 |
| WO | 2004089810 A2 | 10/2004 |
| WO | 2005095963 A2 | 10/2005 |
| WO | 2005114132 A2 | 12/2005 |
| WO | 2007008609 A2 | 1/2007 |
| WO | 2007024701 A2 | 3/2007 |
| WO | 2007120241 A2 | 10/2007 |
| WO | WO 2008/057366 | 5/2008 |
| WO | 2008119066 A1 | 10/2008 |
| WO | 2008131048 A2 | 10/2008 |
| WO | 2009046125 A2 | 4/2009 |
| WO | 2009130694 A2 | 10/2009 |
| WO | 2009146143 A2 | 12/2009 |
| WO | 2009149467 A2 | 12/2009 |
| WO | 2009151505 A1 | 12/2009 |
| WO | 2010040851 A2 | 4/2010 |
| WO | 2010115167 A2 | 10/2010 |
| WO | 2010147078 A1 | 12/2010 |
| WO | 2010147942 A1 | 12/2010 |
| WO | 2011160430 A1 | 12/2011 |
| WO | 2012024658 A2 | 2/2012 |
| WO | 2012037030 A2 | 3/2012 |
| WO | 2012024658 A3 | 5/2012 |
| WO | 2012072823 A1 | 6/2012 |
| WO | 2012162779 A1 | 12/2012 |
| WO | 2013019491 A1 | 2/2013 |
| WO | 2013106588 A1 | 7/2013 |
| WO | 2013130714 A1 | 9/2013 |
| WO | 2013148745 A1 | 10/2013 |
| WO | 2014036915 A1 | 3/2014 |
| WO | 2014070873 A1 | 5/2014 |
| WO | 2014081840 A1 | 5/2014 |
| WO | 2014167858 A1 | 10/2014 |
| WO | 2015036364 A1 | 3/2015 |
| WO | 2015092064 A1 | 6/2015 |
| WO | 2015164846 A1 | 10/2015 |
| WO | 2015164847 A1 | 10/2015 |
| WO | 2015188171 A1 | 12/2015 |
| WO | 2016090295 A1 | 6/2016 |
| WO | WO 2017/091601 | 6/2017 |

OTHER PUBLICATIONS

Extended European Search Report for European Patent Application No. 17803724.8, dated Feb. 26, 2020, 15 pages.

Mazurek et al., "Preparing mono-dispersed liquid core PDMS microcapsules from thiol-ene-epoxy-tailored flow-focusing microfluidic devices," RSC Advances, 2015, 5:15379-15386.

Written Opinion and Search Report in Singapore Patent Application No. 11201809539R, dated Mar. 31, 2020, 12 pages.

Yu et al., "Flow-Through Functionalized PDMS Microfluidic Channels with Dextran Derivative for ELISAs," Lab on a Chip, 2009, 9(9):1243-1247.

Zhang et al. "'Click' Chemistry-Based Surface Modification of poly(dimethylsiloxane) for Protein Separation in a Microfluidic Chip," Electrophoresis, 2010, 31(18): 3129-3136.

Bellis, S.L., Advantages of RGD peptides for directing cell association with. Biomaterials, Jun. 2011, vol. 32, No. 18, pp. 4205-4210.

Chiou et al., "Massively parallel manipulation of single cells and microparticles using optical images," Nature, vol. 436 (Jul. 21, 2005), pp. 370-372.

Chiou_Dissertation_UC Berkeley "Massively Parallel Optical Manipulation of Single Cells, Micro- and Nano-particles on Optoelectronic Devices" 2005.

Chow et al., "Peptide-based polymers in biomedicine and biotechnology" Materials Science and Engineering 62:125-155 (2008).

Chung et al., Imaging Single-Cell Signaling Dynamics with a Deterministic High-Density Single-Cell Trap Array, Anal. Chem. 83(18):7044-7052 (2011).

Dalvi et al., Molecular Origins of Fluorocarbon Hydrophobicity, Proceedings of the National Academy of Sciences, 107(31): 13603-7 (2010).

Dicarlo et al., "Dynamic Single Cell Analysis for Quantitative Biology," Analytical Chemistry (Dec. 1, 2006), pp. 7918-7925.

Drelich et al., "The Effect of Drop (Bubble) Size on Advancing and Receding Contact Angles for Heterogeneous and Rough Solid Surfaces as Observed with Sessile-Drop and Captive-Bubble Techniques" Journal of Colloid and Interface Science 179, 37-50 (1996), Article No. 0186.

(56) References Cited

OTHER PUBLICATIONS

Fan et al. Cross-scale electric manipulation of cells and droplet by frequency-modulated dielectrophoresis and electrowetting (Lab Chip, 8, 1325-1331) (Year: 2008).
Fuchs et al., "Electronic sorting and recovery of single live cells from microlitre sized samples" Lab on a Chip 6:121-26 (2006).
Furuta, Tsutomu et al., "Wetting mode transition of nanoliter scale water droplets during evaporation on superhydrophobic surfaces with random roughness structure" Applied Surface Science 258(7): pp. 2378-2383; Jan. 2012.
Furuta, Tsutomu et al., "Wetting Mode Transition of Water Droplets by Electrowetting on Highly Hydrophobic Surfaces Coated with Two Different Silanes", Chemistry Letters 41.1 (2011): 23-25.
Hsu, HY et al., "Sorting of Differentiated Neurons Using Phototransistor-Based Optoelectronic Tweezers for Cell Replacement Therapy of Neurodegenerative Diseases", Transducers 2009, Denver, CO USA Jun. 2009, download dated Nov. 23, 2009 from IEEE Xplore, 4 pages.
Huang et al. Digital Microfluidic Dynamic Culture of Mammalian Embryos on an Electrowetting on Dielectric (EWOD) Chip, PLoS One 10(5):e0124196 (2015).
Huang et al., "Mirofluidic Integrated optoelectronic tweezers for single-cell preparation and analysis" Lab on a Chip, 13:3721-3727 (2013).
Huang et al., Continuous Perfusion Microfluidic Cell Culture Array for High-Throughput Cell-Based Assays, Biotech and Bioengineering 89(1): 1-8 (2004). Dec. 3, 2004.
Iliescu et al., Continuous Field-Flow Separation of Particle Populations in a Dielectrophoretic Chip with Three Dimensional Electrodes, Applied Physics Letters 90:234104 (2007).
Jones, "On the Relationship of Dielectrophoresis and Electrowetting", Langmuir 18:4437-4443 (2002).
Lagally et al., Parallel microfluidic arrays for SPRI detection, Proceedings of SPIE, vol. 7759, p. 77590J (2010).
Lee et al., Microfluidic Chemostat and Turbidostat with Flow Rate, Oxygen and Temperature Control for Dynamic Continuous Culture , Lab on a Chip 11:1730-39 (2011).
Lee, Gi-Hun et al. "Separation and sorting of cells in microsystems using physical principles", Journal of Micromechanics & Microengineering, Institute of Physics Publishing, Bristol, GB, vol. 26, No. 1, Dec. 16, 2015 (Dec. 16, 2015), p. 13003.
Lowe, "Controlled Vapor Deposition of Azide-terminated Siloxane Monolayers: a Platform for Tailoring Oxide Surfaces", Stanford University, Aug. 1, 2011.
Mehling et al., "Microfluidic Cell Culture" Current Opinion in Biotechnology Feb. 2014, 25:95-102.
Nevill et al., Integrated microfluidic cell culture and lysis on a chip, Lab on a Chip 7:1689-95 (2007).
Papageorgiou, D.P. et al. "Superior performance of multilayered fluoropolymer films in low voltage electrowetting" Journal of Colloid Interface Science, Oct. 25, 2011, vol. 368, No. 1, pp. 592-598.
Park, Sung-Yong et al., "Single-sided continuous optoelectrowetting (SCOEW) for droplet manipulation with light patterns" Lab on a Chip, vol. 10, No. 13, pp. 1655-1661, Jul. 7, 2010, published online May 6, 2010.
Pei et al., Light-Actuated Digital Microfluidics for Large-Scale, Parallel Manipulation of Arbitrarily Sized Droplets, 2010 IEEE 23rd Intl. Conf. on MEMS, pp. 252-255.
Ritchie et al., "Reconstitution of Membrane Proteins in Phospholipid Bilayer Nanodiscs" Methods Enzymol., 464:211-231 (2009), 23 pages.
Somaweera H. et al., Generation of a Chemical Gradient Across an Array of 256 Cell Cultures in a Single Chip. Analyst, Oct. 7, 2013, vol. 138, No. 19, pp. 5566-5571.
Srisuwan et al., "The Effects of Alkalized and Silanized Woven Sisal Fibers on Mechanical Properties of Natural Rubber Modified Epoxy Resin" Energy Procedia 56 (2014) 19-25.
Swain et al., "Advances in embryo culture platforms: novel approaches to improve preimplantation embryo development through modifications of the microenvironment," Human Reproduction Update 17(4):541-57 (Mar. 31, 2011).
Valley et al., "A unified platform for optoelectrowetting and optoelectronic tweezers", Lab on a Chip 11:1292-97, Feb. 22, 2011.
Valley et al., An Integrated Platform for Light-Induced Dielectro-Phoresis and Electrowetting, International Conference on Miniaturized Systems for Chemistry and Life Sciences (2010).
Valley et al., Optoelectronic Tweezers as a Tool for Parallel Single-Cell Manipulation and Simulation, IEEE Transactions on Biomedical Circuits and Systems, vol. 3, No. 6 (Dec. 2009), pp. 424-431.
WO2010147078, University of Tokyo, Machine Translation, Dec. 23, 2010, 12 pages.
Xu, Guoling et al,. Recent Trends in Dielectrophoresis, Informacije MIDEM, 2010, vol. 40, Issue No. 4, pp. 253-262.
Yi et al., "Microfluidics technology for manipulation and analysis of biological cells," Analytica Chimica Acta 560 (2006), pp. 1-23.
Young et al., Fundamentals of microfluidic cell culture in controlled microenvironments, Chem Soc Rev 39(3):1036-48 (2010).
Yu, L. et al. "Flow-through functionalized PDMS microfluidic channels with dextran derivative for ELISAs" Lab on a Chip, Jan. 20, 2009, vol. 9, No. 9, pp. 1243-1247.
Banuls et al., "Chemical Surface Modifications for the Development of Silicon-Based Label-Free Integrated Optical (IO) Biosensors: A Review," Analytica Chimica Acta., 2013, 777:1-16.
Zhang et al., "Azide Functional Monolayers Grafted to a Germanium Surface: Model Substrates for ATR-IR Studies of Interfacial Click Reactions," Langmuir, 2011, 28(1):abstract (2 pages).
International Search Report and Written Opinion from PCT/US2017/034832, dated Sep. 27, 2017, 20 pages.

\* cited by examiner

COVALENTLY MODIFIED SURFACES, KITS, AND METHODS OF PREPARATION AND USE

This application is a continuation of International Patent Application No. PCT/US2017/034832, filed May 26, 2017, which claims the benefit under 35 U.S.C. 119(e) of U.S. Provisional Application No. 62/342,131, filed on May 26, 2016; U.S. Provisional Application No. 62/345,603, filed on Jun. 3, 2016; 62/353,938, filed on Jun. 23, 2016; U.S. Provisional Application No. 62/411,191, filed on Oct. 21, 2016; and of U.S. Provisional Application No. 62/410,238, filed on Oct. 19, 2016, each of which disclosures is herein incorporated by reference in its entirety.

BACKGROUND OF THE INVENTION

In biosciences and related fields, it can be useful to modify surfaces of apparatuses, devices, and materials that contact biomaterials such as biomolecules and biological micro-objects. Some embodiments of the present invention include a siloxane reagent, preparation thereof, and methods for modifying surfaces to provide improved or altered performance with biomaterials.

SUMMARY OF THE INVENTION

In a first aspect, a microfluidic device is provided, where the microfluidic device includes an enclosure comprising a base, a cover, and microfluidic circuit material defining a fluidic circuit therein, where at least one inner surface of the base, the cover and the microfluidic circuit material has a first covalently bound surface modification including a first linking group, and a first moiety, wherein the first moiety is a first surface contact moiety or a first reactive moiety; where at least one inner surface of the base, the cover and the microfluidic circuit material has a second covalently bound surface modification including a second linking group, and a second moiety, where the second moiety is a second surface contact moiety or second reactive moiety, and where the first linking group and the second linking group are different from each other and/or the first moiety is different from the second moiety. In some embodiments, a common inner surface of the base, the cover and the microfluidic circuit material has the first covalently bound surface modification and the second covalently bound surface modification.

In another aspect, a method of forming a covalently modified surface on at least one inner surface of a microfluidic device including an enclosure having a base, a cover and microfluidic circuit material defining a fluidic circuit therein, the method including: contacting the at least one inner surface with a first modifying reagent and a second modifying reagent; reacting the first modifying reagent with a first nucleophilic moiety of the at least one inner surface; reacting the second modifying reagent with a second nucleophilic moiety of the at least one inner surface; and forming the at least one covalently modified surface including a first covalently bound surface modification including a first linking group and a first moiety that is a first surface contact moiety or a first reactive moiety; and a second covalently bound surface modification including a second linking group and a second moiety that is a second surface contact moiety or second reactive moiety, where the first linking group is different from the second linking group or the first moiety is different from the second moiety. In some embodiments, the first covalently bound surface modification and the second covalently bound surface modification may be formed on a common inner surface of the base, the cover and the microfluidic circuit material.

In another aspect, a method is provided for forming different covalently modified surfaces in a regioselective manner within a microfluidic device. The microfluidic device can include an enclosure having a base, a cover, and a microfluidic circuit material defining a microfluidic circuit therein, where the microfluidic circuit comprises a flow region and a sequestration pen, and where the sequestration pen comprises an isolation region and a connection region, the connection region comprising a proximal opening to the flow region and fluidically connecting the isolation region to the flow region. The method can include the steps of: flowing a first modifying reagent through the flow region under conditions such that the first modifying reagent does not enter the isolation region of the sequestration pen; reacting the first modifying reagent with nucleophilic moieties on at least one surface of the flow region, thereby forming a first modified surface within the flow region, wherein the first modified surface does not extend into the isolation region of the sequestration pen; flowing a second modifying reagent through the flow region under conditions such that the second modifying reagent enters into the isolation region of the sequestration pen; and reacting the second modifying reagent with nucleophilic moieties on at least one surface of the isolation region of the sequestration pen, thereby forming a second modified surface within the isolation region of the sequestration pen. Typically, the first modifying reagent does not have the same structure as the second modifying reagent.

In another aspect, a kit is provided, including a microfluidic device as described herein. The kit may further include a surface modifying reagent having a structure of Formula XII:

RP-L-surface contact moiety            Formula XII;

wherein RP is a reaction pair moiety; surface contact moiety is a moiety configured to support cell growth, viability, portability, or any combination thereof; L is a linker; wherein L may be a bond or 1 to 200 non-hydrogen atoms selected from any combination of silicon, carbon, nitrogen, oxygen, sulfur and phosphorus atoms, and may further include 0 or 1 coupling groups CG.

In another aspect, a compound having a structure of Formula XIII is provided:

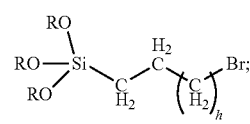

Formula XIII where h is an integer of 1 to 19 and R is selected independently from the group consisting of H and $C_1$-$C_6$ alkyl. In some embodiments, h is 5 to 19.

In yet another aspect, a method of synthesizing a compound having a structure of Formula XIII is provided:

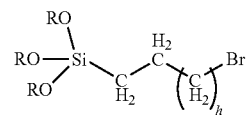

Formula XIII including reacting a compound having a structure of the following formula:

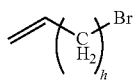

with a compound having a structure of the formula HSi(OR)$_3$, in the presence of a catalyst or an initiator, thereby producing the compound of Formula XIII, where h is an integer of 1 to 19 and each instance of R is independently H or C$_1$ to C$_6$ alkyl.

In a further aspect, a compound having a structure of Formula IV is provided:

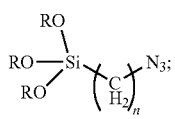

Formula IV where n is an integer of 3 to 21, and R is independently H or C$_1$ to C$_6$ alkyl. In some embodiments, n is 9, 14 or 16.

In another aspect, a method of synthesizing a compound of Formula IV is provided:

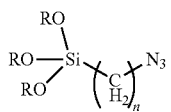

Formula IV including the step of reacting a compound having a structure of Formula XIII:

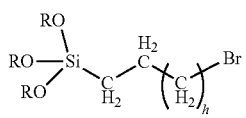

Formula XIII where h is 1 to 19 with azide ion, thereby producing the compound of Formula IV, where n is 3 to 21 and R is H or C$_1$-C$_6$ alkyl.

DETAILED DESCRIPTION OF THE INVENTION

Figure 1A:
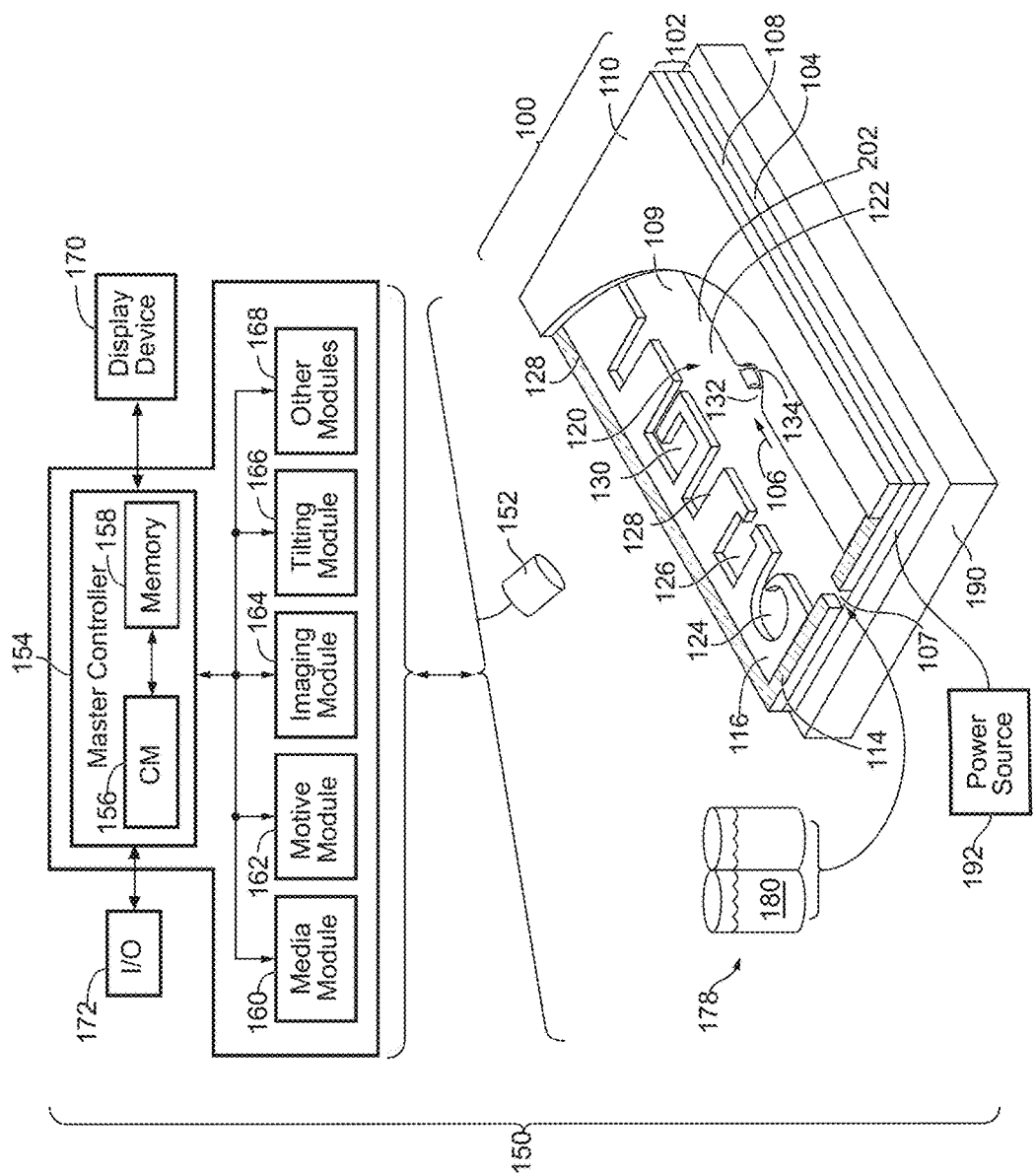
FIG. 1A illustrates an example of a system for use with a microfluidic device and associated control equipment according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axial/y-axial area.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one. As used herein, the term "plurality" can be 2, 3, 4, 5, 6, 7, 8, 9, 10, or more.

As used herein, "alkyl" refers to a straight or branched hydrocarbon chain radical consisting solely of carbon and hydrogen atoms, containing no unsaturation, having from one to six carbon atoms (e.g., $C_1$-$C_6$ alkyl). Whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated. In some embodiments, it is a $C_1$-$C_3$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), hexyl, and the like.

Unless stated otherwise specifically in the specification, an alkyl group may be optionally substituted by one or more substituents which independently are: aryl, arylalkyl, heteroaryl, heteroarylalkyl, hydroxy, halo, cyano, trifluoromethyl, trifluoromethoxy, nitro, trimethylsilanyl, —OR', —SR', —OC(O)—R', —N(R')$_2$, —C(O)R', —C(O)OR', —OC(O)N(R')$_2$, —C(O)N(R')$_2$, —N(R')C(O)OR', —N(R')C(O)R', —N(R')C(O)N(R')$_2$, N(R')C(NR')N(R')$_2$, —N(R')S(O)$_t$R'(where t is 1 or 2), —S(O)$_t$OR' (where t is 1 or 2), —S(O)$_t$N(R')$_2$ (where t is 1 or 2), or PO$_3$(R')$_2$ where each R' is independently hydrogen, alkyl, fluoroalkyl, aryl, aralkyl, heterocycloalkyl, or heteroaryl.

As referred to herein, a fluorinated alkyl moiety is an alkyl moiety having one or more hydrogens of the alkyl moiety replaced by a fluoro substituent. A perfluorinated alkyl moiety has all hydrogens attached to the alkyl moiety replaced by fluoro substituents.

As referred to herein, a "halo" moiety is a bromo, chloro, or fluoro moiety.

As referred to herein, an "olefinic" compound is an organic molecule which contains an "alkene" moiety. An alkene moiety refers to a group consisting of at least two carbon atoms and at least one carbon-carbon double bond. The non-alkene portion of the molecule may be any class of organic molecule, and in some embodiments, may include alkyl or fluorinated (including but not limited to perfluorinated) alkyl moieties, any of which may be further substituted.

As used herein, "air" refers to the composition of gases predominating in the atmosphere of the earth. The four most plentiful gases are nitrogen (typically present at a concentration of about 78% by volume, e.g., in a range from about 70-80%), oxygen (typically present at about 20.95% by volume at sea level, e.g. in a range from about 10% to about 25%), argon (typically present at about 1.0% by volume, e.g. in a range from about 0.1% to about 3%), and carbon dioxide (typically present at about 0.04%, e.g., in a range from about 0.01% to about 0.07%). Air may have other trace gases such as methane, nitrous oxide or ozone, trace pollutants and organic materials such as pollen, diesel particulates and the like. Air may include water vapor (typically present at about 0.25%, or may be present in a range from about 10 ppm to about 5% by volume). Air may be provided for use in culturing experiments as a filtered, controlled composition and may be conditioned as described herein.

As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A microfluidic device or a nanofluidic device may be referred to herein as a "microfluidic chip" or a "chip"; or "nanofluidic chip" or "chip".

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is about 100,000 microns to about 500,000 microns, including any value therebetween. In some embodiments, the horizontal dimension is about 100 microns to about 1000 microns (e.g., about 150 to about 500 microns) and the vertical dimension is about 25 microns to about 200 microns, (e.g., from about 40 to about 150 microns). It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding.

As used herein, the term "expanding" when referring to cells, refers to increasing in cell number.

As referred to herein, "gas permeable" means that the material or structure is permeable to at least one of oxygen, carbon dioxide, or nitrogen. In some embodiments, the gas permeable material or structure is permeable to more than one of oxygen, carbon dioxide and nitrogen and may further be permeable to all three of these gases.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, when averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "non-sweeping" rate of fluidic medium flow means a rate of flow sufficient to permit components of a second fluidic medium in an isolation region of the sequestration pen to diffuse into the first fluidic medium in the flow region and/or components of the first fluidic medium to diffuse into the second fluidic medium in the isolation region; and further wherein the first medium does not substantially flow into the isolation region.

Surface Modification.

Surfaces of materials, devices, and/or apparatuses for manipulation and storage of biomaterials may have native properties that are not optimized for short and/or long term contact with such material, which may include but is not limited to micro-objects (including but not limited to biological micro-objects such as biological cells), biomolecules, fragments of the biomolecules or biological micro-objects, and any combination thereof. It may be useful to modify one or more surfaces of a material, device or apparatus to decrease one or more undesired phenomena associated with a native surface in contact with one or more biomaterials. In other embodiments, it may be useful to enhance surface properties of the material, device, and/or apparatus to introduce a desired characteristic to the surface, thereby broadening the handling, manipulation or processing capabilities of the material, device, and/or apparatus. To that end, molecules which can modify a surface to either decrease undesired properties or introduce desirable properties are needed.

A microfluidic device is described herein having an enclosure including a base, a cover, and microfluidic circuit material defining a fluidic circuit therein, where at least one inner surface of the base, the cover and the microfluidic circuit material has a first covalently bound surface modification including a first linking group, and a first moiety, wherein the first moiety is a first surface contact moiety or a first reactive moiety; wherein at least one inner surface of the base, the cover and the microfluidic circuit material has a second covalently bound surface modification including a second linking group, and a second moiety, wherein the second moiety is a second surface contact moiety or second reactive moiety, and where the first linking group and the second linking group are different from each other or the first covalently bound moiety is different from the second covalently bound moiety. The first surface modification may be a covalently modified surface and the second surface modification may be a functionalized surface. In other embodiments, the first surface modification may be a first covalently modified surface and the second surface modification may be a second covalently modified surface having either a different linking group or different surface modifying ligand.

Modifying Reagent: Surface Modifying Compound.

In various embodiments, a surface modifying compound may include a surface modifying ligand which may be a non-polymeric moiety such as an alkyl moiety, a substituted alkyl moiety, such as a fluoroalkyl moiety (including but not limited to a perfluoroalkyl moiety) or an alkylene oxide moiety, amino acid moiety, alcohol moiety, amino moiety, carboxylic acid moiety, phosphonic acid moiety, sulfonic acid moiety, sulfamic acid moiety, or saccharide moiety covalently modifies the surface to which it is attached. The surface modifying compound also includes a connecting moiety, a group which covalently attaches the surface modifying ligand to the surface, as shown schematically in Equation 1. Depending on the composition of the surface, the connecting moiety may be a silicon containing moiety such as $-Si(T)_2W$, where W is -T, $-SH$, or $-NH_2$; and T is independently OH, $OC_{1-6}$alkyl, or halo, or a combination thereof; a phosphonic acid moiety or an activated form thereof, a maleimide moiety, a terminal olefin, or any suitable connecting moiety known in the art. The surface modifying ligand is attached to the covalently modified surface via a linking group LG, which is the product of the reaction of the connecting moiety with functional groups of the surface (including hydroxide, oxide, amine or sulfur). A linking group LG may include a siloxy, phosphonate, alkyl sulfide and the like. In some embodiments, the linking group LG may be a siloxy or phosphonate group.

Equation 1

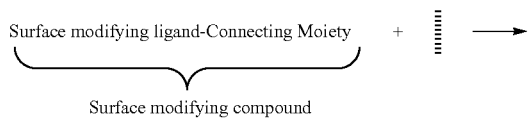

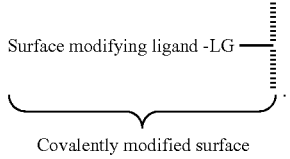

In some embodiments, the surface modifying compound has a structure of Formula XXXII:

V-L$_{sm}$-Surface modifying ligand    Formula XXXII;

wherein connecting moiety V is —P(O)(OH)$_2$ or —Si(T)$_2$W; W is -T, —SH, or —NH$_2$ and is the moiety configured to connect to the surface; each instance of T is independently OH, OC$_{1-6}$alkyl, or halo. L$_{sm}$ is a linker including 1 to 200 non-hydrogen atoms selected from any combination of silicon, carbon, nitrogen, oxygen, sulfur and phosphorus atoms and further includes 0, 1, 2, 3, or 4 coupling groups CG. The number of non-hydrogen atoms that form CG is not included in the size of L$_{sm}$, and is not limited by the size of L$_{sm}$. The surface modifying ligand may include 0, 1, 2, or 3 CG.

In some embodiments, the surface modifying compound of Formula XXXII may be a compound of Formula I:

V—(CH$_2$)$_n$-surface modifying ligand    Formula I;

wherein connecting moiety V is —P(O)(OH)Q- or —Si(T)$_2$W; W is -T, —SH, or —NH$_2$ and is the moiety configured to connect to the surface; Q is —OH and is the moiety configured to connect to the surface; and n is an integer of about 3-21. In some embodiments, n is an integer of about 7 to 21. Each instance of T is independently OH, OC$_{1-6}$alkyl, or halo, where alkyl includes but is not limited to methyl, ethyl, n-propyl, 2-propyl, n-butyl, and the like. In some embodiments, T is OH, OC$_{1-3}$alkyl or Cl. The surface modifying ligand may include 0, 1, 2, or 3 CG.

In some embodiments, the compound of Formula I is a compound having a structure of Formula II:

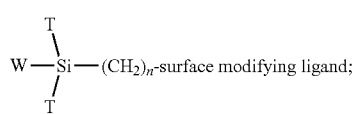

wherein W, T, and n are as defined above for Formula I. The surface modifying ligand may include 0, 1, 2, or 3 CG.

In other embodiments, the compound of Formula I is a compound of Formula III:

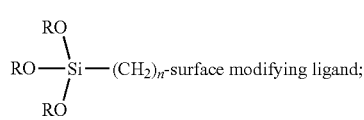

wherein R is C$_{1-6}$alkyl and n is an integer of 3-21. The surface modifying ligand may include 0, 1, 2, or 3 CG.

The surface modifying compound used to covalently modify a surface of the inner surface(s) of a microfluidic device, as described herein, introduces the surface modifying ligand having a surface contact moiety, which supports cell growth, viability or portability of biological cells. The surface modifying ligand including a surface contact moiety can include anionic, cationic, or zwitterionic moieties, or any combination thereof. Without intending to be limited by theory, by presenting cationic moieties, anionic moieties, and/or zwitterionic moieties at the inner surfaces of an enclosure of the microfluidic device, the surface modifying ligand of the covalently modified surface can form strong hydrogen bonds with water molecules such that the resulting water of hydration acts as a layer (or "shield") that separates the biological micro-objects from interactions with non-biological molecules (e.g., the silicon and/or silicon oxide of the substrate). In addition, in embodiments in which the covalently modified surface is used in conjunction with coating agents, the anions, cations, and/or zwitterions of the surface contact moiety of the surface modifying ligand can form ionic bonds with the charged portions of non-covalent coating agents (e.g. proteins in solution) that are present in a medium (e.g. a coating solution and/or a fluidic medium for supporting biological cells) in the enclosure. In other embodiments, the surface modifying ligand may include at least one amino acid, which may include more than one type of amino acid. Thus, the surface modifying ligand may include a peptide or a protein. In some embodiments, the surface modifying ligand may include an amino acid which may provide a zwitterionic surface to support cell growth, viability, portability, or any combination thereof.

In still other embodiments, the surface modifying ligand may present a hydrophilic surface contact moiety at its enclosure-facing terminus, including but not limited at least one alkylene oxide moiety. One useful class of alkylene ether containing polymers is polyethylene glycol (PEG M$_w$<100,000 Da). In some embodiments, a PEG may have an M$_w$ of about 100 Da, 300 Da, 500 Da, 1000 Da, or 5000 Da. In other embodiments, a hydrophilic surface modifying ligand may include one or more saccharides. The covalently linked saccharides may be mono-, di-, or polysaccharides. Like the charged moieties discussed above, the hydrophilic surface modifying ligand can form strong hydrogen bonds with water molecules such that the resulting water of hydration acts as a layer (or "shield") that separates the biological micro-objects from interactions with non-biological molecules (e.g., the silicon and/or silicon oxide of the substrate).

The surface modifying ligand may alternatively include one or more amino groups as a surface contact moiety. The amino group may be a substituted amine moiety, guanidine moiety, nitrogen-containing heterocyclic moiety or heteroaryl moiety. The amino containing moieties may have structures permitting pH modification of the environment within a microfluidic device. In some embodiments of the microfluidic device described herein, the environment may be modified within pens opening to a flow region (which may be the same as or may be different from sequestration pens, as described herein), and/or flow regions (which may include channels).

In various embodiments, a surface modifying compound may include a linear backbone of 8 to 26 atoms, wherein the atoms are carbon, oxygen, nitrogen or sulfur; and a connecting moiety selected from —P(O)(OH)$_2$ and —Si(Y)$_3$, where Y is Cl, OC$_{1-3}$ alkyl, or OH, and non-backbone substituents of carbon atoms of the linear backbone are hydrogen or fluorine. The surface modifying compound can attach to functional groups on the surface (including hydroxide, oxide, amine or sulfur) through the connecting moiety. A first end of the linear backbone is connected to the connecting moiety through a bond to the phosphorus or silicon of the connecting moiety and a second end of the linear backbone is distal to and not connected to the surface.

Independently for each carbon of the linear backbone, the non-backbone substituents are either all hydrogen or all fluorine. In some embodiments, the linear backbone may be all carbon atoms. A linear backbone having all carbon backbone atoms may have non-backbone substituents that are all hydrogen atoms.

In some embodiments, the linear backbone of the surface modifying compound may be part of a linker $L_{sm}$, as described above, and may include two carbon atoms disposed at the first end of the linear backbone (e.g., attached directly to the connecting moiety), and the non-backbone substituents for each of the two carbons may be hydrogen. In some embodiments, the linear backbone may include a sulfur atom. In some embodiments, the linear backbone may include two sulfur atoms, and the two sulfur atoms are disposed adjacent to each other. When two sulfur atoms disposed adjacent to each other are present in the linear backbone, then the two sulfur atoms are not disposed at the first end (e.g., neither of the two sulfur atoms are not directly connected to the connection moiety) or the second end of the linear backbone (e.g., located at the end of the modifying compound, distal to the connection to the surface). In some embodiments, a disulfide moiety of the linear backbone may be a cleavable motif, and may permit removal of part or all of the surface modifying ligand. Other cleavable motifs may be included in the linker $L_{sm}$ of the surface modifying compound, as described herein.

In some embodiments, the surface modifying compound may contain 0, 1, 2, 3 or 4 coupling groups CG as described herein. The surface modifying compound may have been formed from two or more portions coupled to each other to provide the linking group and the surface modifying ligand where the CG may be part of linker $L_{sm}$ or may be part of the surface modifying ligand (which also contains the surface contact moiety).

In some embodiments, the surface modifying compound may include carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the connecting moiety.

In other embodiments of the surface modifying compound, the linear backbone may include one or more oxygen atoms. Each of the one or more oxygen atoms may not be connected directly to another oxygen, sulfur or nitrogen, and may not be disposed at the first end of the linear backbone. In some embodiments, when the linear backbone includes one or more oxygen atoms, each of the one or more oxygen atoms may not be disposed at the second end of the linear backbone. In some embodiments, each of the one or more oxygen atoms may be disposed within the linear backbone such that at least two backbone atoms adjacent to each oxygen atom proximal to the first end of the linear backbone are carbon atoms comprising hydrogen non-backbone substituents and at least two backbone atoms adjacent to each oxygen atom distal to the first end of the linear backbone are carbons comprising hydrogen substituents.

A covalently bonded modification may be introduced to the surface upon reaction with the compound of Formula XXXII to provide a surface having a structure of Formula XXXI:

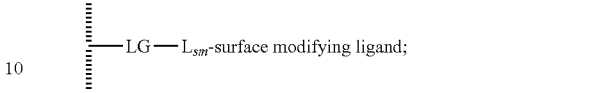

Formula XXXI where LG is —W—Si(OZ)$_2$O— or —OP(O)$_2$O—; W is O, S, or N, Z is a bond to an adjacent silicon atom or is a bond to the surface; $L_{sm}$ is a linker comprising 1 to 200 non-hydrogen atoms selected from any combination of silicon, carbon, nitrogen, oxygen, sulfur and phosphorus atoms and further comprises 0, 1, 2, 3, or 4 coupling groups CG; and ≡ is the surface. In some embodiments, n is an integer of 7 to 21.

In some embodiments, the covalently bonded modification may have a structure of Formula VIII:

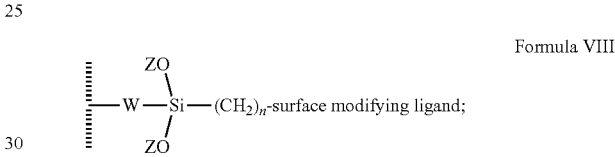

Formula VIII where W is O, S, or N; Z is a bond to an adjacent silicon atom or is a bond to the surface; n is an integer of 3-21; and ≡ is the surface. In some embodiments, W is O. In various embodiments, n is an integer of 7 to 21. The surface modifying ligand may include 0, 1, 2, or 3 CG.

In other embodiments, the covalently bonded modification has a structure of Formula IX:

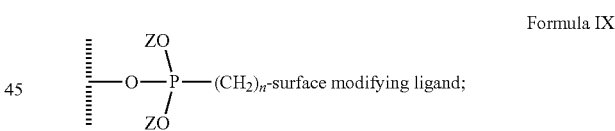

Formula IX where n, and ≡ are each defined as above. Z is a bond to an adjacent phosphorus atom or is a bond to the surface. The surface modifying ligand may include 0, 1, 2, or 3 CG.

In some embodiments, the surface modifying ligand may have a structure of Formula X:

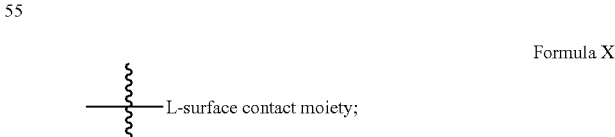

Formula X where L is a linker; and surface contact moiety is a moiety that provides improved contact characteristics for biological micro-objects, as described herein.

In other embodiments, the surface modifying ligand of the modified surface may have a structure of Formula X:

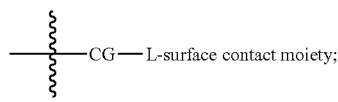

Formula XI where L is a linker; and surface contact moiety is a moiety that provides improved contact characteristics for biological micro-objects.

Linker L may be a bond or may include 1 to 200 non-hydrogen atoms selected from any combination of silicon, carbon, nitrogen, oxygen, sulfur and phosphorus atoms, subject to chemical bonding limitations as is known in the art. In some embodiments, linker L may include 1 to 200 non-hydrogen atoms selected from any combination of silicon, carbon, nitrogen, oxygen, sulfur and phosphorus atoms, subject to chemical bonding limitations as is known in the art. Linker L or the surface contact moiety may include 0, 1, or 3 coupling groups CG.

Coupling Group CG.

CG is a coupling group and may be any moiety such as but not limited to triazolylenyl, carboxamide, imide, ether, ester, keto, sulfonamide, sulfonate, cyclooctyl-fused diazine, alkene or aromatic moieties that may result from attaching the surface contact moiety to the remainder of the surface modifying reagent of Formula XXXII, or the surface modifying compound of Formula I, Formula II, or Formula III (e.g., formed as part of the synthesis of the surface modifying ligand).

In some other embodiments, CG is the moiety resultant from reaction of the reactive moiety of the functionalizing reagents of Formula XXXIII, Formula IV or Formula VI with a respective reaction pair moiety of a surface modifying reagent as described herein. For example, a functionalizing reagent having a azide reactive moiety may form a triazolylenyl CG moiety upon forming a covalently modified surface of Formula XXXI, Formula VIII, or Formula IX.

Coupling group CG may be a triazolylenyl moiety, which may be further substituted, and may have one or more additional ring systems fused with the triazolylenyl moiety. The additional fused ring system(s) may itself be further substituted with additional fused rings and may provide the attachment point to linker L-surface contact moiety. In some embodiments, the triazolylenyl moiety is fused with a cyclooctynyl ring system, which may be further substituted either with additional fused rings, including but not limited to dibenzocylcooctynyl, or other substitutions such as fluorine (difluorinated cyclooctyne (DIFO)).

CG may in some embodiments be a noncovalent binding pair. For example, the noncovalent binding of biotin with streptavidin provides a very stable binding pair and may be a CG. Further, since streptavidin has four binding sites, two portions of a surface modifying ligand, surface modifying reagent, or functionalized surface may be joined by the sequence of biotin/streptavidin/biotin. For example, a functionalized surface has a biotin reactive moiety, streptavidin is then introduced to bind to the biotin reactive moiety, and finally where a second biotinylated moiety (such as biotin-fibronectin) is introduced and bound to another of the binding sites on streptavidin. The product is a covalently bound surface modification having a surface contact moiety of fibronectin and the sequence of biotin/streptavidin/biotin is considered to be a single coupling group CG. The streptavidin is performing the role of linking two similarly functionalized portions together.

Surface Contact Moiety.

The surface contact moiety of the surface modifying ligand may be any surface contact moiety as described herein and in other portions of the disclosure and may include non-polymeric or polymeric moieties. The surface contact moiety may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acid; or amino acids. The alkyl or perfluoroalkyl moieties may have a backbone chain length of greater than 10 carbons. In other embodiments, the surface contact moiety may include saccharide moieties, and may be dextran. In other embodiments, the surface contact moiety may include alkylene ether moieties. The alkylene ether moieties may be polyethylene glycol.

In various embodiments, the surface contact moiety may of the surface modifying ligand include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the surface contact moiety may include polymeric moieties, which may be any of the moieties described above.

In some embodiments, the surface contact moiety may comprise carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

Cleavable Moiety.

The surface modifying ligand may further include a cleavable moiety, which may be located within the linker $L_{sm}$ of the surface modifying compound, linker L of the surface modifying ligand or may be part of the surface contact moiety of the surface modifying compound or surface modifying reagent. In some embodiments, a cleavable moiety may be included within linker $L_m$ of the functionalized surface of Formula XXX, Formula V, or Formula VII. The cleavable moiety may be configured to permit disruption of the covalently modified surface. In some embodiments, disruption may be useful to promote portability of the one or more biological cells after a period of culturing. The cleavable moiety may be a photocleavable moiety such as nitro-substituted benzyl esters (e.g., Broad-Pharm Catalog #BP-22675); a UV cleavable moiety such as a substituted 1,2-diphenyl ethyl ketoester moiety (e.g., a benzil derivation such as BroadPharm Catalog #BP 22689); or may be a moiety which can be cleaved under specific chemical conditions. For example, a disulfide linkage can be cleaved under conditions (e.g., reducing conditions such as dithiothreitol) that may not interfere with the growth or viability of the biological cells on the covalently modified surface. Other useful cleavable moieties that may be incorporated within surface modifying ligands or functionalized surfaces can include a vicinal diol moiety, which is cleavable by sodium periodate. The sodium periodate cleavage is another non-cytotoxic cleavage reagent. Diazo moieties, which are cleavable by dithionite, may also be a useful cleavable moiety. Additionally, a 5, 5, dimethyl-exo-cyclohexen-yl-1,3, dione moiety may be a useful cleavable moiety for use in the surface modifying ligand or functionalized surface of Formula XXX, Formula V, or Formula VII, and may be cleaved by hydrazine solution.

Modifying Reagent: Surface Functionalizing Reagent.

A surface may be covalently modified by a functionalizing reagent, to introduce a functionalized surface modification to one or more surfaces of the microfluidic device.

A functionalizing reagent is a compound of Formula XXXIII:

Formula XXXIII;

wherein V is —P(O)(OH)$_2$ or —Si(T)$_2$W; W is -T, —SH, or —NH$_2$ and is the moiety configured to connect to the surface; T is independently OH, OC$_{1-6}$alkyl, or halo; L$_{fm}$ is a linker comprising 1 to 200 non-hydrogen atoms selected from any combination of silicon, carbon, nitrogen, oxygen, sulfur and phosphorus atoms and further comprises 0, 1 or 2 coupling groups CG; and R$_x$ is a reactive moiety.

Reactive Moiety.

The reactive moiety may be any of an alkyne moiety, azide moiety, amine moiety, carboxylic acid moiety, biotin moiety, streptavidin moiety, olefin moiety, trans cyclooctene moiety, s-tetrazine moiety, thiol moiety, maleimide moiety, halide moiety, cyano moiety, isocyanate moiety, epoxide moiety, hydroxyamine moiety, a masked hydroxyl such as acetate and the like, or sulfonyl fluoride moiety. This list of reactive moieties is not limiting and any suitable reactive moiety may be selected for use with an appropriate reaction pair moiety. While most reactive moieties react with a respective reaction pair moiety to form a covalently coupled CG, the high binding affinity between biotin and streptavidin permits its use as a reactive moiety/reaction pair moiety.

The functionalized surface formed by the reaction of functionalizing reagent XXXIII has a structure of Formula XXX:

Formula XXX where LG is —W—Si(OZ)$_2$O— or —OP(O)$_2$O—; W is O, S, or N, Z is a bond to an adjacent silicon atom or is a bond to the surface, and L$_{fm}$ and R$_x$ are as defined for Formula XXXIII.

In some embodiments, a functionalizing reagent of Formula XXXIII may be a compound of Formula IV:

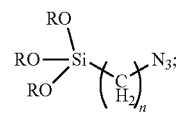

Formula IV wherein R is OC$_{1-6}$alkyl and n is an integer of 3-21. Azide is the reactive moiety R$_x$. In some embodiments of the compound of Formula IV, n may be an integer of 7 to 21. For the compound of Formula IV, each instance of R may be independently chosen from H or C$_1$-C$_6$ alkyl, where alkyl includes but not limited to methyl, ethyl, n-propyl, 2-propyl, n-butyl and the like. In some embodiments, R may be C$_1$-C$_3$ alkyl. In some embodiments, R may be methyl or ethyl. In various embodiments, each of the three instances of R is methyl or each of the three instances of R is ethyl. In other embodiments, n may be 9, 14, or 16. In yet other embodiments, n may be 9.

The functionalized surface formed by the reaction of the surface with the surface functionalizing reagent of Formula IV may have a structure of Formula V:

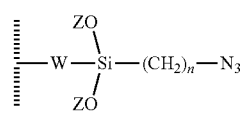

Formula V wherein W is O, S, or N, Z is a bond to an adjacent silicon atom of another surface functionalizing ligand (—WSi(OZ)$_2$(CH$_2$)$_n$—N$_3$) also bound to the surface or is a bond to the surface, n is an integer of 3-21, and ≡ is the surface. In some embodiments, n may be an integer of about 7 to 21. In some embodiments, W may be O. In various embodiments, each instance of R may be independently chosen from H or C$_1$-C$_6$ alkyl, where alkyl includes but not limited to methyl, ethyl, n-propyl, 2-propyl, n-butyl and the like. In some embodiments, R may be C$_1$-C$_3$ alkyl. In some embodiments, R may be methyl or ethyl. In various embodiments, each of the three instances of R is methyl or each of the three instances of R is ethyl. In other embodiments, n may be an integer of 7 to 21. In some embodiments, n may be an integer of 9 to 21, 10 to 21, 11 to 21, 12 to 21, 13 to 21, 14 to 21, 15 to 21, 16 to 21, 17 to 21, or 18 to 21. In yet other embodiments, n may be an integer of 10 to 18, 12 to 18, 13 to 18, or 14 to 18. In other embodiments, n may be 9, 14, or 16. In yet other embodiments, n may be 9.

In other embodiments, a surface functionalizing reagent of Formula XXXIII may be a compound of Formula VI:

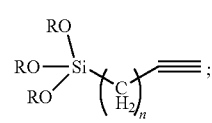

Formula VI wherein n is an integer of 3 to 21 and each instance of R is independently H or C$_1$-C$_6$ alkyl. Alkyne is the reactive moiety R$_x$ of Formula VI. In some embodiments, n may be an integer of about 7 to 21. In various embodiments, each instance of R may be independently chosen from H or C$_1$-C$_6$ alkyl, where alkyl includes but not limited to methyl, ethyl, n-propyl, 2-propyl, n-butyl and the like. In some embodiments, R may be $C_1$-$C_3$ alkyl. In some embodiments, R may be methyl or ethyl. In various embodiments, each of the three instances of R is methyl or each of the three instances of R is ethyl. In some embodiments, n may be an integer of 9 to 21, 10 to 21, 11 to 21, 12 to 21, 13 to 21, 14 to 21, 15 to 21, 16 to 21, 17 to 21, or 18 to 21. In yet other embodiments, n may be an integer of 10 to 18, 12 to 18, 13 to 18, or 14 to 18. In other embodiments, n may be 9, 14, or 16. In yet other embodiments, n may be 9.

The compound of Formula VI may be covalently coupled to a surface via reaction of the siloxane moiety with nucleophilic groups of the surface, providing a functionalized surface having a structure of Formula VII:

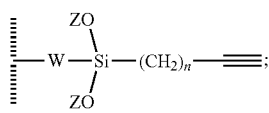

Formula VII where W, Z, and n are defined as above for Formula V, and ▤ is the surface.

Covalently modified surface formed from the functionalized surface. Once the surface functionalization reagent has been coupled to the surface, the reactive moiety of the resultant functionalized surface of Formula XXX, Formula V or Formula VII may be reacted in turn with a surface modifying reagent having a reaction pair moiety selected to be a suitable reaction partner to the reactive moiety of the functionalized surface. The surface modifying reagent has a structure of Formula XII:

RP-L-surface contact moiety      Formula XII;

where RP is a reaction pair moiety; L is a linker and surface contact moiety is a moiety that provides improved contact characteristics for biological micro-objects. Linker L may be a bond or may include 1 to 200 non-hydrogen atoms selected from any combination of silicon, carbon, nitrogen, oxygen, sulfur and phosphorus atoms, subject to chemical bonding limitations as is known in the art. In some embodiments, linker L may include 1 to 200 non-hydrogen atoms selected from any combination of silicon, carbon, nitrogen, oxygen, sulfur and phosphorus atoms, subject to chemical bonding limitations as is known in the art. Linker L or the surface contact moiety may include 0, 1, 2, or 3 coupling groups CG. Surface contact moiety is any surface contact moiety described herein.

Reaction Pair Moiety.

The reaction pair moiety RP is a moiety that can react with the reactive moiety of the functionalized surface. For example, a reactive moiety $R_x$ may be alkyne and a corresponding reaction pair moiety RP may be an azide. Alternatively, $R_x$ may be azide and RP may be alkyne. Other pairs of reactive moiety $R_x$:reaction pair moiety RP may include, but are not limited to cyano and azide; carboxylic acid and amine; olefin and nucleophile; amine and sulfonyl fluoride; trans cyclooctene and s-tetrazine, thiol and maleimide; halide and nucleophile; isocyanate and amines; epoxide and nucleophile; hydroxyamine and aldehyde or ester; and a masked hydroxyl such as acetate and nucleophile. A special case of Rx:RP pair is biotin and streptavidin as it is not a covalent pairing but an extremely stable noncovalent binding pair that may be used as an $R_x$:RP pair.

When the functionalized surface has an azide or a alkynyl moiety as $R_x$, the surface modifying reagent has a reaction pair moiety RP which is an alkyne or azide, respectively, which can react form a triazolylenyl moiety via a cyclization reaction ("Click reaction") as is known in the art. In some embodiments, the reactive moiety $R_x$ or the reaction pair RP moiety is an acyclic alkyne. In other embodiments, the s the reactive moiety $R_x$ or the reaction pair RP moiety is a cyclized alkyne, which may be part of a cyclooctyne. In some embodiments, the cyclooctyne may be strained. The cyclooctyne may have further cyclic rings fused to the cyclooctyne, such as benzo group, and may be a dibenzocyclooctyne. In other embodiments, the cyclooctyne may have fluoro substituents. When the alkyne of the surface modifying reagent is a cyclooctyne, the surface contact moiety of the reagent is attached to the cyclooctyne via the linker L, which may be attached to any suitable position on the cyclooctyne. When the alkyne of the functionalized surface is a cyclooctyne, the linking group attaching the cyclooctyne to the surface is attached to the cyclooctyne at any suitable position on the cyclooctyne.

The covalently modified surface resulting from the reaction of the functionalized surface of Formula XXX:

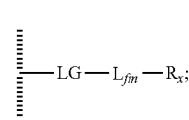

Formula XXX with a surface modifying reagent of Formula XII may have a structure of Formula XXXI:

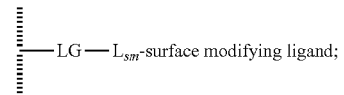

Formula XXXI wherein LG, $L_{sm}$, surface modifying ligand and ▤ are as defined above, and $L_{sm}$ or the surface modifying ligand includes at least one CG, and may further have 2, 3, or 4 CG.

In some embodiments, the covalently modified surface formed from the functionalized surface of Formula XXXI, Formula V, or Formula VII may have a structure of Formula VIII:

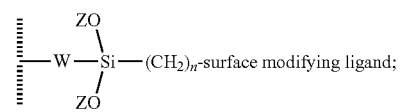

Formula VIII where W, Z, n, and ▤ are each defined as above. The surface modifying ligand may include 0, 1, 2, or 3 CG.

In some embodiments, the covalently modified surface formed from the functionalized surface of Formula XXXI may have a structure of Formula IX:

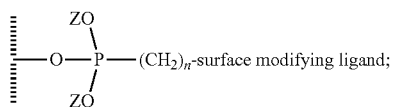

Formula IX where Z, n, and ⋮ are each defined as above. The surface modifying ligand may include 0, 1, 2, or 3 CG.

Additional Functionalization of the Functionalized Surface.

In yet other embodiments, the functionalized surface of Formula XXX may have a further portion of functionalization added by reaction with a secondary functionalizing reagent of Formula XXXIV:

$$RP-L_{fm}-R_{x2}$$ Formula XXXIV, wherein RP is a reaction pair moiety for reacting with the reactive moiety of Formula XXX; $R_{x2}$ is a reactive moiety selected to not react with the reactive moiety of the functionalizing surface of Formula XXX; and, $L_{fm}$ is a linker comprising 1 to 200 non-hydrogen atoms selected from any combination of silicon, carbon, nitrogen, oxygen, sulfur and phosphorus atoms and further comprises 0, 1 or 2 coupling groups CG. $R_{x2}$ is selected to have an orthogonal reaction pair moiety such that it does not interfere with the coupling of RP to the $R_x$ moiety of the functionalized surface. In some nonlimiting examples, when $R_x$ of the functionalized surface is azide, $R_{x2}$ may be selected to be amine, epoxide, or sulfonyl fluoride. This ability affords control in further elaboration of the functionalized surface.

The product is a functionalized surface of Formula XXXV, wherein the second functionalized surface comprises 1, 2, or 3 CG:

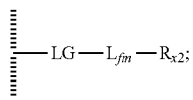

Formula XXXV where $R_{x2}$ is as defined for Formula XXXIV, and $L_{fm}$ and LG are as defined above for Formula XXX. When a functionalized surface of Formula V or Formula VII is reacted with a secondary functionalizing reagent of Formula XXXIV, the produce is a functionalized surface of formula XXXV, wherein LG is —W—Si(OZ)$_2$O— and W is O, S, or N. In some embodiments, W is O.

The functionalized surface of Formula XXXV may be converted to a covalently modified surface of Formula XXXI:

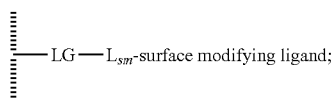

Formula XXXI where LG, $L_{sm}$ and surface modifying ligand are defined as above, by further reaction with a surface modifying reagent of Formula XII. In this embodiment, the surface modification (e.g., covalently modified surface) includes at least 2 CG within $L_{sm}$.

Figure 2A:
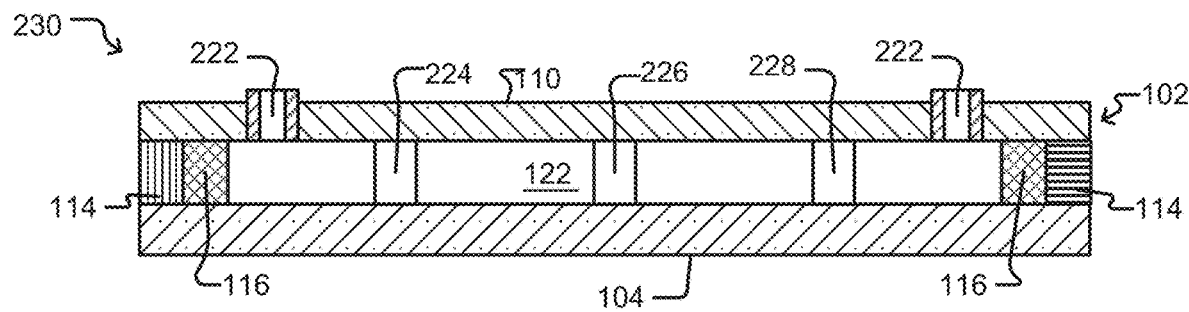
FIGS. 2A and 2B illustrate isolation pens according to some embodiments of the disclosure.
Figure 2B:
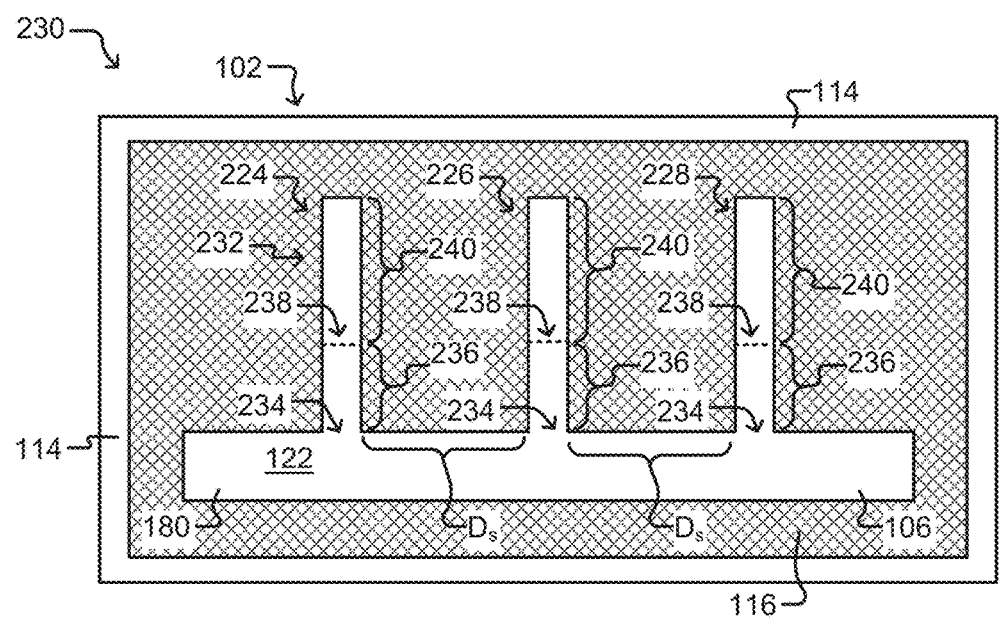
Figure 2C:
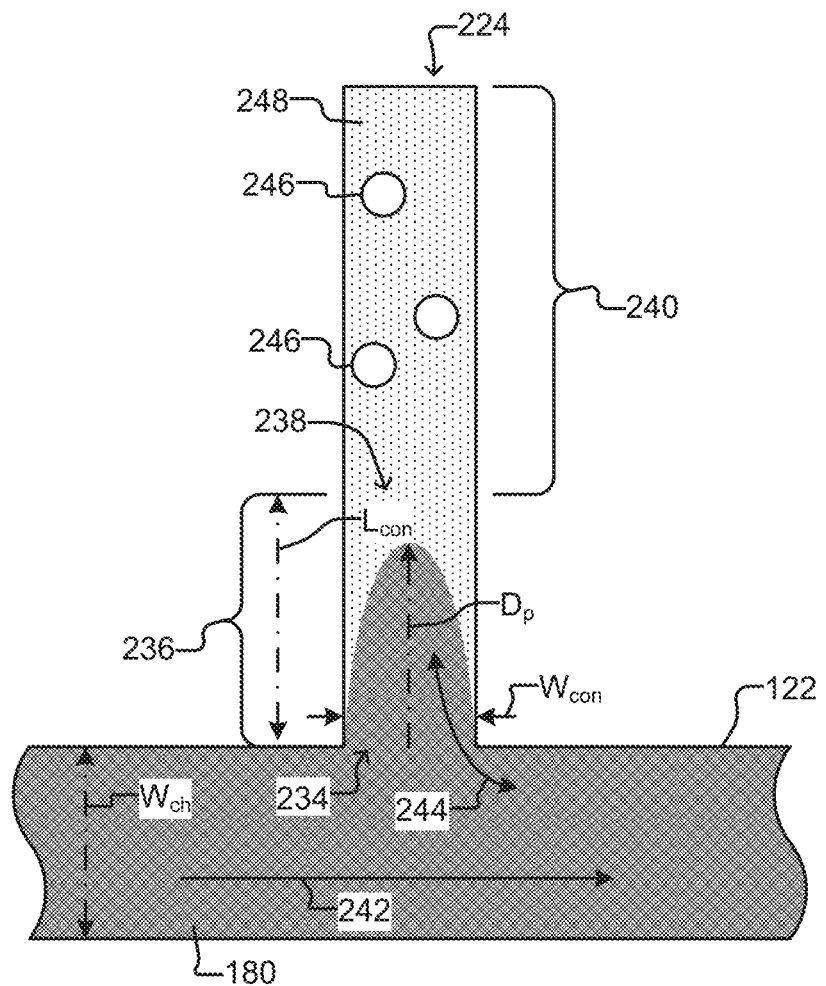
FIG. 2C illustrates a detailed sequestration pen according to some embodiments of the disclosure.
Figure 2D:
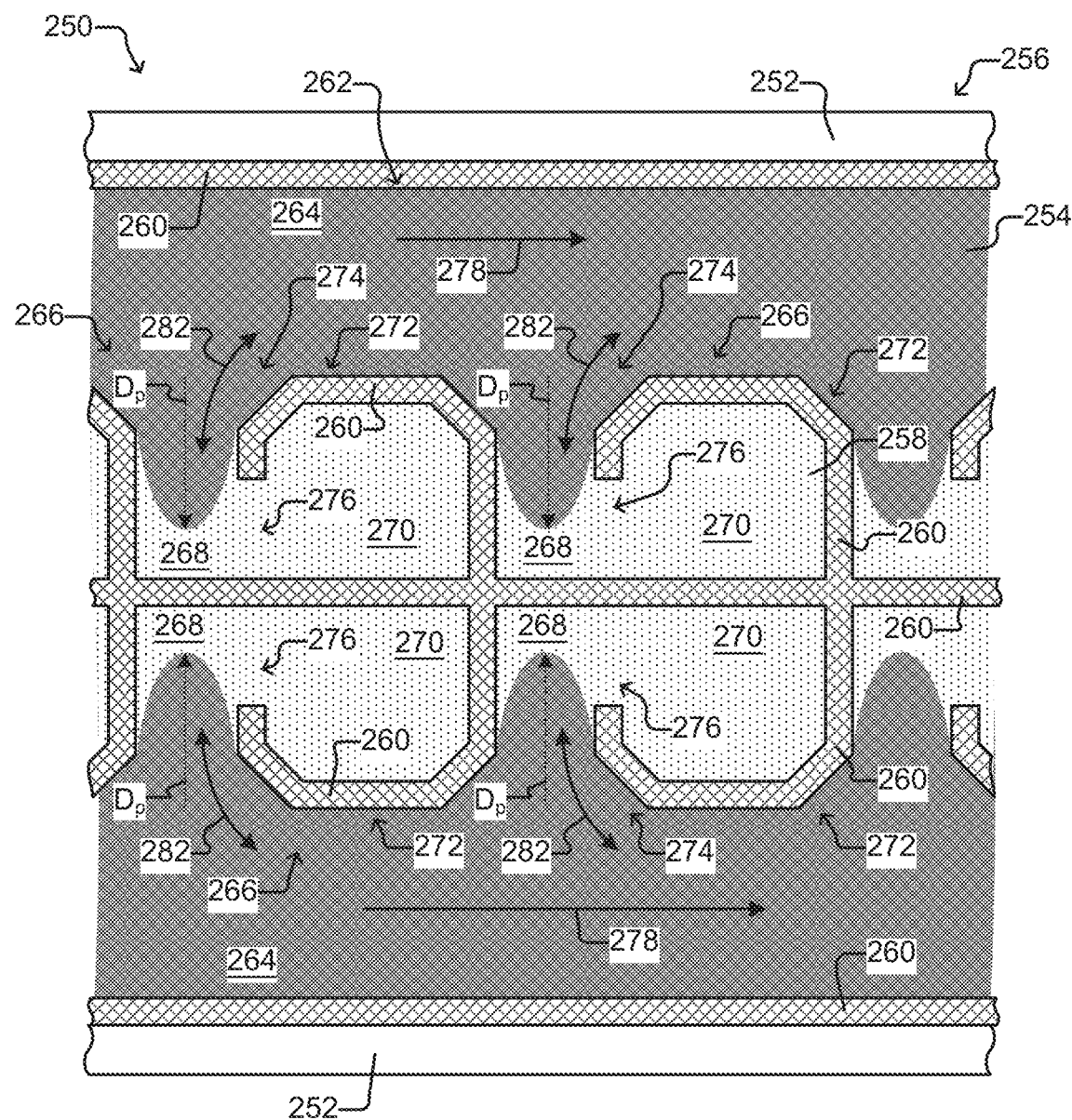
FIGS. 2D-F illustrate sequestration pens according to some other embodiments of the disclosure.
Figure 2E:
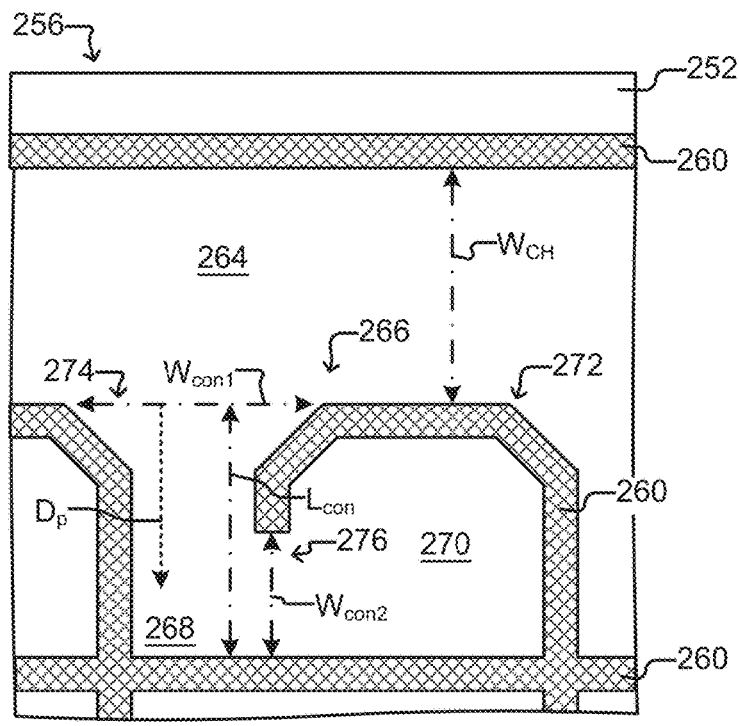
Figure 2F:
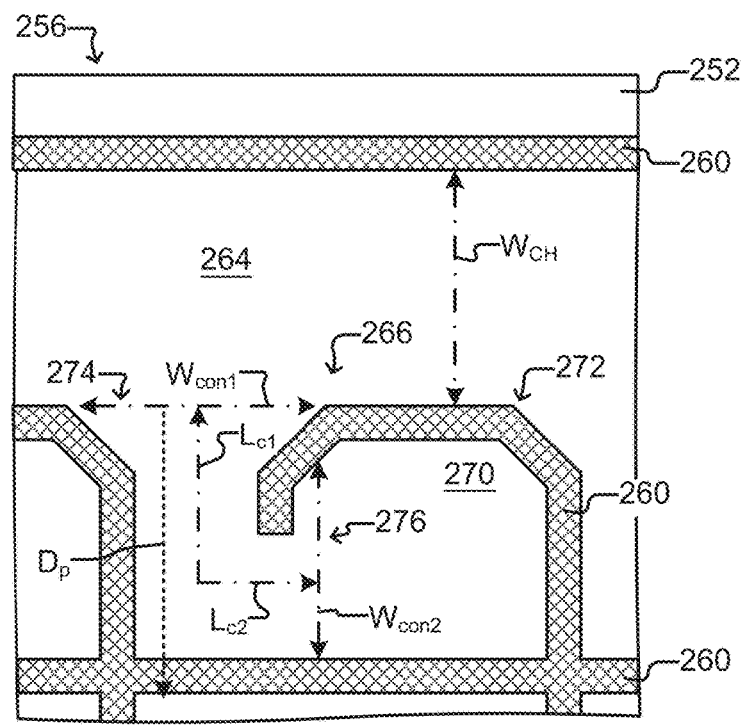
Figure 2G:
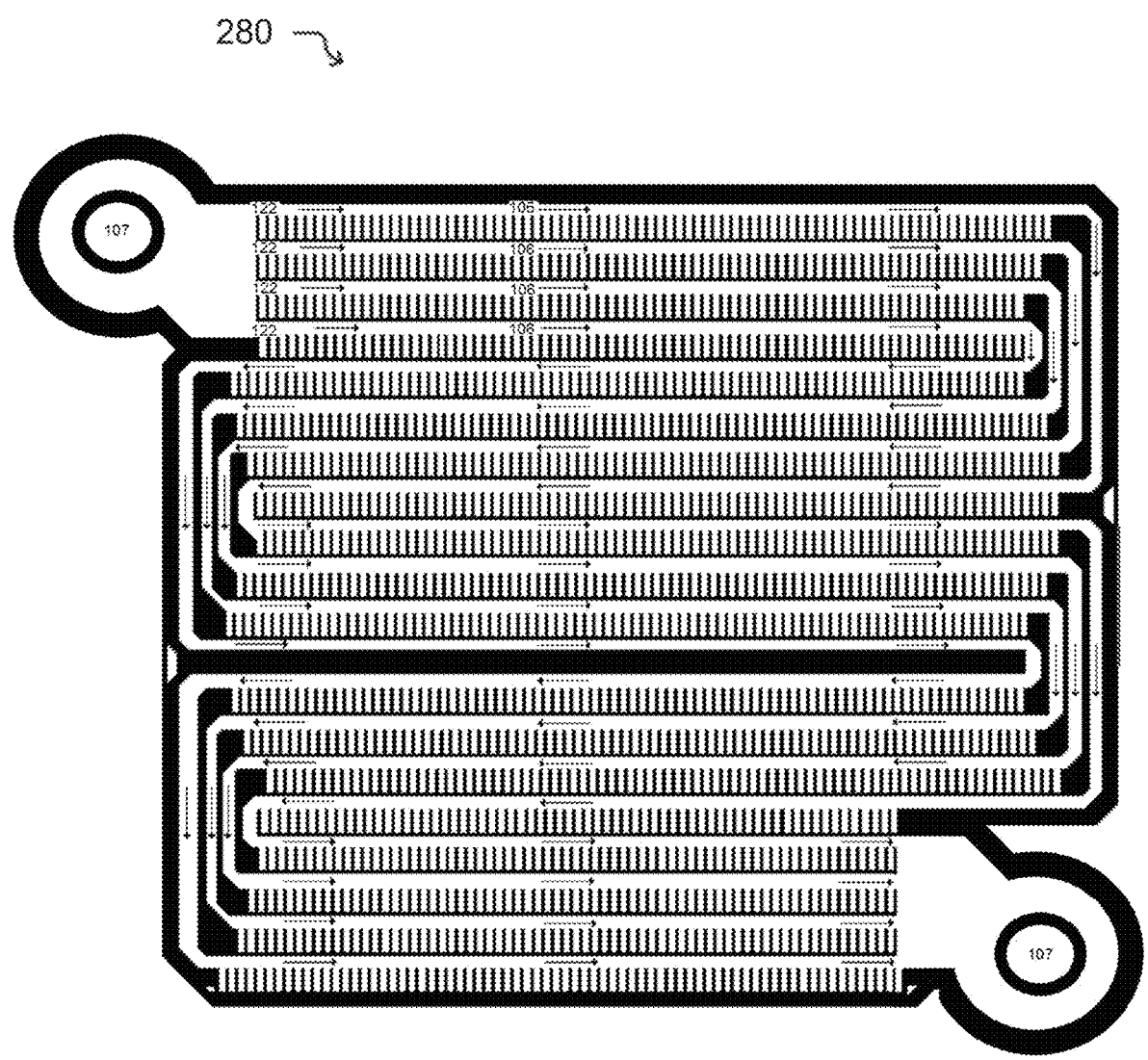
FIG. 2G illustrates a microfluidic device according to an embodiment of the disclosure.
Figure 2H:
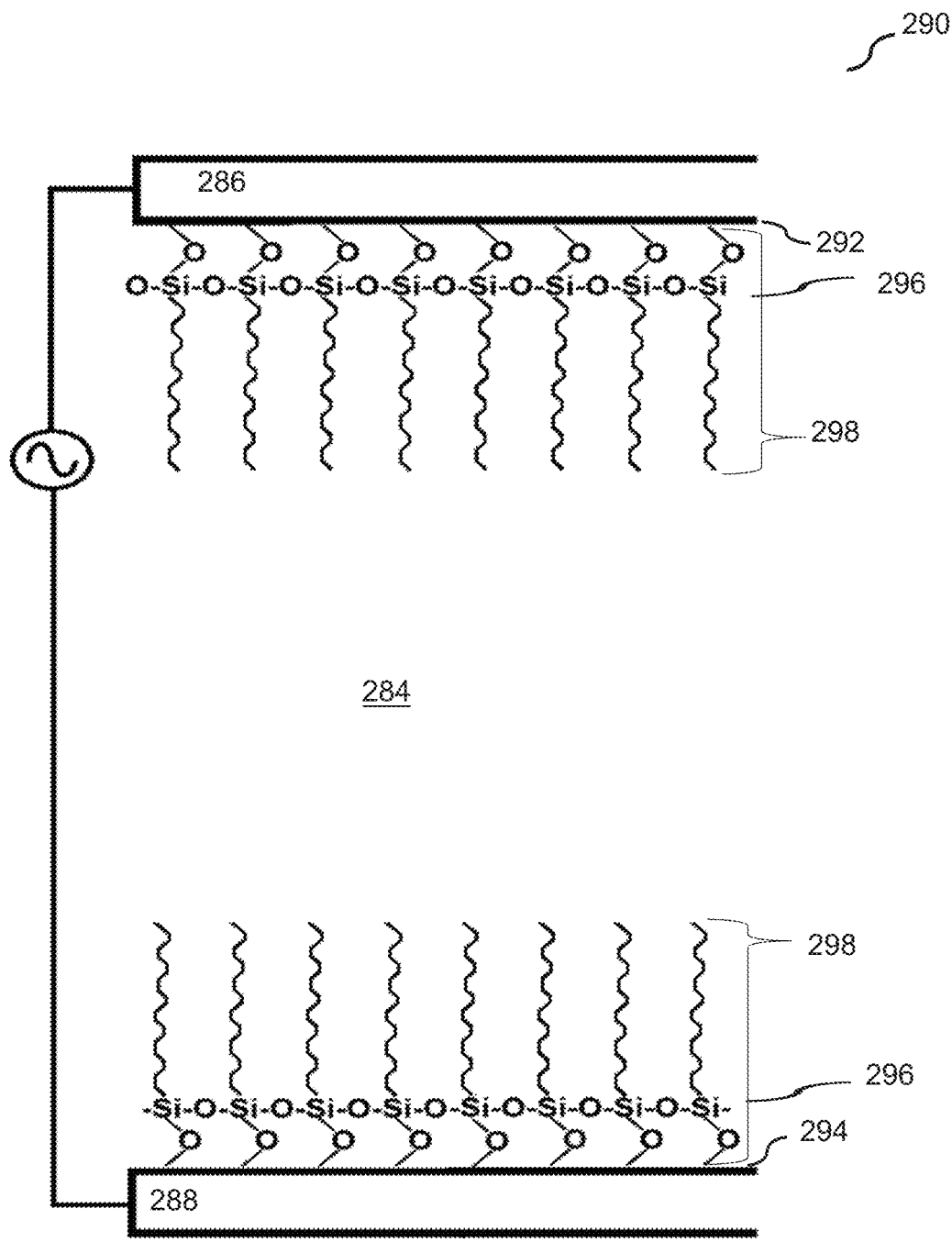
FIG. 2H illustrates a coated surface of the microfluidic device according to an embodiment of the disclosure.

FIG. 2H depicts a cross-sectional view of a microfluidic device 290 comprising an exemplary covalently modified surface 298. As illustrated, the covalently modified surface 298 (shown schematically) can comprise a monolayer of densely-packed molecules covalently bound to both the inner surface 294 of the substrate 286 and the inner surface 292 of the cover 288 of the microfluidic device 290. The covalently modified surface s 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the covalently modified surface 298 can be disposed on only one or some of the inner surfaces of the microfluidic device 290.

In the embodiment shown schematically in FIG. 2H, the covalently modified surface 298 includes a monolayer of substituted siloxane molecules, each molecule covalently bonded to the inner surfaces 292, 294 of the microfluidic device 290 via a siloxy linker 296. For simplicity, additional silicon oxide bonds are shown linking to adjacent silicon atoms, but the invention is not so limited. In some embodiments, the surface modifying ligand 298 can include any kind of nonpolymeric molecule as described herein (e.g. a fluorinated alkyl group, a polyethylene glycol containing group, an alkyl group containing a carboxylic acid substituent) at its enclosure-facing terminus (i.e. the portion of the monolayer of the surface modifying ligand 298 that is not bound to the inner surfaces 292, 294 and is proximal to the enclosure 284). While FIG. 2H is discussed as having non-polymeric surface modifying ligands, polymeric moieties may also be a suitable surface contacting moiety and/or surface modifying ligand, and be incorporated into the covalently modified surface, as described herein.

In other embodiments, the surface modifying ligand 298 used to covalently modify the inner surface(s) 292, 294 of the microfluidic device 290 can include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120, the surface modifying ligand of the covalently modified surface 298 can form strong hydrogen bonds with water molecules such that the resulting water of hydration acts as a layer (or "shield") that separates the biological micro-objects from interactions with non-biological molecules (e.g., the silicon and/or silicon oxide of the substrate).

Surface to be Modified.

A surface capable of being modified by the compound of any of Formulae XXXII, I, II, III, XXXIII, IV, VI, XII or XXXIV may be a metal, metal oxide, glass or polymer. Some materials that may have a covalently modified surface or a functionalized surface introduced therein may include but not be limited to silicon and its oxides, silicones, aluminum or its oxide thereof (Al$_2$O$_3$), Indium Tantalum Oxide (ITO), titanium dioxide (TiO$_2$), zirconium oxide (ZrO2), hafnium(IV) oxide (HfO$_2$), tantalum (V) oxide (Ta$_2$O$_5$), or any combination thereof. Polymers may include any suitable polymer. A suitable polymer may include but is not limited to (e.g. rubber, plastic, elastomer, silicone, organosilicone, such as polydimethylsiloxane ("PDMS"), or the like), which can be gas permeable. Other examples can include molded glass, a patternable material such as a silicone polymer (e.g. photo-patternable silicone or "PPS"), photo-resist (e.g., an epoxy-based photo-resist such as SU8), or the like. In other embodiments, a surface of a material such as a natural fiber or wood may be modified by the compound of any of Formulae XXXII, I, II, III, XXXIII, IV, VI, XII or XXXIV to introduce a covalently modified surface of Formula XXXI, Formula VIII, or Formula IX or a functionalized surface of Formula XXX, Formula V, Formula VII or Formula XXXV.

The surface to be modified may include a nucleophilic moiety including but not limited to hydroxide, amino and thiol. The nucleophilic moiety (e.g., hydroxide (in some embodiments referred to as oxide)) on the surface may react with the compound of any of Formulae XXXII, I, II, III, XXXIII, IV, or VI to covalently link the compound to the surface, via a siloxy linking group or phosphonate linking group, to provide the functionalized surface. The surface to be modified may include native nucleophilic moieties, or may be treated with reagents (e.g., piranha solution) or by plasma treatment to introduce nucleophilic moieties (e.g., hydroxide (alternatively referred to as oxide)).

Physical and Performance Properties of the Covalently Modified Surface.

In some embodiments, the covalently modified surface of Formula XXXI, Formula VIII or Formula IX may have a thickness of less than 10 nm (e.g., less than about 7 nm, less than about 5 nm, or about 1.5 to 3.0 nm). This may provide an advantageously thin layer on the modified surface, particularly in contrast with other hydrophobic materials such as CYTOP®, a perfluoro tetrahydrofuranyl polymer which is spin-coated yielding a typical thickness of about 30 to 50 nm. Data shown in Table 1 is for a silicon/silicon oxide native surface converted to a functionalized surface (e.g., Formula XV (a specific member of the class of Formula V) or a surface modified with surface contact moieties (e.g., Formula XVI and Formula XVII, specific embodiments of a modified surface of Formula VIII). Contact angle measurements were obtained using the static sessile drop method. (Drelich, J. Colloid Interface Sci. 179, 37-50, 1996.) Thickness was measured by ellipsometry.

TABLE 1

Physical data for selected surfaces.

| Functionalized or Modified Surface | Contact Angle (water or aqueous solution) | Thickness |
|---|---|---|
| Formula XV See Examples 3 and 5 | 80 degrees | 1.4-1.5 nm |
| Formula XVI (PEG, ~5000 Da) See Example 6 | 35 degrees | ~3 nm* |
| Formula XVII (Dextran ~3000 Da) See Example 7 | 40 degrees | Not available |
| Formula XVIII (PEG, ~5000 Da) See Example 8 | 34 degrees | ~4 nm* |
| Formula XIX (PGA) See Example 9 | 17 degrees | ~5 nm |
| Formula XX (biotin PEG) See Example 10 | 39 degrees | ~5 nm |
| Formula XXI (PC biotin PEG) See Example 11 | 42 degrees | ~5 nm |
| Formula XXII (propiolic acid) See Example 12 | 64 degrees | 2 nm |
| Formula XXIII (propargyl amine) See Example 13 | na | na |
| Formula XXIV (PEG carboxylic acid) See Example 14 | 42 degrees | ~5 nm |
| Formula XXV (poly lysine) See Example 15 | 50 degrees | 3 nm |
| Formula XXVI ((polyglutannic acid) See Example 16 | 54 degrees | 3 nm |
| Formula XXVII (Biotin PEG with disulfide linkage) See Example 17 | 66 degrees | 2 nm |

As expected, modification of a silicon/silicon oxide surface to have a functionalized surface of Formula XV, resulted in a modified surface having an increased contact angle for water, of about 80 degrees. This is in contrast to the contact angle for water on a plasma cleaned silicon surface of less than 10 degrees. Further elaboration of the functionalized surface to provide the modified surface of Formula XVI (including PEG moieties), yields a much more hydrophilic surface with a decreased contact angle of 35 degrees. A modified surface having a structure of Formula XVII (including dextran) had a contact angle of 40 degrees.

Other analytical methods suitable to characterize the surface can include infrared spectroscopy and/or X-ray photoelectron spectroscopy.

In some embodiments, the modified surface of Formula XXXI, Formula VIII, or Formula IX may form a monolayer. The uniformity and evenness of a monolayer modified surface may provide advantageous performance, particularly if the monolayer modified surface has other functional attributes. For example, the modified surface of Formula XXXI, Formula VIII or Formula IX may also include an electrode activation substrate, and optionally further may include a dielectric layer, as may be found in materials, devices and/or apparatuses having a dielectrophoresis configuration or an electrowetting configuration. The lack of unsaturation of the perfluoroalkyl moieties of the modified surface can minimize "charge trapping" compared to a monolayer containing, for example olefinic or aromatic moieties. Additionally, the densely-packed nature of the monolayer formed in the surfaces of Formula XXXI, Formula VIII or Formula IX may minimize the potential for cations to be driven through the monolayer to the underlying metal, metal oxide, glass or polymer substrate. Without being limited by theory, the disruption of the substrate surface by addition of cations to substrate composition may disrupt the electrical properties of the substrate, thereby reducing its ability to function electrokinetically.

Further, the ability to introduce the modified surface via a covalent linkage may increase the dielectric strength of the modified surface and protect the underlying material from breakdown under application of an electric field. The uniformity and thinness of a dielectrophoretic or electrowetting surface of a material, device and/or apparatus having a covalently modified structure of Formula XXXI, Formula VIII or Formula IX, may further provide advantageous benefit for such modified dielectrophoretic and/or electrowetting surface when the material, device and/or apparatus is optically actuated.

In some embodiments, the modified surface does not require a perfectly formed monolayer to be suitably functional for operation. The physical thickness and uniformity of the layer in the surface of any of Formula XXXI, Formula VIII, Formula IX, Formula XXX, Formula V, Formula VII or Formula XXXV can be measured using an ellipsometer.

Multiple Covalently Bonded Surface Modifications and Multilayer Surfaces.

The microfluidic device may have more than one region within the microfluidic device having a covalently modified surface modification where each region has only one kind of covalently linked moiety. Alternatively, the microfluidic device may include more than one different kind of covalently linked moiety on a single selected surface (e.g., a common inner surface of the microfluidic device) or on all of the internal surfaces of the microfluidic device.

For example, a first covalently bonded surface modification of a surface may have a specified number of non-hydrogen atoms as part of the linker and/or surface modifying ligand. A second covalently bonded surface modification of this surface may include a surface contact moiety having one or more charged moieties covalently attached to a linker having a greater number of non-hydrogen atoms, which may provide capacity to present the charged moieties further away from the surface so modified, potentially in closer contact with biological micro-objects within the microfluidic environment.

In another instance, the modified surface may have a first covalently bonded surface modification having a first type of less sterically demanding surface contact moiety and fewer non-hydrogen atoms in the linker attaching the first covalently bonded surface modification to the surface. The modified surface may have a second covalently bonded surface modification having a sterically demanding surface contact moiety and a linker having a greater number of non-hydrogen atoms. This mixture of covalently bonded surface modifications can help to present the sterically demanding surface contact moiety while prevent undesired interactions with silicon/silicon oxide, hafnium oxide or alumina making up the surface itself. In another example, the covalently linked moieties may provide a zwitterionic surface presenting oppositely charged surface contact moieties in a random fashion on the surface.

In other embodiments, the covalently modified surface may have increased hydrophilic and/or amphiphilic characteristics by introducing a combination of a first covalently bonded surface modification and a second covalently bonded surface modification. Introduction of the combination of first and second covalently bonded surface modifications can provide modulated or customizable hydrophilic, amphiphilic or hydrophobic characteristics to the surface (including a common inner surface of the microfluidic device.) The increased hydrophilic and/or amphiphilic character of a covalently modified surface may provide hydrophilic functionalities and/or hydrophobic moieties to which biological micro-objects may associate without irreversibly adhering. These associations may provide a beneficial environment during cell culture compared to native, unmodified surfaces of a microfluidic device.

Each of these characteristics may increase the durability, functionality, and/or biocompatibility of the modified surface. Each of these characteristics may further benefit the viability (including growth rate and/or cell doubling rate), nature of the colony formed upon a covalently modified surface having a structure of Formula XXXI, Formula VIII or Formula IX. Improvement of viability may include providing surface contact moieties providing adherent cells with suitable anchoring sites which provide sufficient mechanical resistance to promote growth. The covalently modified surface of Formula XXXI, Formula VIII or Formula IX may improve portability (including viability upon export) of micro-objects or biomolecules upon the modified surface and within devices and/or apparatuses having a covalently modified surface. In some other embodiments, a covalently modified surface having a structure of Formula XXXI, Formula VIII or Formula IX may provide surface contact moieties which discourage motile cells from migration out of a specific region of a microfluidic device (e.g., a sequestration pen), thereby minimizing cell movement out of the selected region. The portability of the cells may in this instance be inhibited, preventing self-propelled movement of cells from one sequestration pen to another and minimizing contamination from sequestration pen to sequestration pen. However, modulation of such inhibitory effect may be obtained by selection of the ratio of different covalently bound surface modification to still be able to export from the sequestration pen at a desired timepoint using forces such as gravity or dielectrophoresis (which may be light actuated).

The combination of covalently bonded surface modifications may be any combination of a covalently modified surface and/or a functionalized surface or secondary functionalized surface as described herein. Any combination of the linking group, linker, reactive moiety and/or surface contact moiety may be selected for the microfluidic device having a first and a second covalently bound surface modification where the first and the second covalently bonded surface modification are different from each other. The first and the second covalently bonded surface modifications may be any of Formula XXX, Formula V, Formula VII, Formula XXXI, Formula VIII, and/or Formula IX.

In some embodiments, the microfluidic device may have one or both of the first and the second covalently bonded surface modifications that are functionalized surfaces, for further modification by the user. A microfluidic device having one or two functionalized surfaces, differing in reactive moiety, linker, and/or linking group, may either be reacted with a surface modifying reagent (e.g., a reagent of Formula XII) to provide a covalently modified surface or may be further functionalized by reaction with a secondary functionalizing reagent (e.g., a reagent of Formula XXXIV) to provide a secondary functionalized surface. Orthogonal chemistries (e.g. reaction moieties and reaction pair moieties, and reaction conditions), as are known in the art, may be selected to permit selective reaction of one functionalized surface in the presence of a second functionalized surface or in the presence of a covalently modified surface. In one nonlimiting example, when an alkyne is present as a first reactive moiety (Rx or Rx2) of the first covalently bonded surface modification, it is designed to react with an azide as a reaction pair moiety. The second covalently bound surface modification may have a second reactive moiety selected to be an amine or carboxylic acid, which do not take part in a "Click" type reaction.

In some embodiments, a covalently modified surface may include a combination of: a functionalized surface of Formula XXX, Formula V or Formula VII; and, a first covalently bound surface modification of Formula XXXI, Formula VIII or Formula IX. The combination of the functionalized surface and the first covalently bound surface modification of Formula XXXI, Formula VIII or Formula IX may be randomly distributed upon the covalently modified surface. In other embodiments, the covalently modified surface may have a first region having the functionalized surface of Formula XXX, Formula V or Formula VII abutting a second region including the first covalently bound surface modification of Formula XXXI, Formula VIII or Formula IX. In other embodiments, the covalently modified surface may include a plurality of regions having the first covalently bound surface modification of Formula XXX, Formula VIII or Formula IX separated from each other by the functionalized surface of Formula XXXI, Formula V or Formula VII. In yet other embodiments, the covalently modified surface may have a plurality of regions including the functionalized surface of Formula XXX, Formula V or Formula VII separated from each other by the first covalently bound surface modification of Formula XXXI, Formula VIII or Formula IX.

In other embodiments, the covalently modified surface may have a combination of: a first covalently bound surface modification of Formula XXXI, Formula VIII or Formula IX; and a second covalently bound surface modification of Formula XXXI, Formula VIII or Formula IX, where the first and the second covalently bound surface modifications are different. In some embodiments, the first and second covalently bound surface modifications, which differ from each other, may be randomly distributed on the covalently modified surface. In some other embodiments, the covalently modified surface may have a first region having the first covalently bound surface modification of Formula XXXI, Formula VIII or Formula IX which abuts a second region having the second covalently bound surface modification of Formula XXXI, Formula VIII or Formula IX. In yet other embodiments, the covalently modified surface may have a plurality of regions having the first covalently bound surface modification of Formula XXXI, Formula VIII or Formula IX, which are separated from each other by the second covalently bound surface modification of Formula XXXI, Formula VIII or Formula IX In further embodiments, the covalently modified surface may have a combination of: a first covalently bound surface modification of Formula XXX, Formula V or Formula VII; and a second covalently bound surface modification of Formula XXX, Formula V or Formula VII, wherein the first and the second covalently bound surface modifications are different and the reactive moiety of the first covalently bound surface modification does not react with the reactive moiety of the second covalently bound surface modification. In some embodiments, the first and the second covalently bound surface modifications may be randomly distributed upon the surface. In some other embodiments, the covalently modified surface may include a first region having the first covalently bound surface modification of Formula XXX, Formula V or Formula VII abutting a second region having the second covalently bound surface modification of Formula XXX, Formula V or Formula VII. In yet other embodiments, the covalently modified surface may have a plurality of regions including the first covalently bound surface modification of Formula XXX, Formula V or Formula VII which are separated from each other by the second covalently bound surface modification of Formula XXX, Formula V or Formula VII.

Multiple Surface Modifications to Modulate Adhesion.

In some embodiments, it can be useful to modulate the capacity for cells to adhere to surfaces within the microfluidic device. A surface that has substantially hydrophilic character may not provide anchoring points for cells requiring mechanical stress of adherence to grow and expand appropriately. A surface that presents an excess of such anchoring moieties may prevent successfully growing adherent cells from being exported from within a sequestration pen and out of the microfluidic device. combine surface second covalently bound surface modification comprises surface contact moieties to help anchoring adherent cells. The structures of the surfaces described herein and the methods of preparing them provide the ability to select the amount of anchoring moieties that may be desirable for a particular use. It has been surprisingly discovered that a very small percentage of adherent type motifs may be needed to provide a sufficiently adhesion enhancing environment. In some embodiments, the adhesion enhancing moieties are prepared before cells are introduced to the microfluidic device. Alternatively, an adhesion enhancing modified surface may be provided before introducing cells, and a further addition of another adhesion enhancing moiety may be made, which is designed to attach to the first modified surface either covalently or non-covalently (e.g., as in the base of biotin/streptavidin binding)

In some embodiments, adhesion enhancing surface modifications may modify the surface in a random pattern of individual molecules of a surface modifying ligand. In some other embodiments, a more concentrated pattern of adhesion enhancing surface modifications may be introduced by using polymers containing multiple adhesion enhancing motifs such as positively charged lysine side chains, which can create small regions of surface modification surrounded by the remainder of the surface, which may have hydrophilic surface modifications to modulate the adhesion enhancement. This may be further elaborated by use of dendritic polymers, having multiple adhesion enhancing ligands. A dendritic polymer type surface modifying compound or reagent may be present in a very small proportion relative to a second surface modification having only hydrophilic surface contact moieties, while still providing adhesion enhancement. Further a dendritic polymer type surface modifying compound or reagent may itself have a mixed set of end functionalities which can additionally modulate the behavior of the overall surface.

In some embodiments, it may be desirable to provide regioselective introduction of surfaces. It may be desirable to provide a first type of surface within the microfluidic channel while providing a surface within the sequestration pens opening off of the channel that provides the ability to both culture adherent-type cells successfully as well as easily export them using dielectrophoretic forces when desired. In some embodiments, the adhesion enhancing modifications may include cleavable moieties. The cleavable moieties may be cleavable under conditions compatible with the cells being cultured within, such that at any desired timepoint, the cleavable moiety may be cleaved and the nature of the surface may alter to be less enhancing for adhesion. The underlying cleaved surface may be usefully non-fouling such that export is enhanced at that time. While the examples discussed herein focus on modulating adhesion and motility, the use of these regioselectively modified surfaces are not so limited. Different surface modifications for any kind of benefit for cells being cultured therein may be incorporated into the surface having a first and a second surface modification according to the disclosure.

Adherent Motifs.

Generally, a surface modification having a positively charged surface contact moiety such as poly-L-lysine, amine and the like may be used within the modified surfaces of the disclosure. Another motif that may be used includes the tripeptide sequence RGD, which is available as a biotinylated reagent and is easily adaptable to the methods described herein. Other larger biomolecules that may be used include fibronectin, laminin or collagen, amongst others. Surprisingly, a surface modification having a structure of Formula XXVI, including a polyglutamic acid surface contact moiety, demonstrated the ability to induce adherent cells to attach and grow viably. Another motif that may assist in providing an adherent site is an Elastin Like Peptide (ELP), which includes a repeat sequence of VPGXG, where X is a variable amino acid which can modulate the effects of the motif.

Regioselective Introduction of Differing Surfaces.

In some embodiments, a surface of the flow region (e.g., microfluidic channel) may be modified with a first covalently bound surface modification and a surface of the at least one sequestration pen may be modified with a second covalently bound surface modification, wherein the first and the second covalently bound surface modification have different surface contact moieties, different reactive moieties, or a combination thereof. The first and the second covalently bound surface modifications may be selected from any of Formula XXX, Formula V, Formula VII, Formula XXXI, Formula VIII, and/or Formula IX. When the first and the second covalently bound surface modifications both include functionalized surface of Formula XXX, Formula V, or Formula VII, then orthogonal reaction chemistries are selected for the choice of the first reactive moiety and the second reactive moiety. In various embodiments, all the surfaces of the flow region may be modified with the first covalent surface modification and all the surfaces of the at least one sequestration pen may be modified with the second covalent modification.

In some embodiments, the microfluidic device may have a surface of a combination of first and second covalently bound surface modification selected from the surfaces of Formula V, Formula XVI, Formula XVII, Formula XVIII, Formula XIX, Formula XX, Formula XXI, Formula XXII, Formula XXIII, Formula XXIV, Formula XXV, Formula XXVI, Formula XXVII, Formula XXVIII, Formula XXIX, Formula XXXVI, Formula XXXVII, Formula XXXVIII, Formula XXXIX, or Formula XL. In other embodiments the microfluidic device may have one region of the microfluidic device having a first covalently bound surface modification as well as a second region of the microfluidic device having a second covalently bound surface modification (e.g., the flow region having the first covalently bound surface modification and the sequestration pen having the second covalently bound surface modification) which may be selected from the surfaces of Formula V, Formula XVI, Formula XVII, Formula XVIII, Formula XIX, Formula XX, Formula XXI, Formula XXII, Formula XXIII, Formula XXIV, Formula XXV, Formula XXVI, Formula XXVII, [Formula XXVIII, Formula XXIX, Formula XXXVI, Formula XXXVII, Formula XXXVIII, Formula XXXIX, or Formula XL.

Methods of Preparation of the Covalently Modified Surface.

A surface of a material that may be used as a component of a device or apparatus may be modified before assembly of the device or apparatus. Alternatively, partially or completely constructed device or apparatus may be modified such that all surfaces that will contact biomaterials including biomolecules and/or micro-objects (which may include biological micro-objects) are modified at the same time. In some embodiments, the entire interior of a device and/or apparatus may be modified, even if there are differing materials at different surfaces within the device and/or apparatus. In some embodiments, the partially or completely constructed device and/or apparatus may be a microfluidic device as described herein, or a component thereof.

The surface to be modified may be cleaned before modification to ensure that the nucleophilic moieties on the surface are freely available for reaction, e.g., not covered by oils or adhesives. Cleaning may be accomplished by any suitable method including treatment with solvents including alcohols or acetone, sonication, steam cleaning and the like. Alternatively, or in addition, such pre-cleaning can include treating the cover, the microfluidic circuit material, and/or the substrate in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide from about 3:1 to about 7:1) may be used in place of an oxygen plasma cleaner.

This can advantageously provide more sites for modification on the surface, thereby providing a more closely packed modified surface layer.

Methods of Covalently Modifying a Surface Include Modifying a Surface with a Surface Modification Reagent of Formula XXXII, Formula I or Formula III.

Introducing a covalently modified surface may include contacting the surface with the surface modifying compound of Formula XXXII:

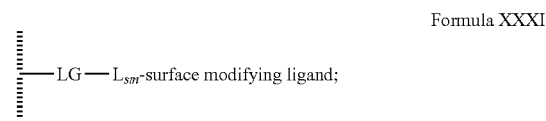

where V, $L_{sm}$, and surface modifying ligand are defined as above; reacting the reagent of Formula XXXII with a nucleophilic moiety of the surface; and, forming a covalently modified surface of Formula XXXI:

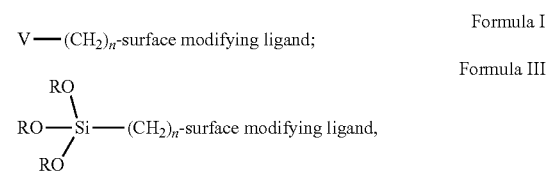

where LG. In some embodiments, the surface modifying compound of Formula XXXII is a compound o and the surface ▌ is defined as above f Formula I or Formula III:

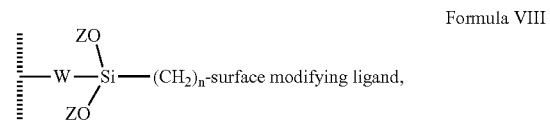

where the covalently modified surface produced is a surface of Formula VIII:

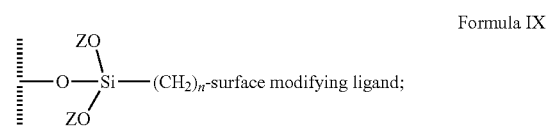

where Z is a bond to an adjacent silicon atom or is a bond to the surface and the surface ▌ is defined as above.

In other embodiments, the surface produced by reaction of the surface modifying compound of Formula XXXI is a surface having the structure of Formula IX:

$$\begin{array}{c} \text{ZO} \\ \text{▌—O—Si—(CH}_2)_n\text{-surface modifying ligand;} \\ \text{ZO} \end{array} \quad \text{Formula IX}$$

wherein Z is a bond to an adjacent phosphorus atom or is a bond to the surface and the surface ▌ is defined as above.

Methods of Covalently Modifying a Surface Include Functionalizing a Surface with a Functionalizing Reagent of Formula XXXIII, Formula IV or Formula VI.

Covalently functionalizing a surface with a functionalizing reagent of Formula XXXIII may include: contacting the surface with the reagent of Formula XXXIII:

  Formula XXXIII;

reacting the reagent of Formula XXXIII with a nucleophilic moiety of the surface; and, forming a functionalized surface of Formula XXX:

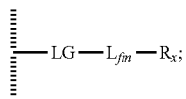  Formula XXX wherein V, $L_{fm}$, $R_x$ and LG are as defined above.

In some embodiments, the functionalizing reagent of Formula XXXIII is a functionalizing reagent of Formula IV or Formula VI, having a structure of one of the following formulae:

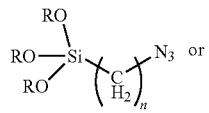  Formula IV

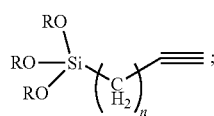  Formula VI and providing a functionalized surface of Formula V or Formula VII, respectively:

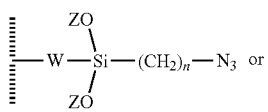  Formula V

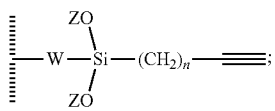  Formula VII

W, Z, and n are as defined above, and ≡ is the surface. In some embodiments, W is O. Each instance of R may be independently H or $C_1$-$C_6$ alkyl. In some embodiments, n may be an integer of 7 to 21. In other embodiments, n may be 9, 14, or 16. In other embodiments, n is 9. In some embodiments, R is $C_1$-$C_3$ alkyl. In other embodiments, R is methyl or ethyl. In yet other embodiments, R is methyl.

For Surface Modifying Reactions and Surface Functionalizing Reactions.

In some embodiments, the nucleophilic moiety of the surface is a hydroxide, amino or thiol. In some other embodiments, the nucleophilic moiety of the surface may be a hydroxide. The surface may be a metal, metal oxide, glass, polymer, or any combination thereof. Surface materials that may be modified by this method may be any material described herein.

The contacting step may be performed by contacting the surface with a liquid solution containing the modifying reagent(s) of Formula XXXIII, Formula IV, Formula VI, Formula XXXII, Formula I, and/or Formula III, which may be any combination as described herein. For example, surfaces may be exposed to solutions containing 0.01 mM, 0.1 mM, 0.5 mM, 1 mM, 10 mM, or 100 mM of the modifying reagent(s) of Formula XXXIII, Formula IV, Formula VI, Formula XXXII, Formula I, and/or Formula III. The reaction may be performed at ambient temperature and may be carried out for a period of time in the range of about 2 h, 4 h, 8 h, 12 h, 18 h, 24 h, or any value inbetween. Examples of solvents include but are not limited to: dimethyl formamide (DMF), acetonitrile (ACN), toluene, 1,3 bistrifluorobenzene, or Fluorinert™ (3M) fluorinated solvents. An acid such as acetic acid may be added to the solution to increase the reaction rate by promoting hydrolysis of the trialkoxy groups, if present.

Alternatively, the surface may be contacted with a vapor phase containing the modifying reagent(s) of Formula XXXIII, Formula IV, Formula VI, Formula XXXII, Formula I, and/or Formula III, which may be any combination as described herein. In some embodiments, when the reacting step is performed by contacting the surface with the modifying reagent(s) of Formula XXXIII, Formula IV, Formula VI, Formula XXXII, Formula I, and/or Formula III in the vapor phase, a controlled amount of water vapor is also present. The controlled amount of water vapor may be provided by placing a preselected amount of magnesium sulfate heptahydrate in the same chamber or enclosure with the object having the surface to be modified. In other embodiments, a controlled amount of water may be introduced into the reaction chamber or enclosure via an external water vapor feed. The reaction may take place under reduced pressure, relative to atmospheric pressure.

The reaction may be conducted at a temperature greater than about 95° C., or from about 100° C. to about 200° C. In various embodiments, the reaction may be conducted at a temperature of about 100° C., 110° C., 120° C., 130° C., 140° C., 150° C., 160° C., 170° C., 180° C., 190° C., or about 200° C. The reaction may be permitted to continue for about 2 h, 6 h, 8 h, 18 h, 24 h, 48 h, 72 h, 84 h, or more.

The modified and/or functionalized surface, in some embodiments, may be a monolayer. In some embodiments, the modified and/or functionalized surface may include at least one surface of a microfluidic circuit element of a microfluidic chip. In other embodiments, the modified and/or functionalized surface may include all of the surfaces facing fluid bearing portions of a microfluidic device. For example, in exemplary microfluidic devices 200, 230, the inner surface of the top electrode 210, the inner surface 208 of the electrode activation substrate 206, the surfaces of the microfluidic circuit material 116 (See FIGS. 1B, 2A, 2B), all of which face the microfluidic channel 122 and pens 224, 226, 228 may be functionalized. Similarly, in FIGS. 2D-2F, the inner surfaces of microfluidic circuit material 260, surfaces of isolation structures 272 which define the sequestration pen 270, or all the surfaces facing the microfluidic circuit 262 may be modified by reaction with the modifying reagent(s) of Formula XXXIII, Formula IV, Formula VI, Formula XXXII, Formula I, and/or Formula III.

Further Modification of a Functionalized Surface.

A method of covalently modifying a surface can include providing a functionalized surface having a structure of Formula XXX:

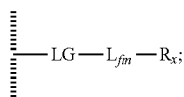

Formula XXX where LG, $L_{fm}$, and $R_x$ are each defined as above and ⫯ is the surface; reacting the reactive moiety $R_x$ with a surface modifying reagent having a structure of Formula XII:

RP-L-surface contact moiety          Formula XII;

where RP is a reaction pair moiety; L is a linker and surface contact moiety is as defined above. Linker L may be a bond or may include 1 to 200 non-hydrogen atoms selected from any combination of silicon, carbon, nitrogen, oxygen, sulfur and phosphorus atoms, subject to chemical bonding limitations as is known in the art. In some embodiments, linker L may include 1 to 200 non-hydrogen atoms selected from any combination of silicon, carbon, nitrogen, oxygen, sulfur and phosphorus atoms, subject to chemical bonding limitations as is known in the art. Linker L or the surface contact moiety may include 0, 1, 2, or 3 coupling groups CG; and thereby produces the covalently modified surface, having a structure of Formula XXXI:

Formula XXXI

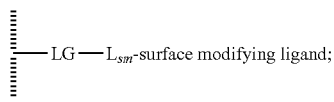

where $L_{sm}$ is as defined above.

In some embodiments, the functionalized surface of Formula XXX may be a functionalized surface of Formula V or Formula VII:

Formula V

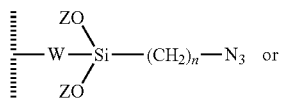

Formula VII

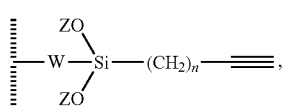

where W is O, S, or N, Z is a bond to an adjacent silicon atom bound to the surface or is a bond to the surface, n is an integer of about 3-21, In some embodiments, n is an integer of 7 to 21. The adjacent silicon atom to which Z is attached to may be incorporated in another surface modification molecule as described above. The covalently modified surface produced may a surface modification molecule having a structure of Formula VIII:

Formula VIII

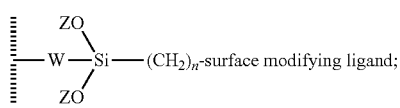

where S, Z, n and ⫯ are each as defined above for Formula V or Formula VII. When Z is a bond to an adjacent silicon atom, the silicon atom may be part of another surface modification molecule of the following formula:

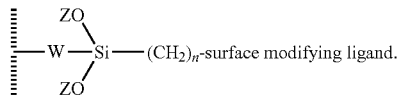

In some embodiments, n is an integer of 9 to 21. In other embodiments, n is 9, 14, or 16. In other embodiments, n is 9. In some embodiments, W is O.

In other embodiments, the product covalently modified surface having a structure of Formula XXXI, may have a structure of Formula IX:

Formula IX

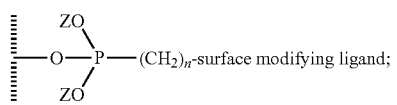

wherein Z is a bond to an adjacent phosphorus atom or is a bond to the surface and the surface ⫯ is defined as above.

When an alkyne is present in the functionalized surface ($R_x$) or the surface modifying reagent of Formula XII (RP reaction pair moiety), it may be an acyclic alkyne, and the reaction with an azide in a "Click" cyclization reaction may be catalyzed by a copper (I) salt. When a copper (I) salt is used to catalyze the reaction, the reaction mixture may optionally include other reagents which can enhance the rate or extent of reaction. When an alkyne of the surface modifying reagent or the functionalized surface is a cyclooctyne, the "Click" cyclization reaction with an azide of the corresponding functionalized surface or the surface modifying reagent may be copper free. A "Click" cyclization reaction, thereby couples the surface modifying ligand to the functionalized surface to form the covalently modified surface. The cyclization reaction may be catalyzed by a copper (I) salt, and may optionally include other reagents which can enhance the rate or extent of reaction. As described above for the functionalized surface, a covalently modified surface may be at least one surface of a microfluidic device. In some embodiments, the covalently modified surface may include substantially all the fluid-facing surfaces of the interior of the microfluidic device.

Copper Catalysts.

Any suitable copper (I) catalyst may be used. In some embodiments, copper(I) iodide, copper (I) chloride, copper (I) bromide or another copper (I) salt. In other embodiments, a copper (II) salt may be used in combination with a reducing agent such as ascorbate to generate a copper (I) species in situ. Copper sulfate or copper acetate are non-limiting examples of a suitable copper (II) salt. In other embodiments, a reducing agent such as ascorbate may be present in combination with a copper (I) salt to ensure sufficient copper(I) species during the course of the reaction. Copper metal may be used to provide Cu(I) species in a redox reaction also producing Cu(II) species. Coordination complexes of copper such as [CuBr(PPh3)3], silicotungstate complexes of copper, [Cu(CH3CN)4]PF6, or (Eto)3P CuI may be used. In yet other embodiments, silica supported copper catalyst, copper nanoclusters or copper/cuprous oxide nanoparticles may be employed as the catalyst.

Other Reaction Enhancers.

As described above, reducing agents such as sodium ascorbate may be used to permit copper(I) species to be maintained throughout the reaction, even if oxygen is not rigorously excluded from the reaction. Other auxiliary ligands may be included in the reaction mixture, to stabilize the copper(I) species. Triazolyl containing ligands can be used, including but not limited to tris(benzyl-1H-1,2, 3-triazol-4-yl) methylamine (TBTA) or 3 [tris(3-hydroxypropyltriazolylmethyl)amine (THPTA). Another class of auxiliary ligand that can be used to facilitate reaction is a sulfonated bathophenanthroline, which is water soluble, as well, and can be used when oxygen can be excluded.

Other chemical couplings as is known in the art may be used to couple a surface modifying reagent to the functionalized surface as described for Reaction Pair moiety.

Solvents and Reaction Conditions.

When an interior surface of a microfluidic device is the functionalized surface that reacts with a surface modifying reagent, the reaction may be performed by flowing a solution of the surface modifying reagent into and through the microfluidic device. In various embodiments, the surface modifying reagent solution may be an aqueous solution. Other useful solvents include aqueous dimethyl sulfoxide (DMSO), DMF, acetonitrile, or an alcohol may be used. The reaction may be performed at room temperature or at elevated temperatures. In some embodiments, the reaction is performed at a temperature in a range from about 15° C. to about 60° C.; about 15° C. to about 55° C.; about 15° C. to about 50° C.; about 20° C. to about 45° C. In some embodiments, the reaction to convert a functionalized surface of a microfluidic device to a covalently modified surface is performed at a temperature of about 15° C., 20° C., 25° C., 30° C., 35° C., 40° C., 45° C., 50° C., 55° C., or about 60° C.

Methods of Producing the Combined Surfaces.

A method of preparing a covalently modified surface on at least one inner surface of a microfluidic device having an enclosure including a base, a cover and microfluidic circuit material defining a fluidic circuit therein, includes: contacting the at least one inner surface with a first modifying reagent and a second modifying reagent; reacting the first modifying reagent with a first nucleophilic moiety of the at least one inner surface; reacting the second modifying reagent with a second nucleophilic moiety of the at least one inner surface; and, forming the at least one covalently modified surface comprising a first covalently bound surface modification comprising a first linking group and a first moiety that is a first surface contact moiety or a first reactive moiety; and a second covalently bound surface modification comprising a second linking group and a second moiety that is a second surface contact moiety or second reactive moiety, wherein the first linking group is different from the second linking group or the first moiety is different from the second moiety.

In some embodiments, the reaction of the first modifying reagent with the surface may be performed at the same time as reacting the second modifying reagent. For example, when the first modifying reagent and the second modifying reagent are both surface modifying compounds (e.g., Formula XXXII, Formula I, Formula II, Formula III), a mixture of the two surface modifying reagents, such as, but not limited to two different siloxane reagents, may be reacted via chemical vapor deposition at the same time. The ratio of the two reagents may be varied in order to obtain different percentages of the two surface modifications (e.g., surface modification ligands) as desired. In another example, the surface may be a functionalized surface and the first and second modifying reagents are surface modifying reagent(s) (e.g, Formula XII) and/or secondary functionalizing reagent (s) (Formula XXXIV), and the mixture of the two modifying reagents may be reacted with the reactive moiety of the functionalized surface at the same time.

In other embodiments, the reaction of the first modifying reagent with the surface may be performed before or after reacting the second modifying reagent with the at least one inner surface of the microfluidic device. For example, the surface may be a functionalized surface (having a surface of Formula XXX, Formula V or Formula VII) and the first modifying reagent may be a secondary functionalizing reagent, which can introduce an orthogonal $R_{x2}$ or a surface modifying reagent. A reaction may be performed with limited amounts of the secondary functionalizing reagent such that only a portion of the reactive moieties $R_x$ of the functionalized surface. Alternatively, the first reaction may be performed with a limited amount of a surface modifying reagent such that not all of the reactive moieties are coupled. This may be performed to introduce, for example, a longer linker region in these first introduced surface modifications. A following reaction can introduce a second surface modification with use of a surface modifying reagent that can introduce a desired surface contact moiety on all of the exposed reactive moieties or may only react with the unreacted original reactive moiety sites. If an orthogonal $R_{x2}$ has been introduced, a further reaction may be performed with a suitable surface modifying reagent which reacts only with $R_{x2}$ and not with the reactive moiety $R_x$ of the original functionalized surface.

In some embodiments, the reaction of the first modifying reagent and the reaction of the second modifying reagent with the surface may occur at random locations upon the surface. In other embodiments, the reaction of the first modifying reagent may occurs within a first region of the surface and reaction of the second modifying reagent may occur within a second regions of the surface abutting the first region. For example, the surfaces within the channel of the microfluidic device may be selectively modified with a first surface modification and the surfaces within the sequestration pen, which abut the surfaces within the channel, may be selectively modified with a second, different surface modification.

In yet other embodiments, the reaction of the first modifying reagent may occurs within a plurality of first regions separated from each other on the at least one surface, and the reaction of the second modifying reaction may occur at a second region surrounding the plurality of first regions separated from each other.

In various embodiments, modification of one or more surfaces of the microfluidic device to introduce a combination of a first surface modification and a second surface modification may be performed after the microfluidic device has been assembled. For one nonlimiting example, the first and second surface modification may be introduced by chemical vapor deposition after assembly of the microfluidic device. In another nonlimiting example, a functionalized surface having a first surface modification having a first reactive moiety and a second surface modification having a second, orthogonal reactive moiety may be introduced. Differential conversion to two different surface modifying ligands having two different surface contact moieties can follow. In another embodiment, the microfluidic device may have a single functionalized surface of Formula XXX, Formula V or Formula VII, which may be differentially modified by a mixture of two surface modifying reagents, or a mixture of a surface modifying reagent and a secondary functionalizing reagent (followed by conversion of the secondary functionalized surface to a surface modifying ligand having a second, different surface contact moiety.

In some embodiments, at least one of the combination of first and second surface modification may be performed before assembly of the microfluidic device. In some embodiments, modifying the at least one surface may be performed after assembly of the microfluidic device.

In some embodiments, the method of preparing a microfluidic device includes forming a first modified surface of one of the base or the cover before assembly of the microfluidic device; assembling the microfluidic device, wherein assembling comprises assembling the first covalently modified surface of one of the base or the cover with the microfluidic circuit materials and the other unmodified one of the cover or base; and forming a second modified surface on an unmodified surface of the assembled microfluidic device. For example, a first surface modification may be introduced on portions of the cover of the microfluidic device, before assembly, and there may be unreacted portions of the cover still remaining. The microfluidic device may be assembled, and then reacted with a second surface modification (e.g., a surface modifying compound of Formula XXXII, Formula I, Formula II, Formula III) which not only reacts with all of the unmodified regions remaining on the inner surface of the cover, but also reacts with all of the remaining interior surfaces of the base and microfluidic circuit materials.

In some embodiments, the covalently modified surface has a combination of: a functionalized surface of Formula XXX, Formula V or Formula VII; and first covalently modified surface of Formula XXXI, Formula VIII or Formula IX disposed therein. The method may further include reacting the functionalized surface of Formula XXX, Formula V or Formula VII with a secondary functionalizing reagent of Formula XXXIV:

$$RP\text{-}L_{fm}\text{-}R_{x2}$$ Formula XXXIV,

In the presence of the first covalently modified surface of Formula XXXI, Formula VIII or Formula IX, and producing a secondary functionalized surface of Formula XXX. The method may further include reacting the secondary functionalized surface of Formula XXX, with a surface modifying reagent, having a structure of Formula XII, thereby producing a second covalently modified surface of Formula XXXI, Formula VIII or Formula IX in the presence of the first covalently modified surface of Formula XXXI, Formula VIII or Formula IX.

Alternatively, the method may further include reacting the first formed functionalized surface of Formula XXX, Formula V or Formula VII with a surface modifying reagent, having a structure of Formula XII, thereby producing a second covalently modified surface of Formula XXXI, Formula VIII or Formula IX in the presence of the first covalently modified surface of Formula XXXI, Formula VIII or Formula IX.

Uses.

Materials, devices and/or apparatuses having one or more surfaces suitable for modification to introduce a surface having a structure of Formula XXXI, Formula VIII or Formula IX, as described above, may include but are not limited to flow cytometry cells, apheresis centrifugation equipment, tubing and receiving containers; or microfluidic devices handling cells, cell fragments, proteins, or nucleic acids for any kind of bioanalytical process or biomaterial sorting processes. Surfaces having a structure of Formula XXXI, Formula VIII or Formula IX are not limited to micro-scale materials, devices and/or apparatuses, but may be used for macroscale bioproduction equipment, medical devices, or water purification equipment and analytical instrumentation thereof, for a few non-limiting examples.

Methods of Loading.

Loading of biological micro-objects or micro-objects such as, but not limited to, beads, can involve the use of fluid flow, gravity, a dielectrophoresis (DEP) force, electrowetting, a magnetic force, or any combination thereof as described herein. The DEP force can be generated optically, such as by an optoelectronic tweezers (OET) configuration and/or electrically, such as by activation of electrodes/electrode regions in a temporal/spatial pattern. Similarly, electrowetting force may be provided optically, such as by an opto-electro wetting (OEW) configuration and/or electrically, such as by activation of electrodes/electrode regions in a temporal spatial pattern.

Microfluidic Devices and Systems for Operating and Observing Such Devices.

FIG. 1A illustrates an example of a microfluidic device 100 and a system 150 which can be used for maintaining, isolating, assaying or culturing biological micro-objects. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings in fluidic communication with flow path 106. In some embodiments of the device of FIG. 1A, the sequestration pens may have only a single opening in fluidic communication with the flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device (incorporated within imaging module 164, and not explicitly illustrated in FIG. 1A), and a tilting device (part of tilting module 166, and not explicitly illustrated in FIG. 1A).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 (part of imaging module 164, discussed below) can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3B, the imaging device 194 may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can comprise a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, fluid flow, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful for maintaining, isolating, assaying or culturing biological micro-objects. In some embodiments, the microfluidic circuit 120 comprises a plurality of identical microfluidic sequestration pens.

In the embodiment illustrated in FIG. 1A, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens is configured (e.g., relative to a channel 122) such that the sequestration pens can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the microfluidic channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
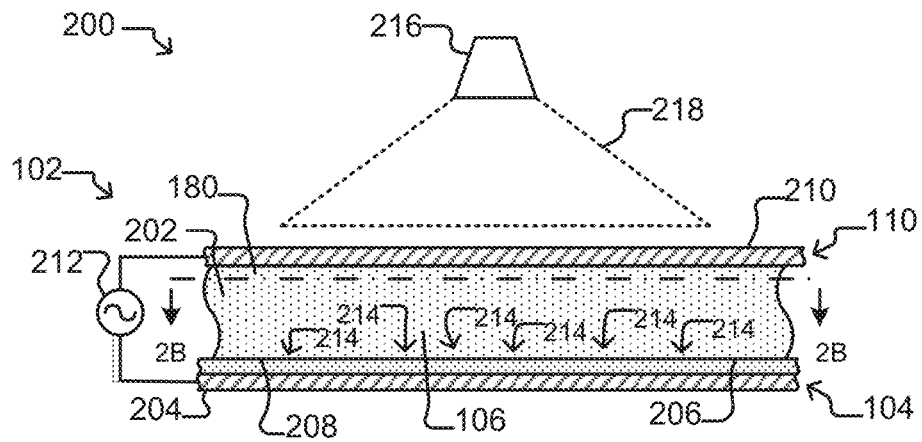
FIGS. 1B and 1C illustrate a microfluidic device according to some embodiments of the disclosure.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Examples of microfluidic devices having pens in which biological micro-objects can be placed, cultured, and/or monitored have been described, for example, in US 2014/0116881 (application Ser. No. 14/060,117, filed Oct. 22, 2013), US 2015/0151298 (application Ser. No. 14/520,568, filed Oct. 22, 2014), and US 2015/0165436 (application Ser. No. 14/521,447, filed Oct. 22, 2014), each of which is incorporated herein by reference in its entirety. U.S. application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electro wetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

Microfluidic Device Motive Configurations.

As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
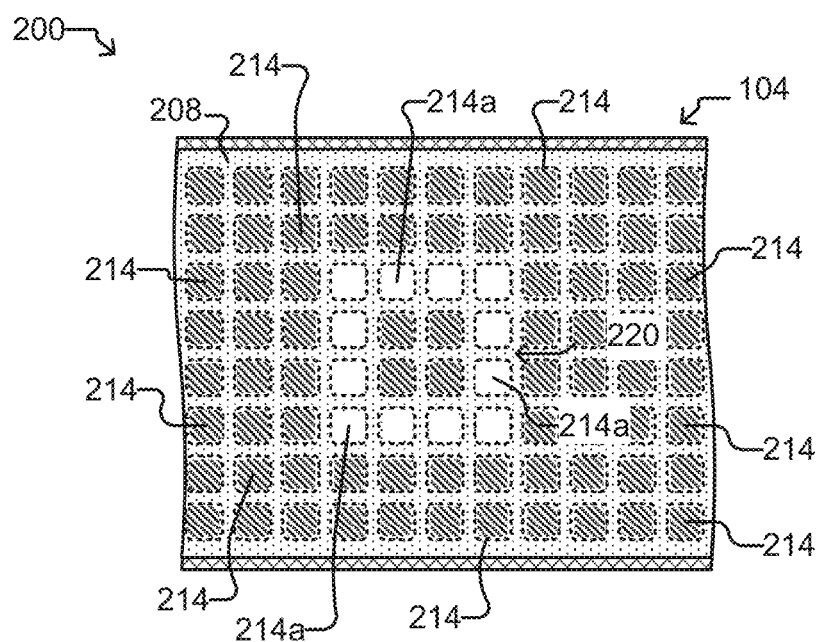

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having a region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 μm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration Pens.

Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can comprise a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the microfluidic channel 122.

The sequestration pens 224, 226, and 228 of FIGS. 2A-2C each have a single opening which opens directly to the microfluidic channel 122. The opening of the sequestration pen opens laterally from the microfluidic channel 122. The electrode activation substrate 206 underlays both the microfluidic channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be less than about 3%, 2%, 1%. 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 230, 250, 280, 290 described herein.

The microfluidic channel 122 can thus be an example of a swept region, and the isolation regions 240 of the sequestration pens 224, 226, 228 can be examples of unswept regions. As noted, the microfluidic channel 122 and sequestration pens 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration pen 224 according to the present disclosure. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration pen 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the microfluidic channel 122 does not exceed the maximum velocity $V_{max}$, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed $V_{max}$, the flow 242 of fluidic medium 180 in the microfluidic channel 122 will not move miscellaneous particles (e.g., microparticles and/or nanoparticles) from the microfluidic channel 122 into the isolation region 240 of a sequestration pen 224. Having the length $L_{con}$ of the connection region 236 be greater than the maximum penetration depth $D_p$ of the secondary flow 244 can thus prevent contamination of one sequestration pen 224 with miscellaneous particles from the microfluidic channel 122 or another sequestration pen (e.g., sequestration pens 226, 228 in FIG. 2D).

Because the microfluidic channel 122 and the connection regions 236 of the sequestration pens 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth $D_p$ of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width $W_{con}$ (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration pens 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration pens 224, 226, 228 can be in other orientations with respect to each other.

As illustrated in FIG. 2C, the width $W_{con}$ of the connection region 236 can be uniform from the proximal opening 234 to the distal opening 238. The width $W_{con}$ of the connection region 236 at the distal opening 238 can thus be any of the values identified herein for the width $W_{con}$ of the connection region 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be any of the values identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234. Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 280, 290. Likewise, the microfluidic device 250 is another variant of the microfluidic device 100, and may also have the same or a different DEP configuration as the above-described microfluidic device 100, 200, 230, 280, 290, as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the microfluidic channel 264 can move from the microfluidic channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles of: about 30° to about 90°, about 45° to about 90°, about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1 \times 10^6$, $2 \times 10^6$, $4 \times 10^6$, $6 \times 10^6$ cubic microns, or more.

In various embodiments of sequestration pens, the width $W_{ch}$ of the microfluidic channel (e.g., 122) at a proximal opening (e.g. 234) can be about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, or 100-120 microns. In some other embodiments, the width $W_{ch}$ of the microfluidic channel (e.g., 122) at a proximal opening (e.g. 234) can be about 200-800 microns, 200-700 microns, or 200-600 microns. The foregoing are examples only, and the width $W_{ch}$ of the microfluidic channel 122 can be any width within any of the endpoints listed above. Moreover, the $W_{ch}$ of the microfluidic channel 122 can be selected to be in any of these widths in regions of the microfluidic channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1\times10^4$-$3\times10^6$ square microns, $2\times10^4$-$2\times10^6$ square microns, $4\times10^4$-$1\times10^6$ square microns, $2\times10^4$-$5\times10^5$ square microns, $2\times10^4$-$1\times10^5$ square microns or about $2\times10^5$-$2\times10^6$ square microns.

In various embodiments of sequestration pens, the height $H_{ch}$ of the microfluidic channel (e.g., 122) at a proximal opening (e.g., 234) can be a height within any of the following heights: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be a height within any of the endpoints listed above. The height $H_{ch}$ of the microfluidic channel 122 can be selected to be in any of these heights in regions of the microfluidic channel other than at a proximal opening of a sequestration pen.

In various embodiments of sequestration pens a cross-sectional area of the microfluidic channel (e.g., 122) at a proximal opening (e.g., 234) can be about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be any area within any of the endpoints listed above.

In various embodiments of sequestration pens, the length $L_{con}$ of the connection region (e.g., 236) can be about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) can be in any length within any of the endpoints listed above.

In various embodiments of sequestration pens the width $W_{con}$ of a connection region (e.g., 236) at a proximal opening (e.g., 234) can be about 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, or 80-100 microns. The foregoing are examples only, and the width $W_{con}$ of a connection region (e.g., 236) at a proximal opening (e.g., 234) can be different than the foregoing examples (e.g., any value within any of the endpoints listed above).

In various embodiments of sequestration pens, the width $W_{con}$ of a connection region (e.g., 236) at a proximal opening (e.g., 234) can be at least as large as the largest dimension of a micro-object (e.g., biological cell which may be a T cell, or B cell) that the sequestration pen is intended for. The foregoing are examples only, and the width $W_{con}$ of a connection region (e.g., 236) at a proximal opening (e.g., 234) can be different than the foregoing examples (e.g., a width within any of the endpoints listed above).

In various embodiments of sequestration pens, the width $W_{pr}$ of a proximal opening of a connection region may be at least as large as the largest dimension of a micro-object (e.g., a biological micro-object such as a cell) that the sequestration pen is intended for. For example, the width $W_{pr}$ may be about 50 microns, about 60 microns, about 100 microns, about 200 microns, about 300 microns or may be about 50-300 microns, about 50-200 microns, about 50-100 microns, about 75-150 microns, about 75-100 microns, or about 200-300 microns.

In various embodiments of sequestration pens, a ratio of the length $L_{con}$ of a connection region (e.g., 236) to a width $W_{con}$ of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 236 to a width $W_{con}$ of the connection region 236 at the proximal opening 234 can be different than the foregoing examples.

In various embodiments of microfluidic devices 100, 200, 23, 250, 280, 290, $V_{max}$ can be set around 0.2, 0.5, 0.7, 1.0, 1.3, 1.5, 2.0, 2.5, 3.0, 3.5, 4.0, 4.5, 5.0, 5.5, 6.0, 6.7, 7.0, 7.5, 8.0, 8.5, 9.0, 10, 11, 12, 13, 14, or 15 microliters/sec.

In various embodiments of microfluidic devices having sequestration pens, the volume of an isolation region (e.g., 240) of a sequestration pen can be, for example, at least $5\times10^5$, $8\times10^5$, $1\times10^6$, $2\times10^6$, $4\times10^6$, $6\times10^6$, $8\times10^6$, $1\times10^7$, $5\times10^7$, $1\times10^8$, $5\times10^8$, or $8\times10^8$ cubic microns, or more. In various embodiments of microfluidic devices having sequestration pens, the volume of a sequestration pen may be about $5\times10^5$, $6\times10^5$, $8\times10^5$, $1\times10^6$, $2\times10^6$, $4\times10^6$, $8\times10^6$, $1\times10^7$, $3\times10^7$, $5\times10^7$, or about $8\times10^7$ cubic microns, or more. In some other embodiments, the volume of a sequestration pen may be about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, about 1000 to about 3500 sequestration pens, about 3000 to about 7000 sequestration pens, about 5000 to about 10,000 sequestration pens, about 9,000 to about 15,000 sequestration pens, or about 12,000 to about 20,000 sequestration pens. The sequestration pens need not all be the same size and may include a variety of configurations (e.g., different widths, different features within the sequestration pen).

FIG. 2G illustrates a microfluidic device 280 according to one embodiment. The microfluidic device 280 illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107, four distinct channels 122 and four distinct flow paths 106. The microfluidic device 280 further comprises a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

Figure 3A:
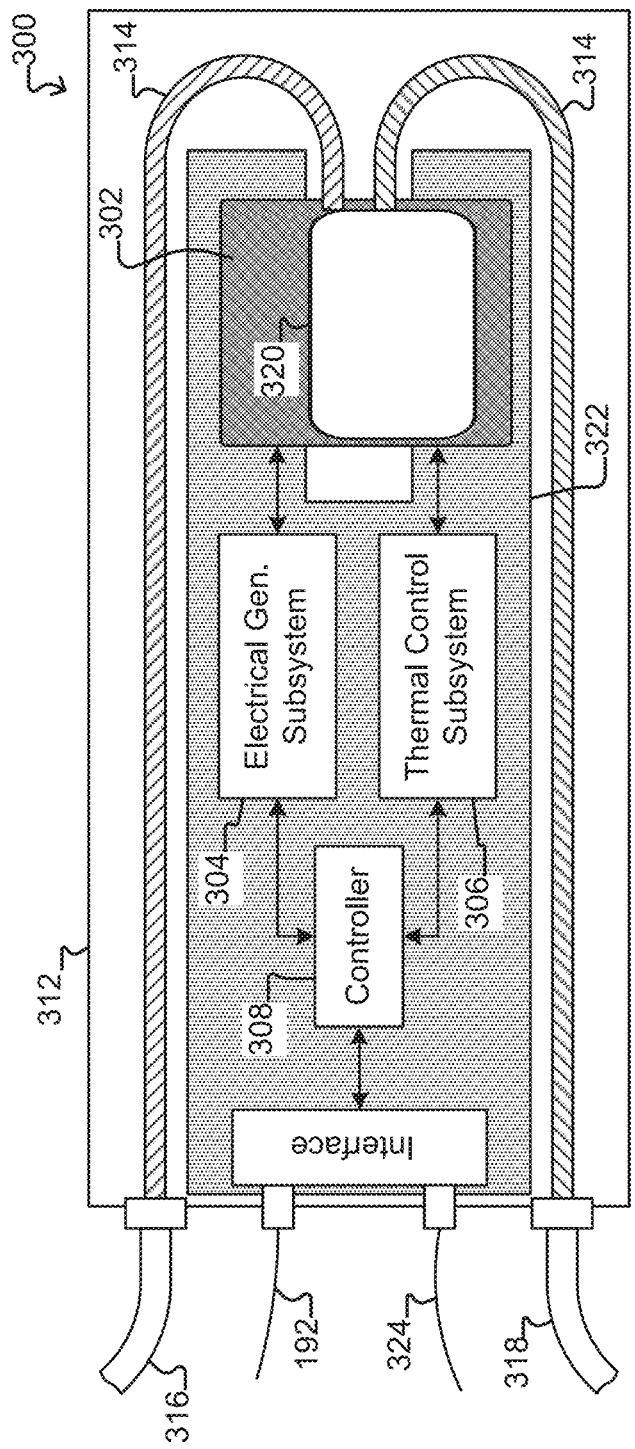
FIG. 3A illustrates a specific example of a system for use with a microfluidic device and associated control equipment according to some embodiments of the disclosure.
Figure 3B:
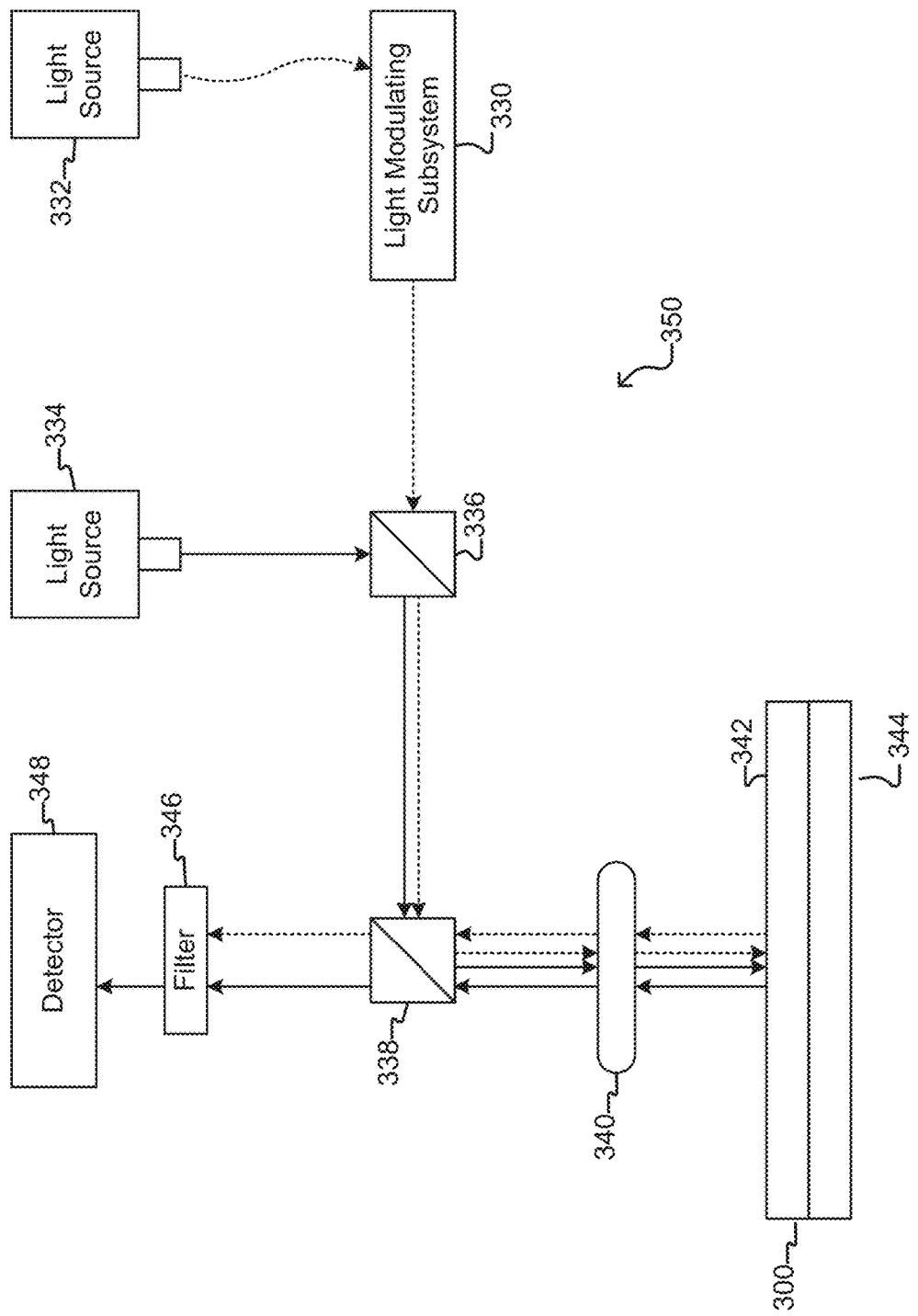
FIG. 3B illustrates an imaging device according to some embodiments of the disclosure.

FIGS. 3A through 3B shows various embodiments of system 150 which can be used to operate and observe microfluidic devices (e.g. 100, 200, 230, 250, 280, 290) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electrokinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient +/−0.02 ppm/C0) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310 (not shown). In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. In certain embodiments, imaging module 164 and/or motive module 162 of system 150 can control the light modulating subsystem 330.

In certain embodiments, the imaging device 194 further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, imaging device 194 is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region. In other embodiments, the second light source 334 may additionally or alternatively include a laser, which may have any suitable wavelength of light. The representation of the optical system shown in FIG. 3B is a schematic representation only, and the optical system may include additional filters, notch filters, lenses and the like. When the second light source 334 includes one or more light source(s) for brightfield and/or fluorescent excitation, as well as laser illumination the physical arrangement of the light source(s) may vary from that shown in FIG. 3B, and the laser illumination may be introduced at any suitable physical location within the optical system. The schematic locations of light source 334 and light source 332/light modulating subsystem 330 may be interchanged as well.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

Coating Solutions and Coating Agents.

Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Coating Agent/Solution.

Any convenient coating agent/coating solution can be used, including but not limited to: serum or serum factors, bovine serum albumin (BSA), polymers, detergents, enzymes, and any combination thereof.

Polymer-Based Coating Materials.

The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3 kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present in a concentration from about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present in a concentration of about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

In addition, in embodiments in which a covalently modified surface is used in conjunction with coating agents, the anions, cations, and/or zwitterions of the covalently modified surface can form ionic bonds with the charged portions of non-covalent coating agents (e.g. proteins in solution) that are present in a fluidic medium (e.g. a coating solution) in the enclosure.

Further details of appropriate coating treatments and modifications may be found at U.S. application Ser. No. 15/135,707, filed on Apr. 22, 2016, and is incorporated by reference in its entirety.

Additional System Components for Maintenance of Viability of Cells within the Sequestration Pens of the Microfluidic Device.

In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

Kits.

In various embodiments, a kit for providing a microfluidic device having at least one covalently modified surface configured to support biological cell growth, viability and/or portability includes: a microfluidic device comprising an enclosure comprising a base, a cover, and microfluidic circuit material defining a fluidic circuit therein, wherein at least one inner surface of the base, the cover and the microfluidic circuit material has a first covalently bound surface modification comprising a first linking group, and a first moiety, wherein the first moiety is a first surface contact moiety or a first reactive moiety; wherein at least one inner surface of the base, the cover and the microfluidic circuit material has a second covalently bound surface modification comprising a second linking group, and a second moiety, wherein the second moiety is a second surface contact moiety or second reactive moiety, and wherein the first linking group and the second linking group are different from each other and/or the first moiety is different from the second moiety.

The first covalently bound surface modification and the second covalently bound surface modification of the microfluidic device of the kit, may each have a structure independently selected from Formula XXX, Formula V, Formula VII, Formula XXXI, Formula VIII, and Formula IX

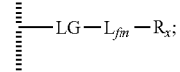

Formula XXX

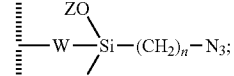

Formula V

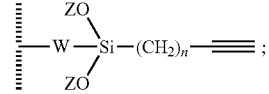

Formula VII

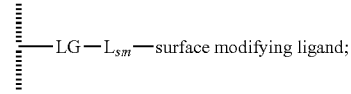

Formula XXXI

-continued

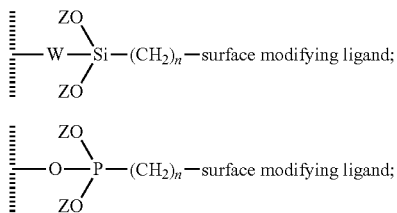
Formula VIII

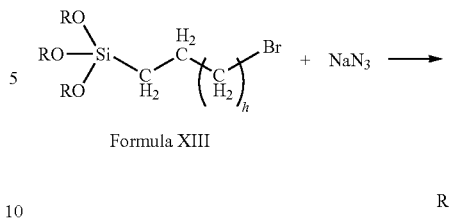
Formula XIII

Equation 2 wherein LG is —W—Si(OZ)$_2$O— or —OP(O)$_2$O—; L$_{fm}$ is a linker comprising 1 to 200 non-hydrogen atoms selected from any combination of silicon, carbon, nitrogen, oxygen, sulfur and phosphorus atoms and further comprises 0 or 1 coupling groups CG; R$_x$ is a reactive moiety; W is O, S, or N, Z is a bond to an adjacent silicon atom or is a bond to the surface; n is an integer of 3-21, L$_{sm}$ is a linker comprising 1 to 200 non-hydrogen atoms selected from any combination of silicon, carbon, nitrogen, oxygen, sulfur and phosphorus atoms and further comprises 0, 1, 2, 3, or 4 coupling groups CG; and ▮ is the surface. Kits may be provided including any microfluidic device as described herein.

The kit may further include a surface modifying reagent, which has a structure of Formula XII:

RP-L-surface contact moiety          Formula XII where RP is a reaction pair moiety; L is a linker and surface contact moiety is a moiety that provides improved contact characteristics for biological micro-objects. L is a linker; wherein L comprises a bond or 1 to 200 non-hydrogen atoms selected from any combination of silicon, carbon, nitrogen, oxygen, sulfur and phosphorus atoms, and comprises 0, 1, 2, or 3 coupling groups CG. Surface contact moiety is as defined above f. L and surface contact moiety may have any combination in the surface modifying reagent. In some embodiments, the surface contact moiety may include polyethylene glycol. In other embodiments, the surface contact moiety may include dextran. The reaction pair moiety is configured to react, respectively, with the reactive moiety of a functionalized surface.

The kit may further include a secondary functionalizing reagent having a structure of Formula XXXIV:

RP-L$_{fm}$-R$_{x2}$          Formula XXXIV wherein RP is a reaction pair moiety for reacting with the reactive moiety of Formula XXX, Formula V, or Formula VII; and L$_{fm}$ is a linker comprising 1 to 200 non-hydrogen atoms selected from any combination of silicon, carbon, nitrogen, oxygen, sulfur and phosphorus atoms and further comprises 0 or 1 coupling groups CG. R$_{x2}$ is selected to not react with the reactive moiety of the functionalized surface.

The kit may further include other reagents to be used in producing a microfluidic device having at least one covalently modified surface of Formula VIII. Suitable reaction media, buffers, or reaction accelerants may be provided in the kit. The auxiliary reagents and/or surface modifying reagent and/or secondary functionalizing reagent may be provided in separate containers.

Synthesis of the Compound of Formula IV.

A method of synthesizing a compound having a structure of Formula VI is provided, including the step of reacting a compound of Formula XIII with azide ion, and producing the compound of Formula VI as shown in Equation 2, where h is 1 to 19, n is 3 to 21, and R is H or C$_1$-C$_6$ alkyl. In some embodiments, n is an integer of 7 to 21.

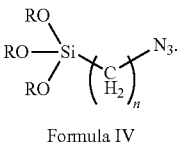
Formula IV

The azide ion may be provided as sodium azide or any other suitable source of azide ion. The reaction may be performed in any suitable solvent such as acetonitrile or DMF. The reaction may be performed at ambient temperature, which may be in a range of about 15° C. to about 30° C. In some embodiments, an ambient reaction temperature may be in a range of about 20° C. to about 30° C. In some embodiments, the reaction may be performed at a temperature selected from 30° C., 40° C., 50° C., 60° C., or 70° C. The reaction may be performed under an inert atmosphere.

In other embodiments, a compound having a structure of Formula XIII:

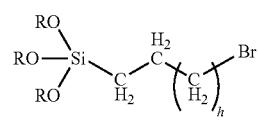
Formula XIII is provided where h is an integer of 1 to 19 and R is selected independently from the group consisting of H and C$_1$-C$_6$ alkyl. The compound of Formula II may be a useful starting material for the synthesis of the compound having a structure of Formula I. In some embodiments, h may be 5 to 19. In other embodiments, h may be 7 to 21, 8 to 21, 9 to 21, 10 to 21, 11 to 21, 12 to 21, 13 to 21, 14 to 21, 15 to 21, or 16 to 21. In other embodiments, h may be 7, 12, or 14. In some embodiments, h may be 10, 12, or 14. In some embodiments h may be 12 or 14. In various embodiments, each instance of R may be Me or Et.

Synthesis of the Compound of Formula XIII.

A method of synthesizing a compound having a structure of Formula XIII is provided including the step of: reacting an olefinic compound (compound 1) with a silane (compound 2), in the presence of a catalyst or an initiator, thereby producing the compound having a structure of Formula XIII. (See Equation 3)

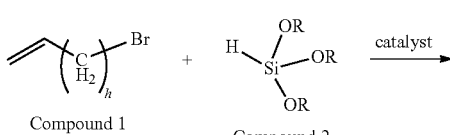

Equation 3

Compound 1      Compound 2

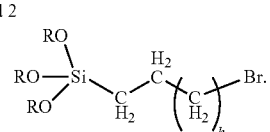
Formula XIII

For the compounds 1, 2, and Formula XIII of Equation 3, h is an integer of 1 to 19 and each instance of R is independently H or $C_1$-$C_6$ alkyl. In some embodiments, h is an integer of about 5 to 19. In some embodiments, R is $C_1$-$C_6$ alkyl.

In some embodiments, each instance of R may be selected from methyl, ethyl and propyl. In other embodiments, each instance of R may be methyl. In various embodiments, h may be 7 to 19. In other embodiments, h may be 7, 12, or 14. In some embodiments, h may be 7.

In some embodiments, the catalyst may be any suitable hydrosilylation catalyst. The catalyst may be a transition metal complex $M(L)_n$ where L is a ligand, and M is a metal such as Fe(0), Co(I), Rh(I), Ni(0), Pd(0), Pt(II) or Pt(0). In some embodiments, the metal of the hydrosilylation catalyst complex may be Co(I), Rh(I), Ni(0), Pt(II) or Pt(0). In yet other embodiments, the metal may be Rh(I), Pt(II), or Pt(0). The ligands may be selected to create an electron rich complex and may be any suitable ligand. Ligands may include halogen (e.g., chlorine); olefins, nitriles, siloxanes (including simple tetraalkyldivinyl siloxanes or constrained SILOP ligands; aromatic moieties 2,2'-bis(diphenylphosphino)-sterically constrained biphenyl or binaphthyl ligands such as BINAP, BIPHEP, BINEPINE, or PHANEPHOS; 2,3-O-isopropylidene-2,3-dihydroxy-1,4-bis(diphenylphosphino)butyl (DIOP); (Some examples of SUITABLE HYDROSILYLATION CATALYSTS CAN INCLUDE BUT ARE NOT LIMITED TO $H_2PTCL_6.6H_2O$/IPROH (SPEIER catalyst); chloro(1, 5-cyclooctadiene) Rh(1) dimer ([Rh(cod)Cl]2; Tris(triphenylphosphine)-rhodium(I) chloride; [PtCl$_2$(NCR)$_2$ where R may be N(alkyl)$_2$, particularly methyl or a cyclic amine such as N-piperidinyl, Ph, $Ch_2Ph$; Karsted's catalyst $Pt_2\{[(CH_2=CH_2)SiMe_2]O\}_3)$; and bis (imino) pyridine iron dinitrogen complexes ($^{et}$ PDI)Fe $(N_2)]_2(mu_2$-azido).

In some embodiments, the catalyst may be a platinum (0) catalyst. The platinum (0) catalyst may be a Pt(0)-1,1,3,3-tetramethyl-1,3-divinyldisiloxane complex (Cpd. 3):

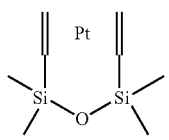

Compound 3

In other embodiments, an initiator may be used, which may be present in a range of about 0.5 equivalents to about 1.4 equivalents. In some embodiments, the initiator may be trialkylborane.

The reaction may be performed in any solvent that is capable of dissolving the olefinic compound (Cpd. 1 of Equation 2), which may include but is not limited to DMF, benzene, tetrahydrofuran, toluene, 1, 3-bis trifluoromethyl benzene, amongst other fluorinated or partially fluorinated solvents. In some embodiments, toluene or dimethyl formamide (DMF) may be used.

The reaction may be performed under an inert atmosphere, which may be argon or nitrogen gas. Typically, an inert atmosphere will exclude water vapor.

Elevated temperatures may be used to promote reaction, and the reaction may be performed at a temperature in a range of about 60° C. to about 110° C. In some embodiments, the reaction may be performed at about 60° C., 65° C., 70° C., 75° C., 80° C., 85° C., 90° C., 95° C., 100° C., 105° C., or about 110° C. The reaction may be completed after about 6 h, 10 h, 14 h, 18 h, 24 h, 30 h, 48 h, 60 h or any time point in between.

In some other embodiments, a method of synthesizing a compound having a structure of Formula IV:

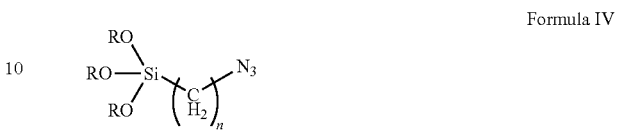

Formula IV may be provided, which includes the step of reacting a compound having a structure of Formula XIV:

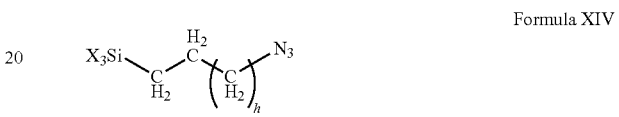

Formula XIV with an alcohol ROH, in the presence of a base, wherein h is an integer of 1 to 19; each instance of X is Cl; ROH is methyl alcohol, ethyl alcohol, or propyl alcohol, thereby producing the compound of Formula I, wherein h is an integer of 1 to 19, and R is $C_1$-$C_3$ alkyl. In some embodiments, the base may be pyridine. In some embodiments, h is an integer of 5 to 19. In various embodiments, h may be 7, 12 or 14. In yet other embodiments, R may be methyl.

Synthesis of the Compound of Formula L.

A method of synthesizing a compound having a structure of Formula L is provided, including the step of: reacting an olefinic compound (compound 1) with a silane (compound 2), in the presence of a catalyst or an initiator, thereby producing the compound having a structure of Formula L (See Equation 1).

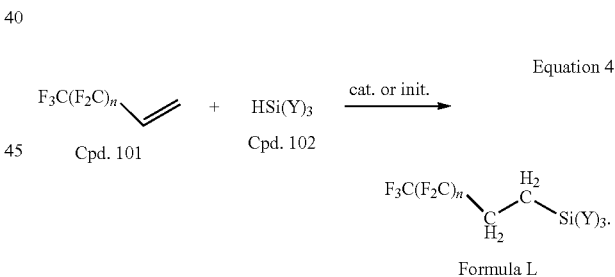

Equation 4

Formula L

For the compounds 101, 1032, and Formula L of Equation 4, n may be an integer of 13 to 25; each instance of Y may be independently halo, OH, or OR, halo is Br, Cl or F; and R is $C_1$-$C_6$ alkyl. In some embodiments, each instance of Y is Cl. In other embodiments, each instance of Y may be methoxy, ethoxy, or propoxy. In various embodiments, n may be 13, 15, 17, or 19. In some embodiments, n may be 13 or 15.

In some embodiments, the compound of Formula L may be a compound having a structure of Formula LI, and may be produced according to the method shown in Equation 5. The olefinic compound (compound 1) may be reacted with a silane having three substituents OR (compound 3) where R may be H or $C_1$ to $C_6$ alkyl. In some embodiments, each instance of R may be selected from methyl, ethyl and propyl. In other embodiments, each instance of R may be methyl. In various embodiments, n may be 13, 15, 17, or 19. In some embodiments, n may be 13 or 15.

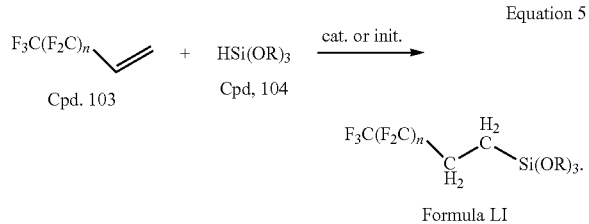

Formula LI

In other embodiments, the compound of Formula L may be a compound having a structure of Formula LII, and may be produced according to the method shown in Equation 6.

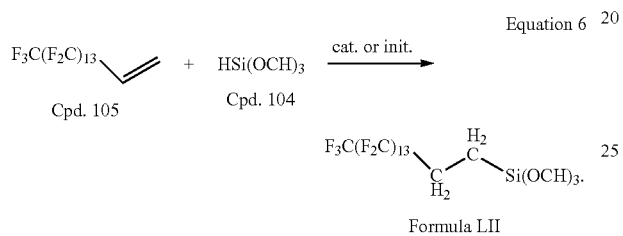

Formula LII

The olefinic compound, 3, 3, 4, 4, 5, 5, 6, 6, 7, 7, 8, 8, 9, 9, 10, 10, 11, 11, 12, 12, 13, 13, 14, 14, 15, 15, 16, 16, 16-nonacosafluorohexadec-1-ene (Cpd. 105) may be reacted with a trialkoxysilane (Cpd. 104) in the presence of a catalyst or initiator; thereby producing the molecule of Formula LII. The catalyst may be any suitable hydrosilylation catalyst.

Synthesis of the Compound of Formula VI.

The compound of Formula VI may be synthesized by various routes, one of which may include reacting the compound of Formula IV with a metal acetylide.

EXAMPLES

System and Microfluidic Device:

An OptoSelect chip, a nanofluidic device manufactured by Berkeley Lights, Inc. and controlled by an optical instrument which was also manufactured by Berkeley Lights, Inc. The instrument included: a mounting stage for the chip coupled to a temperature controller; a pump and fluid medium conditioning component; and an optical train including a camera and a structured light source suitable for activating phototransistors within the chip. The OptoSelect™ chip included a substrate configured with OptoElectroPositioning (OEP™) technology, which provides a phototransistor-activated OET force. The chip also included a plurality of microfluidic channels, each having a plurality of NanoPen™ chambers (or sequestration pens) fluidically connected thereto. The volume of each sequestration pen was around $1 \times 10^6$ cubic microns.

Priming Solution:

Complete growth medium containing 0.1% Pluronic® F127 ((Life Technologies® Cat #P6866).

Preparation for culturing: The microfluidic device having a modified surface was loaded onto the system and purged with 100% carbon dioxide at 15 psi for 5 min. Immediately following the carbon dioxide purge, the priming solution was perfused through the microfluidic device at 5 microliters/sec for 8 min. Culture medium was then flowed through the microfluidic device at 5 microliters/sec for 5 min.

Priming Regime.

250 microliters of 100% carbon dioxide was flowed in at a rate of 12 microliters/sec. This was followed by 250 microliters of PBS containing 0.1% Pluronic® F27 (Life Technologies® Cat #P6866), flowed in at 12 microliters/sec. The final step of priming included 250 microliters of PBS, flowed in at 12 microliters/sec. Introduction of the culture medium follows.

Perfusion Regime.

The perfusion method was either of the following two methods:

1. Perfuse at 0.01 microliters/sec for 2 h; perfuse at 2 microliters/sec for 64 sec; and repeat.
2. Perfuse at 0.02 microliters/sec for 100 sec; stop flow 500 sec; perfuse at 2 microliters/sec for 64 sec; and repeat.

Example 1. Synthesis of (11-bromoundecyl) trimethoxysilane (Compound 4) 1.26 g (5.4 mmol) of 11-bromoundec-1-ene (Sigma Aldrich) is solubilized in 150 ml of dry toluene (Oakwood Products) in an argon flushed reaction vessel equipped with a reflux condensor Trimethoxysilane (1.77 g, 14.5 mmol, Sigma Aldrich Cat. No. 282626) is added to the reaction under argon purging via syringe through a septum. Next, 1.5 g of hydrosilation catalyst solution, (0.08 mmol) of hydrosilation catalyst platinum (0)-1,3-divinyl-1,1,3,3-tetramethyldisiloxane complex (Compound 3, 0.1M in poly (dimethylsiloxane), Sigma Aldrich, Cat. No. 479527) is added to the reaction under argon purging via syringe. The reaction is then continued under an argon atmosphere at a temperature of 80° C. for 24 hours to produce (11-bromoundecyl) trimethyoxysilane (Compound 4). The reaction is allowed to cool to room temperature under argon, filtered, and the product is extracted into pentane and the solvent is removed by rotary evaporation at reduced pressure. The product is purified by vacuum distillation.

Example 2. Synthesis of (11-azidoundecyl)trimethoxysilane (Compound 5). (13-11-azidoundecyltrimethoxysilane was synthesized from 11-bromoundecyltrimethoxysilane (Gelest) by displacing the bromides with sodium azide. In a typical reaction, 4.00 g of 11-bromoundecyltrimethoxysilane (Gelest Cat. #SIB 1908.0) was added to a solution containing 2.00 g of sodium azide (Sigma-Aldrich) in 60 mL of dry dimethylformamide (Acros). The solution was stirred for 24 h at room temperature under nitrogen. Next, the solution was filtered, and the filtrate was extracted with dry pentane (Acros). The crude 11-azidoundecyltrimethoxysilane product was concentrated by rotary evaporation and was purified by two successive vacuum distillations and characterized using NMR and FTIR spectroscopies.

Example 3. Preparation of a Functionalized Surface of a Silicon Wafer

A silicon wafer (780 microns thick, 1 cm by 1 cm) was treated in an oxygen plasma cleaner (Nordson Asymtek) for 5 min, using 100 W power, 240 mTorr pressure and 440 sccm oxygen flow rate. The plasma treated silicon wafer was treated in a vacuum reactor with (11-azidoundecyl) trimethoxy silane (Compound 5, 300 microliters) in a foil boat in the bottom of the vacuum reactor in the presence of magnesium sulfate heptahydrate (0.5 g, Acros Cat. #10034-99-8), as a water reactant source in a separate foil boat in the bottom of the vacuum reactor. The chamber was then pumped to 750 mTorr using a vacuum pump and then sealed. The vacuum reactor was placed within an oven heated at 110° C. for 24-48 h. This introduced a modified surface to the wafer, where the functionalized surface had a structure of Formula XV:

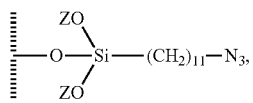

Formula XV where Z is a bond to an adjacent silicon atom bound to the surface or is a bond to the surface and ≣ is the surface. After cooling to room temperature and introducing argon to the evacuated chamber, the wafer was removed from the reactor. The wafer was rinsed with acetone, isopropanol, and dried under a stream of nitrogen. Confirmation of introduction of the functionalized surface was made by ellipsometry and contact angle goniometry.

Example 4. Modification of Microfluidic Circuit Material

One example of microfluidic circuit material is photopatternable silicone and was used to define the fluidic circuit within the microfluidic device. Proof of modification of this material was obtained. An ITO wafer having photopatterned silicone structures incorporated upon it was in an oxygen plasma cleaner (Nordson Asymtek) for 5 min, using 100 W power, 240 mTorr pressure and 440 sccm oxygen flow rate. The plasma-cleaned photopatterned ITO wafer was treated as described in Example 3 to introduce a modified surface of Formula XV onto the photopatterned silicone. FTIR ATR (attenuated total reflectance) spectra were measured using a ThermoFisher Nicolet iS50 spectrometer with a liquid nitrogen cooled MCT detector. Spectra were collected on a Harrick Vari-GATR accessory by pressing the photopatterned silicone, modified with a surface of Formula XV, against the surface of the germanium crystal with 200 N force. In pressing the modified photopatternable silicone material against the germanium crystal, FTIR ATR was obtained only of the modified photopatterned silicone. 250 scans were collected at 4 cm-1 resolution and referenced against a background spectrum of the bare Germanium crystal. Spectra were visualized using Omnic software provided with the FTIR spectrometer.

Figure 4:
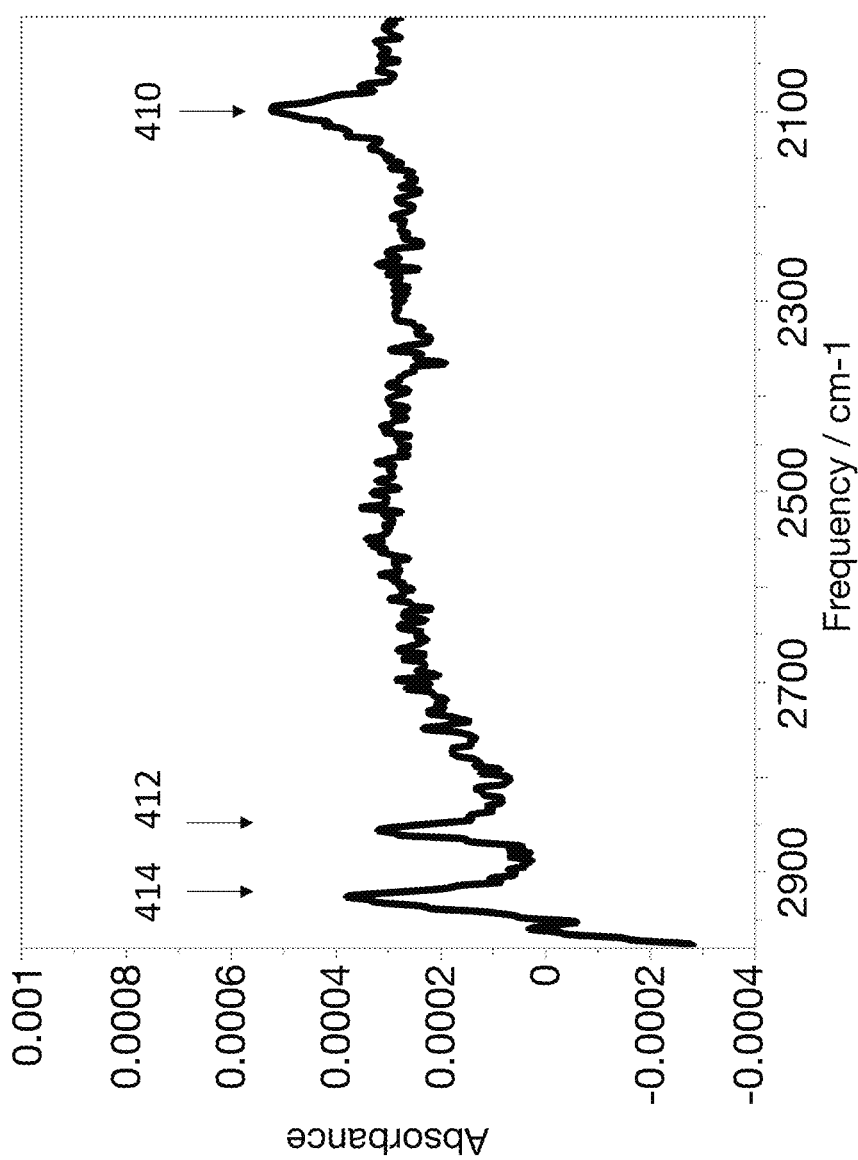
FIG. 4 is a graphical representation of a FTIR spectrum for modified microfluidic circuit material according to some embodiments of the disclosure.

As shown in FIG. 4, the peak at ~2098 cm-1 (410) is attributable to the azide asymmetric stretch. Peaks at 2924 cm-1 (414) and 2854 cm-1 (412) are attributable to C—H stretching modes Note:

In the following examples of introduction of a modified surface to a microfluidic device, the contact angle and thickness measurements were performed on silicon wafers modified in the same manner as the specific modified surface in the microfluidic device.

Example 5. Preparation of a Microfluidic Device Having Modified Interior Surfaces of Formula XV An OptoSelect device having a first silicon electrode activation substrate and a second ITO substrate on the opposite wall, and photopatterned silicone microfluidic circuit material separating the two substrates, was treated in an oxygen plasma cleaner (Nordson Asymtek) for 1 min, using 100 W power, 240 mTorr pressure and 440 sccm oxygen flow rate. The plasma treated microfluidic device was treated in a vacuum reactor with 3-azidoundecyl) trimethoxysilane (Compound 5, 300 microliters) in a foil boat in the bottom of the vacuum reactor in the presence of magnesium sulfate heptahydrate (0.5 g, Acros), as a water reactant source in a separate foil boat in the bottom of the vacuum reactor. The chamber was then pumped to 750 mTorr using a vacuum pump and then sealed. The vacuum reactor was placed within an oven heated at 110° C. for 24-48 h. This introduced a functionalized surface to all of the inner facing surfaces of the microfluidic device, where the functionalized surface had a structure of Formula XV:

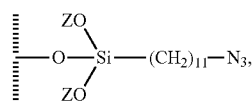

Formula XV where Z is a bond to an adjacent silicon atom bound to the surface or is a bond to the surface and ≣ is the surface. After cooling to room temperature and introducing argon to the evacuated chamber, the microfluidic device was removed from the reactor. The microfluidic device having the functionalized surface was then treated with an alkynyl species to introduce the desired modified surface as described below in Examples 6 and 7.

Example 6. Introduction of a Polyethylene Glycol (PEG) Modified Surface (Formula XVI) to a Microfluidic Device Materials. Alkyne-modified PEG (j=MW ~5000 Da) (Compound 6) was purchased from JenKem and used as received.

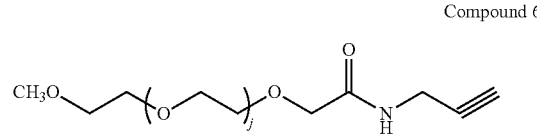

Compound 6

Sodium ascorbate and copper sulfate pentahydrate were purchased from Sigma-Aldrich and used as received. (3 [tris(3-hydroxypropyltriazolylmethyl)amine) THPTA rate accelerating ligand (Glen Research) was used as received.

The product microfluidic device from Example 5, having a surface of Formula XV, as described above, was reacted with alkyne-modified PEG (Compound 5) by flowing at least 250 microliters of an aqueous solution containing 3.3 millimolar alkyne-modified PEG, 50 millimolar copper sulfate, 55 millimolar THPTA ligand and 100 millimolar sodium ascorbate through the microfluidic devices having the 11-azidoundecylsiloxy surface modifying ligand. The reaction was allowed to proceed at room temperature for at least 1 hour. The microfluidic device having a PEG modified surface of Formula XVI:

Formula XVI

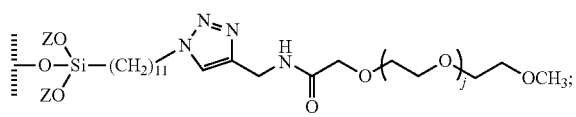

where Z is as defined above for Formula VIII, and ≡ is the surface, was then rinsed by flowing at least 250 microliters of deionized water through the devices. After completion of the cyclization reaction that introduces the modified surface, the thickness of the layer increased from 1.4 nm (functionalized surface thickness) to 5 nm in thickness. Additionally, the sessile drop water contact angle decreased from approximately 80 degrees (functionalized surface of Formula XV) to 35 degrees (surface of Formula XVI).

Example 7. Introduction of a Dextran Modified Surface (Formula XVII) to a Microfluidic Device The product microfluidic device from Example 5, having a surface of Formula XV as described above, was treated with dibenzylcyclooctynyl (DBCO) modified-dextran, weight averaged molecular weight 3000 Da (Compound 7, Nanocs):

Compound 7

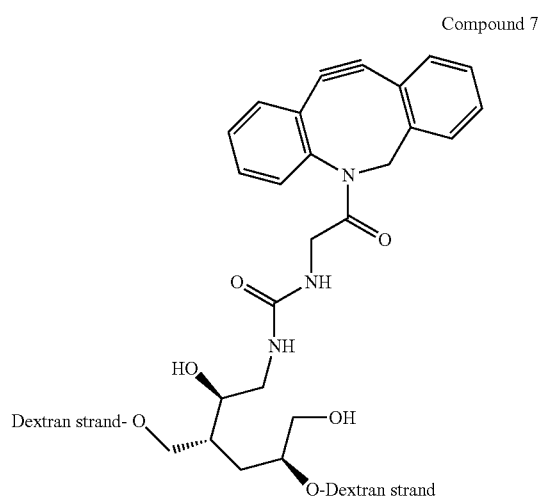

by flowing at least 250 microliters of an aqueous solution containing 1.66 millimolar DBCO-dextran through the microfluidic devices having surface modifying azide ligands after vapor deposition. The reaction was allowed to proceed at room temperature for at least 1 h. The microfluidic device having a modified surface of Formula XVII (one of two regioisomers shown):

Formula XVII

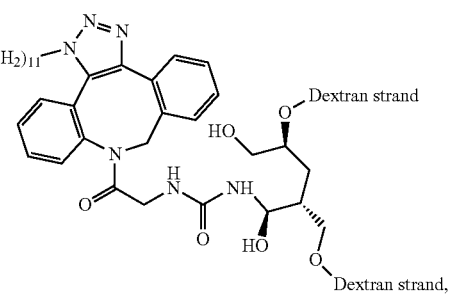

where Z is as defined above for Formula VIII, and ≡ is the surface, was then rinsed by flowing at least 250 microliters of DI water through the chips.

Example 8. Alternative Introduction of a Polyethylene Glycol (PEG) Modified Surface (Formula XVIII) to a Microfluidic Device The product microfluidic device from Example 5, having a surface of Formula XV as described above, was treated with dibenzylcyclooctynyl (DBCO) modified-PEG, weight averaged molecular weight 5000 Da (Compound 8, Broadpharm, Cat. #BP-22461) by flowing at least 250 microliters of an aqueous solution containing 1.33 millimolar DBCO-PEG through the microfluidic device having surface modifying azide ligands after vapor deposition. The reaction was allowed to proceed at 40° C. for at least 1 h. The microfluidic device having a modified surface of Formula XVIII was then rinsed by flowing at least 250 microliters of DI water through the chips. One of two regioisomers shown.

Formula XVIII

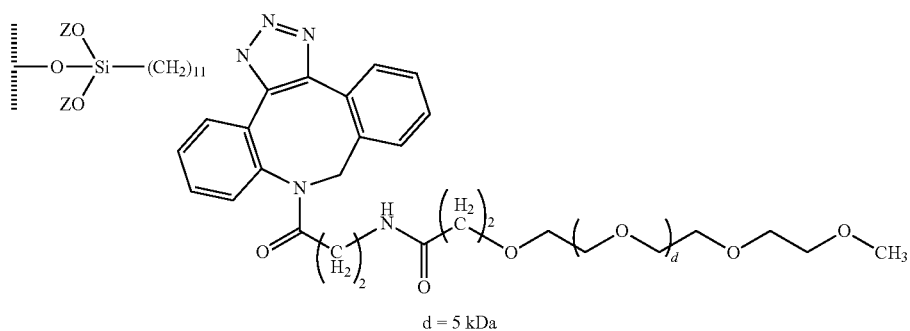

d = 5 kDa

Example 9. Introduction of a Poly-L-Glutamic Acid (PGA) Modified Surface (Formula XIX) to a Microfluidic Device The product microfluidic device from Example 5, having a surface of Formula XV, as described above, was reacted with alkyne-modified poly (L-glutamic acid/salt)(PGA, MW=15,000 Da)(Compound 8, Alamanda™ Polymers, Cat. #AK-PLE100):

Formula XIX

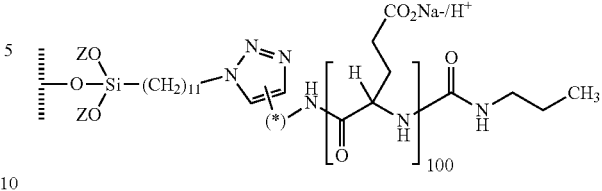

Compound 8

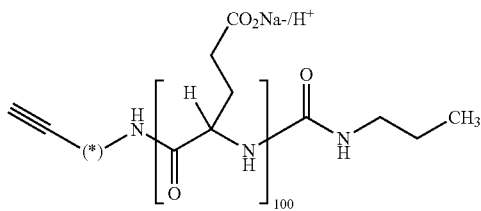

(where (*) is a proprietary linker) by flowing at least 250 microliters of a buffered saline solution (5.4×PBS pH 7.4) containing 1.33 millimolar alkyne-modified PGA, 500 micromolar copper sulfate, 550 micromolar THPTA ligand and 5 millimolar sodium ascorbate through the microfluidic devices having the 11-azidoundecylsiloxy surface modifying ligand. The reaction was allowed to proceed at room temperature for at least 1 hour or 40° C. for at least 15 minutes. The microfluidic device having a PGA modified surface of Formula XIV was then rinsed by flowing at least 250 microliters of deionized water through the devices. After completion of the cyclization reaction that introduces the modified surface, the thickness of the layer increased from 1.1 nm (functionalized surface thickness) to 5.2 nm in thickness. Additionally, the sessile drop water contact angle decreased from approximately 80 degrees (functionalized surface of Formula X) to 17 degrees (surface of Formula XIX).

Example 10. Introduction of a Covalently Modified Surface of Biotin Functionalized PEG Surface (Formula XX) to a Microfluidic Device The product microfluidic device from Example 5, having a surface of Formula XV, as described above, was reacted with biotin functionalized alkynyl PEG (PEG is 1 kDA, Compound 9, Nanocs, Cat. #PG2-AKBN-1k):

Compound 9 by flowing at least 250 microliters of an aqueous solution containing 31.33 millimolar Compound 9, 500 micromolar copper sulfate, 550 micromolar THPTA ligand and 5 millimolar sodium ascorbate through the microfluidic devices having the 11-azidoundecylsiloxy surface modifying ligand (Formula XV). The reaction was allowed to proceed at room temperature for at least 1 hour. The microfluidic device having a biotinylated PEG modified surface of Formula XX Formula XX

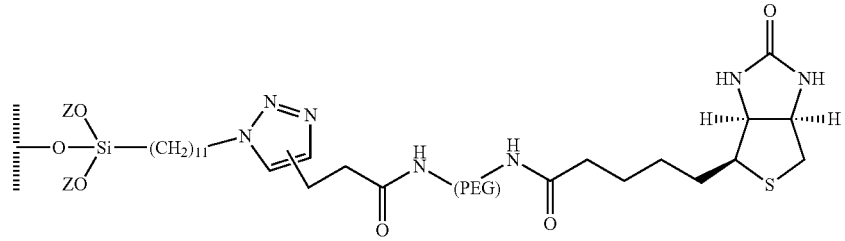

was then rinsed by flowing at least 250 microliters of deionized water through the devices. After completion of the cyclization reaction that introduces the modified surface, the thickness of the layer increased from 1.4 nm (functionalized surface thickness) to 5 nm in thickness. Additionally, the sessile drop water contact angle decreased from approximately 80 degrees (functionalized surface of Formula XV) to 39 degrees (surface of Formula XX).

Example 11. Introduction of a Covalently Modified Surface of Photocleavable Biotin Functionalized PEG Surface (Formula XXI) to a Microfluidic Device The product microfluidic device from Example 5, having a surface of Formula XV, as described above, was reacted with biotin functionalized photocleavable alkyne PEG3 (Compound 10, Broadpharm, Cat. #BP-22677, which contains the photocleavable nitro substituted phenyl group as part of the linker L), flowing at least 250 microliters of an aqueous solution containing 1.33 millimolar Compound 10, 500 micromolar copper sulfate, 550 micromolar THPTA ligand and 5 millimolar sodium ascorbate through the microfluidic devices having the 11-azidoundecylsiloxy surface modifying ligand. The reaction was allowed to proceed at room temperature for at least 1 hour. The microfluidic device having a biotinylated PEG modified surface of Formula XX1:

tion was allowed to proceed at room temperature for at least 1 hour or 40° C. for at least 15 minutes. The microfluidic device having a carboxylic acid modified surface of Formula XXII was then rinsed by flowing at least 250 microliters of deionized water through the devices. After completion of the cyclization reaction that introduces the modified surface, the thickness of the layer increased from 1.1 nm (functionalized surface thickness) to 2 nm in thickness. Additionally, the sessile drop water contact angle decreased from approximately 80 degrees (functionalized surface of Formula XV) to 64 degrees (surface of Formula XXII).

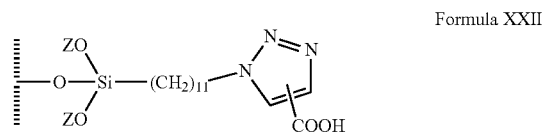

Formula XXII

Example 13. Introduction of an Amine Modified Surface (Formula XXIII) to a Microfluidic Device The product microfluidic device from Example 5, having a surface of Formula XV, as described above, was reacted with propargyl amine (HC≡CCH₂NH₂, Sigma Aldrich, Cat. #P50900-5G) by flowing at least 250 microliters of a buff- Formula XXI

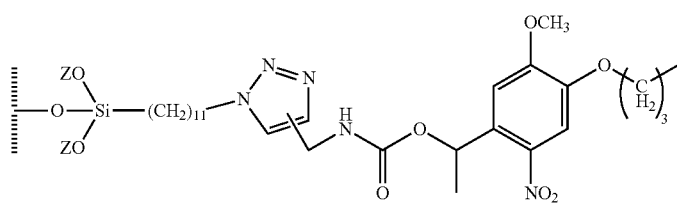

was then rinsed by flowing at least 250 microliters of deionized water through the devices. After completion of the cyclization reaction that introduces the modified surface, the thickness of the layer increased from 1.4 nm (functionalized surface thickness) to approx. 5 nm in thickness. Additionally, the sessile drop water contact angle decreased from approximately 80 degrees (functionalized surface of Formula XV) to 42 degrees (surface of Formula XXI).

Example 12. Introduction of a Propiolic Acid Modified Surface (Formula XXII) to a Microfluidic Device The product microfluidic device from Example 5, having a surface of Formula XV, as described above, was reacted with propiolic acid (HC≡CCO2H, Sigma Aldrich, Cat. #P51400-5G) by flowing at least 250 microliters of a buffered saline solution (5.4×PBS pH 7.4) containing 1.33 millimolar propiolic acid, 500 micromolar copper sulfate, 550 micromolar THPTA ligand and 5 millimolar sodium ascorbate through the microfluidic devices having the 11-azidoundecylsiloxy surface modifying ligand. The reacered saline solution (5.4×PBS pH 7.4) containing 1.33 millimolar propargylamine, 500 micromolar copper sulfate, 550 micromolar THPTA ligand and 5 millimolar sodium ascorbate through the microfluidic devices having the 11-azidoundecylsiloxy surface modifying ligand. The reaction was allowed to proceed at room temperature for at least 1 hour or 40° C. for at least 15 minutes. The microfluidic device having a amine modified surface of Formula XXIII was then rinsed by flowing at least 250 microliters of deionized water through the devices.

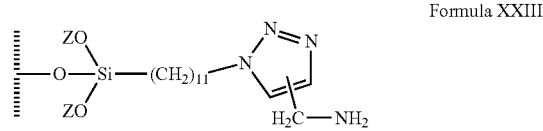

Formula XXIII

Example 14. Introduction of a PEG Carboxylic Acid Modified Surface (Formula XXIV) to a Microfluidic Device The product microfluidic device from Example 5, having a surface of Formula XV, as described above, was reacted with Alkyne PEG acid (PEG (f=5000 Da, Compound 11) Nanocs, Cat. #PG2-AKCA-5k) by flowing at least 250 microliters of a buffered saline solution (5.4×PBS pH 7.4) containing 1.33 millimolar Compound 11, 500 micromolar copper sulfate, 550 micromolar THPTA ligand and 5 millimolar sodium ascorbate through the microfluidic devices having the 11-azidoundecylsiloxy surface modifying ligand. The reaction was allowed to proceed at room temperature for at least 1 hour or 40° C. for at least 15 minutes. The microfluidic device having a carboxylic acid modified surface of Formula XXIV was then rinsed by flowing at least 250 microliters of deionized water through the devices. After completion of the cyclization reaction that introduces the modified surface, the thickness of the layer increased from 1.1 nm (functionalized surface thickness) to 5 nm in thickness. Additionally, the sessile drop water contact angle decreased from approximately 80 degrees (functionalized surface of Formula XV) to 48 degrees (surface of Formula XXIV).

Formula XXIV

Example 15. Introduction of a Poly Lysine Modified Surface (Formula XXV) to a Microfluidic Device The product microfluidic device from Example 5, having a surface of Formula XV, as described above, was reacted with poly(lysine hydrobromide)graft -(4 pentynamide, Compound 12, PLKB100-g-AK20Alamanda Polymers, Cat. #PLKB100-g-AK20, 100 lysine repeat units, 20% alkynylated, MW 21,000 Da) by flowing at least 250 microliters of a buffered saline solution (5.4×PBS pH 7.4) containing 1.33 millimolar Compound 12, 500 micromolar copper sulfate, 550 micromolar THPTA ligand and 5 millimolar sodium ascorbate through the microfluidic devices having the 11-azidoundecylsiloxy surface modifying ligand. The reaction was allowed to proceed at room temperature for at least 1 hour or 40° C. for at least 15 minutes. The microfluidic device having an amine modified surface of Formula XXV was then rinsed by flowing at least 250 microliters of deionized water through the devices. After completion of the cyclization reaction that introduces the modified surface, the thickness of the layer increased from 1.1 nm (functionalized surface thickness) to approx. 3 nm in thickness. Additionally, the sessile drop water contact angle decreased from approximately 80 degrees (functionalized surface of Formula XV) to 50 degrees (surface of Formula XXV).

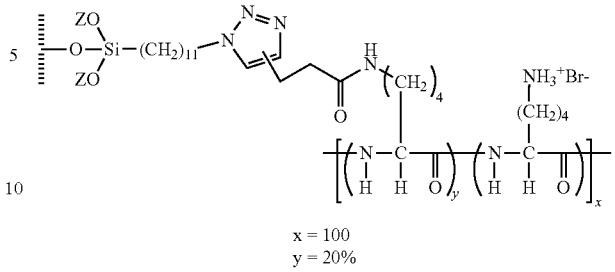

Formula XXV x = 100
y = 20%

Example 16. Introduction of a Poly Glutamic Acid Modified Surface (Formula XXVI) to a Microfluidic Device The product microfluidic device from Example 5, having a surface of Formula XV, as described above, was reacted with poly(glutamic acid)graft —(N-propargyl), Compound 13, Alamanda Polymers, Cat. #PLE100-g-AK20, 20% alkynylated, 100 glutamic acid repeats, MW 15,000 Da) by flowing at least 250 microliters of a buffered saline solution (5.4×PBS pH 7.4) containing 1.33 millimolar Compound 13, 500 micromolar copper sulfate, 550 micromolar THPTA ligand and 5 millimolar sodium ascorbate through the microfluidic devices having the 11-azidoundecylsiloxy surface modifying ligand. The reaction was allowed to proceed at room temperature for at least 1 hour or 40° C. for at least 15 minutes. The microfluidic device having a carboxylic acid modified surface of Formula XXVI was then rinsed by flowing at least 250 microliters of deionized water through the devices. After completion of the cyclization reaction that introduces the modified surface, the thickness of the layer increased from 1.1 nm (functionalized surface thickness) to approx. 3 nm in thickness. Additionally, the sessile drop water contact angle decreased from approximately 80 degrees (functionalized surface of Formula XV) to 54 degrees (surface of Formula XXVI).

Formula XXVI x = 100
y = 20%

Example 17. Introduction of a Biotinylated Polyethylene Glycol (PEG) Modified Surface with a Disulfide Cleavable Linker (Formula XXVII) to a Microfluidic Device The product microfluidic device from Example 5, having a surface of Formula XV as described above, was treated with dibenzylcyclooctynyl (DBCO)S—S biotin modified-PEG3, Compound 14, Broadpharm, Cat. #BP-22453) by flowing at least 250 microliters of an aqueous solution containing 1.33 micromolar Compound 14 through the microfluidic device having surface modifying azide ligands after vapor deposition. The reaction was allowed to proceed at 40° C. for at least 1 h. The microfluidic device having a modified surface of Formula XXVII was then rinsed by flowing at least 250 microliters of DI water through the chips. One of two regioisomers shown.

substrate on the opposite wall, and photopatterned silicone microfluidic circuit material separating the two substrates, was treated in an oxygen plasma cleaner (Nordson Asymtek) for 1 min, using 100 W power, 240 mTorr pressure and 440 sccm oxygen flow rate. The plasma treated microfluidic device was treated in a vacuum reactor with methoxytriethyleneoxypropyl trimethoxysilane (Compound 16, Gelest Catalog #SIM6493.4, 300 microliters) in a foil boat in the Formula XXVII

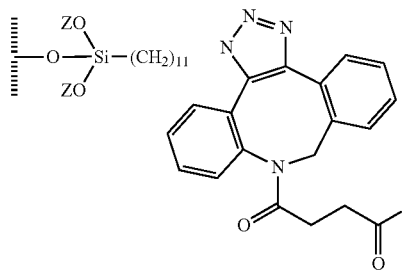

After completion of the cyclization reaction that introduces the modified surface, the thickness of the layer increased from 1.1 nm (functionalized surface thickness) to approx. 2 nm in thickness. Additionally, the sessile drop water contact angle decreased from approximately 80 degrees (functionalized surface of Formula XV) to 66 degrees (surface of Formula XXVII).

Example 18. Introduction of a PEG5 Carboxylic Acid Modified Surface (Formula XXVIII) to a Microfluidic Device The product microfluidic device from Example 5, having a surface of Formula XV, as described above, was treated with dibenzylcyclooctynyl (DBCO)-PEG5-acid, Compound 15, Broadpharm, Cat. #BP-22449) by flowing at least 250 microliters of an aqueous solution containing 1.33 micromolar Compound 15 through the microfluidic device having surface modifying azide ligands after vapor deposition. The reaction was allowed to proceed at 40° C. for at least 1 h. The microfluidic device having a modified surface of Formula XXVII was then rinsed by flowing at least 250 microliters of DI water through the chips. The contact angle was measured at 47°, and the thickness was 17.8 angstroms, each of which was measured as described herein. One of two regioisomers shown.

Formula XXVIII

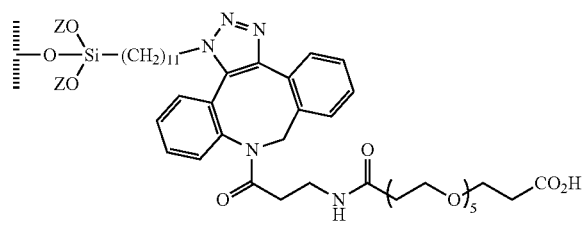

Example 19. Introduction of a PEG3 Modified Surface (Formula XXIX) to a Microfluidic Device A microfluidic device (Berkeley Lights, Inc.) having a first silicon electrode activation substrate and a second ITO bottom of the vacuum reactor in the presence of magnesium sulfate heptahydrate (0.5 g, Acros), as a water reactant source in a separate foil boat in the bottom of the vacuum reactor. The chamber was then pumped to 750 mTorr using a vacuum pump and then sealed. The vacuum reactor was placed within an oven heated at 110° C. for 24-48 h. This introduced a functionalized surface to all of the inner facing surfaces of the microfluidic device, where the functionalized surface had a structure of Formula XXIX:

Formula XXIX

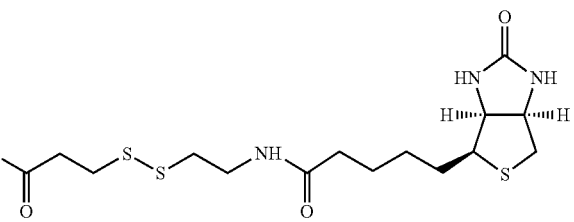

where Z is a bond to an adjacent silicon atom bound to the surface or is a bond to the surface and ≡ is the surface. After cooling to room temperature and introducing argon to the evacuated chamber, the microfluidic device was removed from the reactor. The contact angle for this surface was measured to be 55° and the average thickness to be 10.2 angstroms.

Example 20. Preparation of a Phosphonate Linked Surface (Formula XXXVI)

A silicon chip (780 microns thick, 1 cm by 1 cm) was pretreated as described above for Example 3, and subsequently treated with octadecylphosphonic acid (Compound 17, Sigma Aldrich Cat. #715166) as in Example 19 to provide the covalently modified surface of Formula XXXVI, where Z is a bond to a phosphorus atom in an adjacent linking group LG or is a bond to the surface ≡. The contact angle was measured to be 110°.

Formula XXXVI

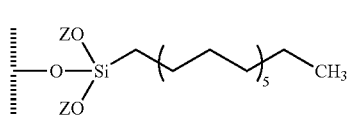

Example 21. Introduction of a Streptavidin Modified Surface (Formula XXXVII or Formula XXXVIII) to a Microfluidic Device. Method A The product microfluidic device from Example 5, having a surface of Formula XV as described above, was treated with dibenzylcyclooctynyl (DBCO) Streptavidin (SAV) Compound 18, Nanocs, Cat. #SV1-DB-1, where there are 2-7 DBCO for each molecule of SAV) by flowing at least 250 microliters of an aqueous solution containing 2 micromolar Compound 18 through the microfluidic device having surface modifying azide ligands after vapor deposition. The reaction was allowed to proceed at room temperature for at least 1 h. The microfluidic device having a modified surface of Formula XXVII was then rinsed by flowing at least 250 microliters of 1×PBS through the device.

Formula XXXVII

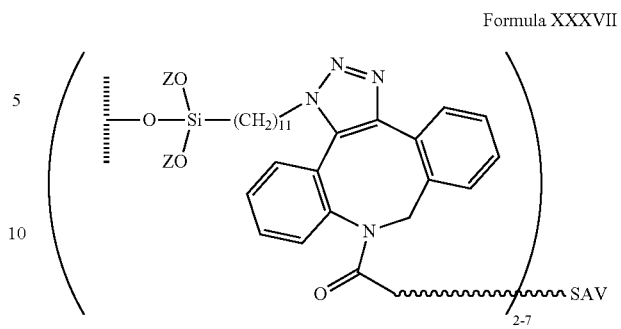

Method B.

The product modified surface of a microfluidic device of Example 17, having a surface of Formula XXVII, was washed with water and dried with repeated flushes of gaseous carbon dioxide while heating the chip to 40° C. A solution of 2 micromolar SAV in 1×PBS (ThermoFisher catalog #434301) was flowed into the microfluidic device and contacted with the biotinylated surface for 30 min. The excess SAV was removed by flowing 1×PBS through the microfluidic device, providing a surface of Formula XXXVIII:

Formula XXXVIII

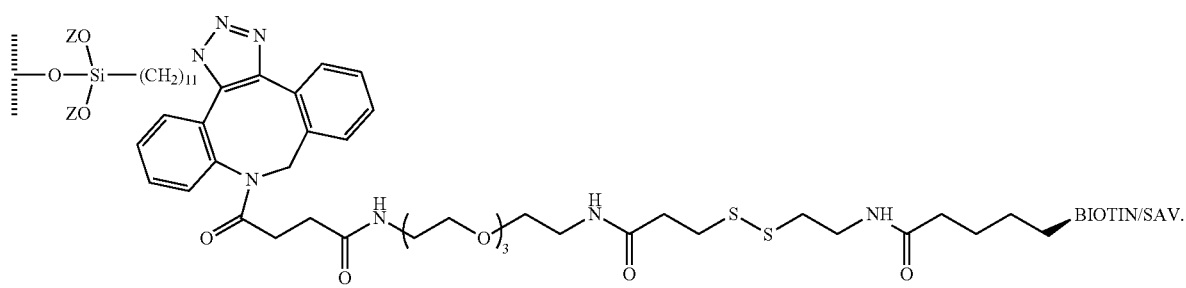

Example 22. Introduction of a Fibronectin Surface (Formula XXXIX) within a Microfluidic Device. Method A The product of Example 21, method B, a microfluidic device having a modified surface of Formula XXXVIII was treated with 50 microliters of a solution of 46 nM biotinylated bovine fibronectin (randomly biotinylated, Cytoskeleton Inc., Catalog #FNR03A, FNR03-B) in 1×PBS, which was incubated for one hour at 37° C., providing the surface of fibronectin of Formula XXXXIX:

Formula XXXIX

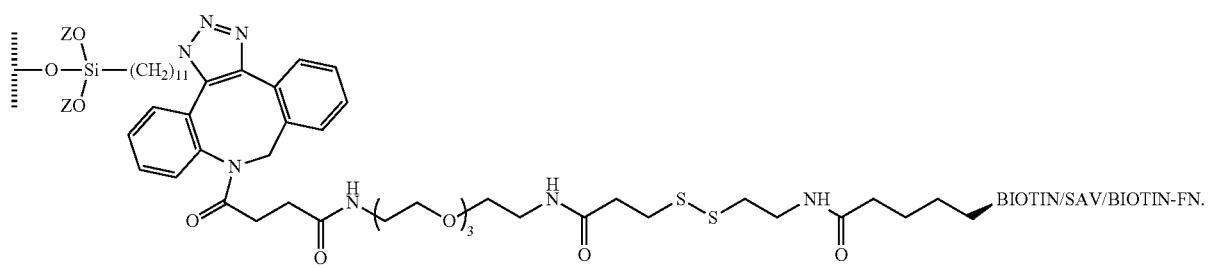

Modification in the Presence of Biological Cells.

In some embodiments, biological cells were introduced to the microfluidic device having surfaces of Formula XXXVIII, presenting streptavidin to the fluidic regions of the microfluidic device. After the cells were imported into sequestration pens, biotinylated fibronectin was introduced in PBS, and incubated for 1 hour. Adherence was observed.

Method B.

A fibronectin surface is introduced by treating a microfluidic device having a surface of Formula XXXVII as above with biotinylated fibronectin.

Method C.

A biotinylated-fibronectin stock was prepared at 2.3 micromolar in PBS and streptavidin stock was prepared at 19.2 micromolar in PBS. The two were mixed at fibronectin to streptavidin ratios of 1:1 to 1:2 and diluted in IX PBS to final concentration of at least 300 nanomolar. This solution was incubated for 15 minutes at room temperature to allow coupling of the fibronectin and streptavidin, forming a surface modifying reagent having a coupling group CG of biotin/streptavidin.

The product modified surface of a microfluidic device of Example 17, having a surface of Formula XXVII, was washed with water and dried with repeated flushes of gaseous carbon dioxide while heating the chip to 40° C. The pre-formed surface modifying reagent of SAV bound to biotinylated fibronectin was above was flowed into the microfluidic device. The device was incubated at room temperature for at least 30 minutes, and provided a modified surface of Formula XXXIX.

Further Generalization.

Additionally, any number of biologically relevant molecules may be introduced into a modified surface of a microfluidic device by the same process, by flowing in a biotinylated protein, peptide, small molecule or recognition motif, by attachment to either a surface of Formula XXXVII or Formula XXXVIII. For example, biotinylated laminin is flowed into a microfluidic device prepared as above with a surface of Formula XXXVII or XXXVIII, to produce a modified surface having laminin surface contact moieties (Formula XL):

pound 5, in varying ratios) in a foil boat in the bottom of the vacuum reactor in the presence of magnesium sulfate heptahydrate (0.5 g, Acros), as a water reactant source in a separate foil boat in the bottom of the vacuum reactor. The chamber was then pumped to 750 mTorr using a vacuum pump and then sealed. The vacuum reactor was placed within an oven heated at 110° C. for 24-48 h.

After cooling to room temperature and introducing argon to the evacuated chamber, the wafer was removed from the reactor. The wafer was rinsed with acetone, isopropanol, and dried under a stream of nitrogen. The modified surface of Formula XLI, which was a mixture where x and y may be present in a ratio of x:y or y:x of any value from 1 to $1\times10^8$, was evaluated for thickness, contact angle and for the presence of azide in the FTIR of the surface. Individual wafers were modified with mixtures of 1% undecyl azide: 99% methoxy PEG3; 10% undecyl azide: 90% methoxy PEG3; 50% undecyl azide: 50% methoxy PEG3: and 100% undecyl azide.

Formula XLI

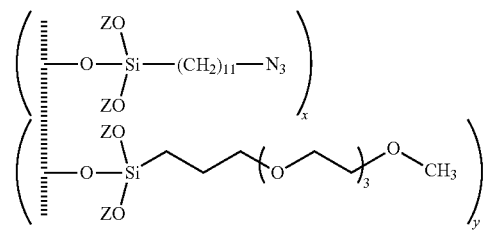

Figure 5B:
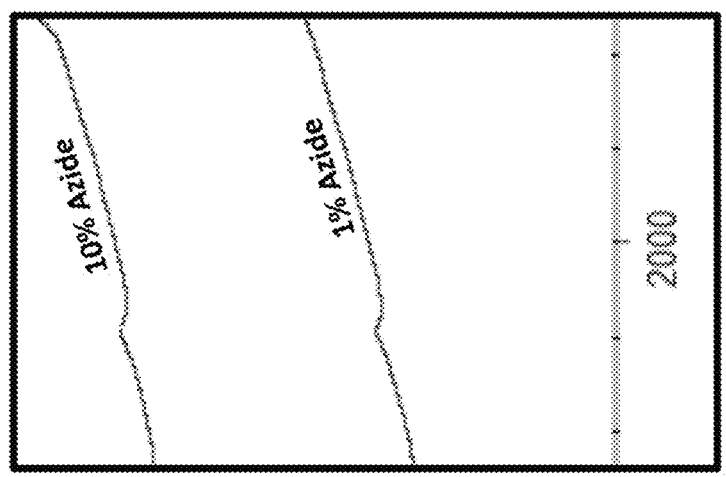
FIGS. 5A and 5B are graphical representation of overlaid FTIR for modified surfaces according to some embodiments of the disclosure.
Figure 5A:
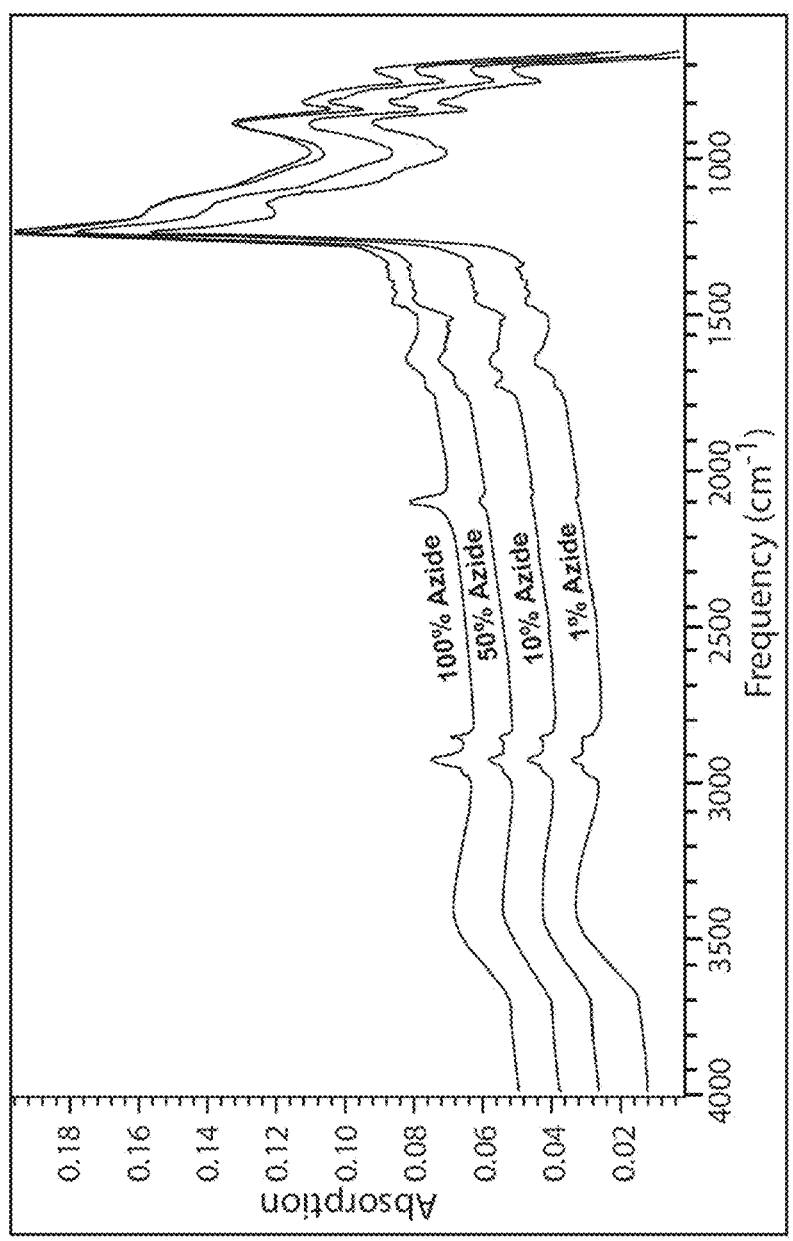

As shown in FIG. 5A, the overlaid FTIR traces clearly showed diminishing amount of azide asymmetric stretch 510 at ~2098 cm-1. FIG. 5B shows an enlarged portion of the overlaid traces at the location of the azide asymmetric stretch for the wafers having 10% Formula XV, and 1% Formula XV respectively. The relative amounts of azide Formula XL

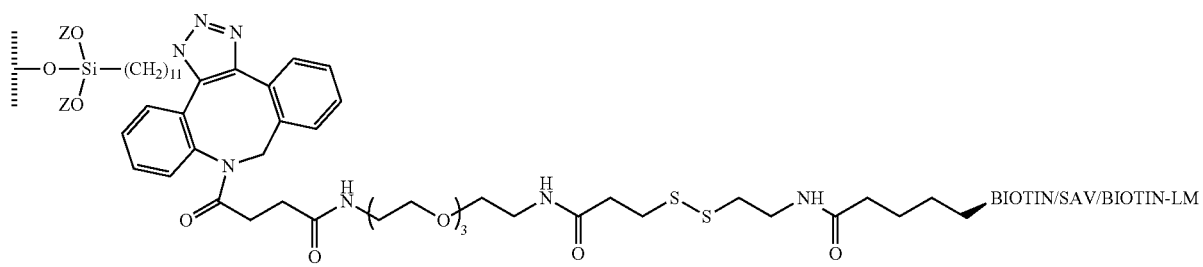

Example 23. Introduction of a Mixed Surface of Formula XLI in Varying Ratios

A silicon wafer was treated in an oxygen plasma cleaner (Nordson Asymtek) for 1 min, using 100 W power, 240 mTorr pressure and 440 sccm oxygen flow rate. The plasma treated microfluidic device was treated in a vacuum reactor with mixture of 3-azidoundecyl) trimethoxy silane (prepared as described above, Compound 5) and methoxytriethyleneoxypropyltrimethoxy silane (Gelest Inc. Catalog #SIM6493.4, having a similar molecular weight as Comwere clearly distinguishable and correlated to the ratios of Formula XV: Formula XXIX used.

The contact angle and thickness of the modified surface also differed when differing ratios of surfaces of Formula XV: Formula XXIX were present on the modified surface, as shown in Table 2: The data shows that control of deposition was obtained by changing the ratio of materials during the chemical vapor deposition process. The change in contact angle also shows that differing performance was possible with differing ratios of these surface modifications.

TABLE 2

Physical measurement of mixed surfaces.

| % Azide | Thickness (Å) | Contact Angle |
|---|---|---|
| 1% | 13.76 | 56° |
| 10% | 12.28 | 62° |
| 50% | 9.35 | 68° |
| 100% | 13.31 | 85° |

Example 24. Introduction of a Modified Surface Having a Mixture of a First Surface Modification Containing PEG and a Second Surface Modification of a Block Copolymer Containing Poly-L-Lysine, (Formula XLII) Using a Combination of Surface Modifying Reagents The product microfluidic device from Example 5, having a surface of Formula XV, as described above, was treated with a solution including 1.3 millimolar propargyl-PEG1-disulfide-PEG1-propargyl (Compound 19, BroadPharm Inc. Catalog #BP-23283), with copper sulfate (in excess), THPTA ligand, and sodium ascorbate. The excess copper sulfate prevents disulfide cleavage by ascorbate during the reaction, which was performed at 40° C. for about 15 min (and may alternatively be performed for about 1 hr at room temperature). After the incubation period was complete, the excess reagent and byproducts were removed by flushing with water. The interior of the microfluidic device was dried by flushing with carbon dioxide gas while heating the microfluidic device to 40° C., providing a surface that is a secondary functionalized surface having alkynyl $R_{x2}$ moieties.

The microfluidic device having secondary functionalized surfaces having alkynyl $R_{x2}$ moieties was then further modified by treating the microfluidic device with a mixture of two surface modifying reagents. The surface modifying reagents were flowed into the microfluidic device at a 1.3 millimolar concentration of a mixture of PEG-Azide (5 Kda, Aldrich Chemicals, Catalog #689475): azide-PEG5k-block copolymer poly-1-lysine 100 (Alamanda Polymers, MW 1600), where the ratio of azide-PEG and azide-PEG5k-b-PLL was varied between 1:50000 to 50000:1; along with copper sulfate (in excess), THPTA ligand, and sodium ascorbate. The excess copper sulfate prevents disulfide cleavage by ascorbate during the reaction, which was performed at 40° C. for about 15 min (and may alternatively be performed for about 1 hr at room temperature). After the incubation period was complete, the excess reagent and byproducts were removed by flushing with water. The interior of the microfluidic device was dried by flushing with carbon dioxide gas while heating the microfluidic device to 40° C., providing a microfluidic device with a mixture of a first surface modification, PEG5K, that is hydrophilic and a second surface modification, PEG5k-b-PLL, where the block of PLL provided positive charge (Formula XLII). The proportion of azide-PEG and azide-PEG5k-b-PLL may be an even higher ratio, e.g., 10,000:1 or more, as it was demonstrated that adhesion is observed even at extremely low proportions of the block copolymer poly-L-lysine surface contact moiety.

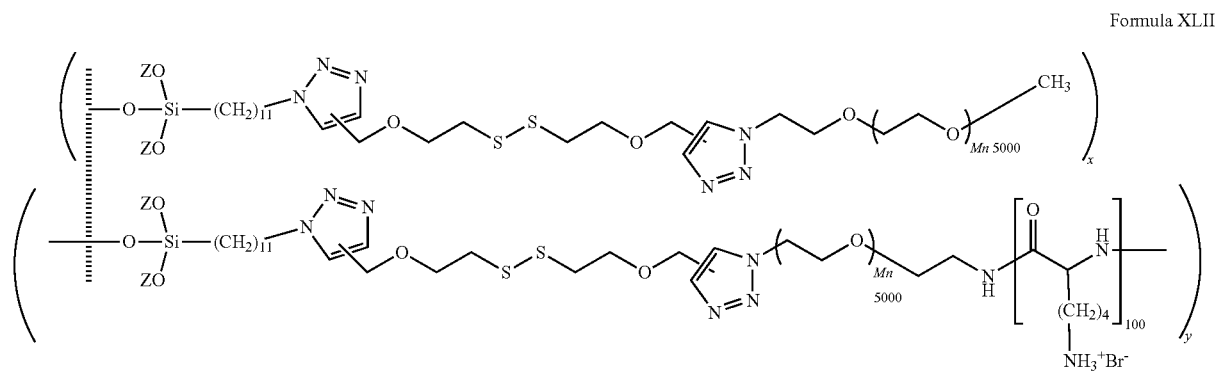

Formula XLII

The modified surface of Formula XLII, may have x and y present in a ratio of x:y or y:x of any value from 1 to $1 \times 10^8$.

Alternative Method of Modification.

The microfluidic device having a surface of Formula XV may be modified with DBCO-PEG4-alkyne (Compound 20, Conju-Probes, Inc. Catalog #CP-2039), in place of propargyl-PEG1-disulfide-PEG1-propargyl (Compound 19). by flowing at least 250 microliters of an aqueous solution containing 1.0 millimolar DBCO-PEG through the microfluidic device having surfaces of Formula XV. The reaction was allowed to proceed at 40° C. for at least 1 h. The microfluidic device having a modified surface of Formula XVIII was then rinsed by flowing at least 250 microliters of DI water through the chips, and may be treated as described in the preceding paragraphs to provide a microfluidic device with a mixture of a first surface modification, PEG5K, that is hydrophilic and a second surface modification, PEG5k-b-PLL, where the block of PLL provides positive charge (Formula XLIII), where the linker portion of the surface modifications differ from that of Formula XLII.

Formula XLIII

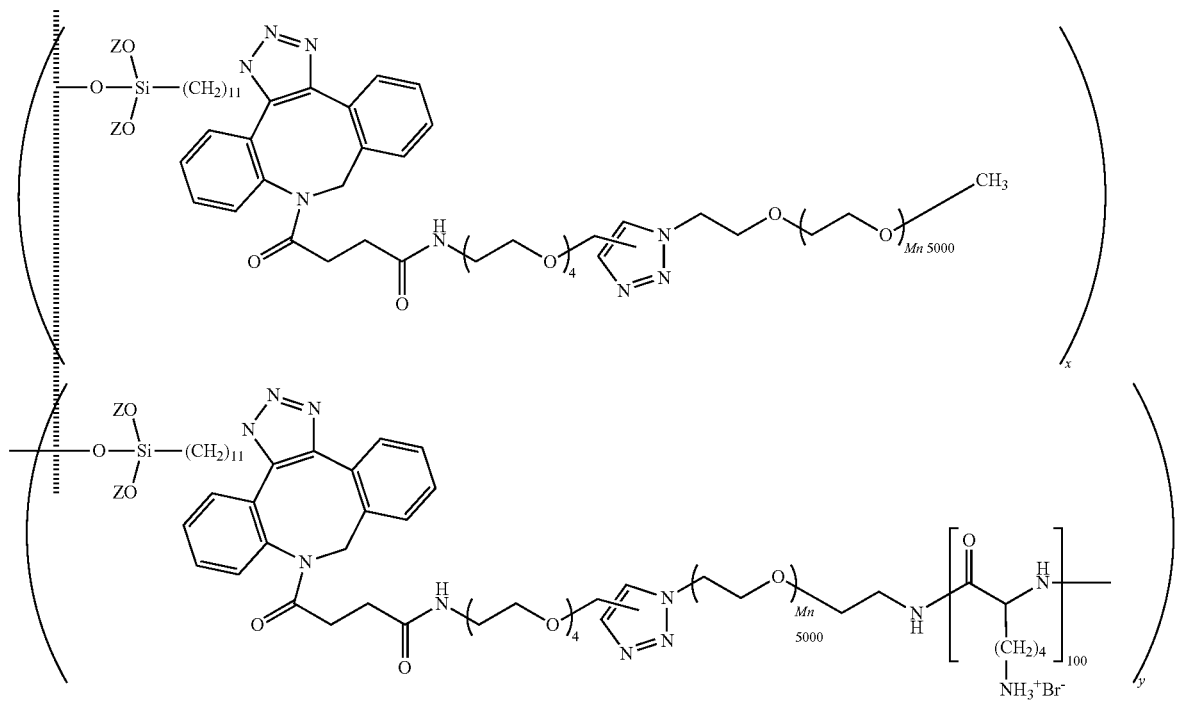

The modified surface of Formula XLIII, may have x and y present in a ratio of x:y or y:x of any value from 1 to $1\times10^8$.

Useful for Culturing Adherent Cells.

Surfaces of either Formula XLII or XLIII were useful in providing anchoring points (e.g., clusters of positively charged poly-L-lysine provided within the block co-polymer) for culturing adherent cells such as, but not limited to, HeLa cells. HeLa cells were observed to flatten out, grow and multiply during culture on either of these surfaces (data not shown).

Example 25. Introduction of a Modified Surface Having a Mixture of a First Surface Modification Containing PEG and a Second Surface Modification of a Poly-L-Lysine, (Formula XLIV) Using a Combination of Surface Modifying Reagents The product microfluidic device from Example 5, having a surface of Formula XV, as described above, was treated with a 1.33 millimolar solution including a 1:1 stoichiometric mixture of alkyne-poly-L-lysine HBr salt (100mer unit, Alamanda Polymers) and alkyne-modified PEG (j=MW ~5000 Da, Compound 6, JenKem Technologies) along with copper sulfate (in excess), THPTA ligand, and sodium ascorbate. The excess copper sulfate prevents disulfide cleavage by ascorbate during the reaction, which was performed at 40° C. for about 15 min (and may alternatively be performed for about 1 hr at room temperature). After the incubation period was complete, the excess reagent and byproducts were removed by flushing with water. The interior of the microfluidic device was dried by flushing with carbon dioxide gas while heating the microfluidic device to 40° C., providing a microfluidic device with a mixture of a first surface modification, PEG5K, that is hydrophilic and a second surface modification, poly-L-lysine, which provides positive charge (Formula XLIV).

Formula XLIV

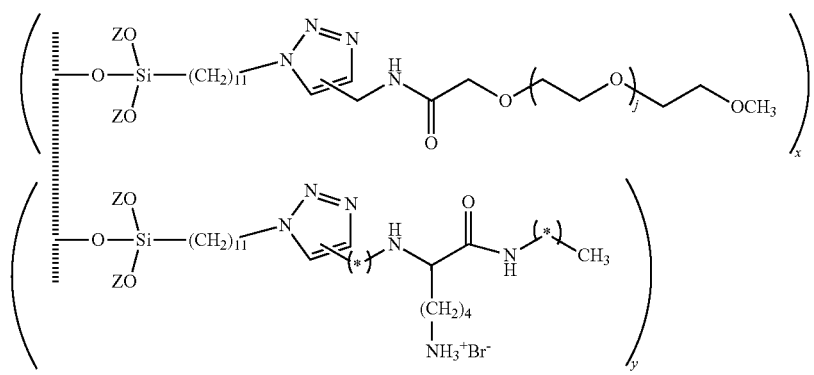

In the surfaces of Formula XLIV, (*) are proprietary linkers, and x and y may be present in a ratio of x:y or y:x of any value from 1 to 1×10⁸.

Useful for Culturing Adherent Cells.

Surfaces of Formula XLIV were useful in providing anchoring points (e.g., clusters of positively charged poly-L-lysine provided within the block co-polymer) for culturing adherent cells such as, but not limited to, HeLa cells. HeLa cells were observed to flatten out, grow and multiply during culture on either of these surfaces (data not shown).

Titration of Surface Modification 1: Surface Modification 2.

The ratios of the first surface modification (PEG 5 kDa) and the second surface modification (poly-L-lysine) of Formula XLIV were modified to modulate the population of points designed to encourage adherence, down to a ratio of 99 PEG 5 kDa: 1 poly-L-lysine. Using a 1% level of charged second surface modification (poly-L-lysine) laser bubble initiation of displacement, followed by export by dielectrophoretic force of cells was seen (Data not shown).

A microfluidic device having inner surfaces modified with a first surface modification of PEG 5 kDa and a second surface modification of poly-L-lysine having a percentage of poly-L-lysine surface modifications of about 0.00001% or 0.000001% is expected to permit adhesion of adherent cells (such as HeLa cells) while still permitting export of cultured cells using dielectrophoretic forces, without laser initiation of displacement.

Example 26. Introduction of a Mixed Surface Using Branched PEG Linkers (Formula XLV)

A modified surface having a first cleavable biotinylated surface modification in combination with a second surface modification which was hydrophilic PEG was introduced using a multi-armed PEG alkyne moiety. The amount of biotin reactive moieties present was controlled by modulating the amount of biotin reactive moiety vs hydrophilic surface contact moiety. Modulation was achieved by coupling moieties containing each of the surface contact moieties to arms of a multiarmed PEG alkyne, leaving sufficient alkyne reactive moieties on the multiarm PEG to effect efficient modification of the surface of the microfluidic device. The following procedure is described for a 1:1 ratio of biotin moieties to PEG carboxylic acid moieties, but experiments were also conducted for 100% biotin moieties; 10% biotin to 90% PEG carboxylic acid; and 1% biotin moieties to 99% PEG carboxylic acid moieties.

Compound 20

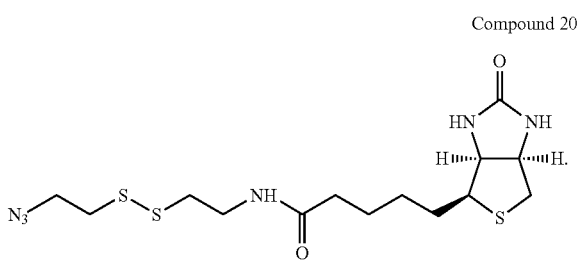

A solution of 1.3 millimolar 4-arm PEG (Creative PEG-Works Catalog #PSB-495), 1.3 millimolar solution of a 1:1 ratio of azide-disulfide-biotin (Compound 20, BroadPharm Catalog #BP-22877) and azide-PEG6-carboxylic acid (BroadPharm Catalog #BP-20612) in aqueous solution was reacted with sodium ascorbate, in the presence of a twofold excess of copper sulfate to form bi-modified multi-arm PEG upon incubation at room temperature for about 30 min. The solution of bi-modified multi-arm PEG was introduced onto a silicon wafer from Example 3, having a surface of Formula XV, as described above, with an additional aliquot of sodium ascorbate with a twofold excess of copper sulfate. The remaining alkyne ligands of the multi-arm PEG reacted with the azide reactive moieties of the surface of Formula XV to produce a mixed modified surface having a reactive moiety of biotin and a surface contact moiety of PEG-carboxylic acid (Formula XLV).

This mixed surface was then further modified by addition of 1 micromolar solution of Streptavidin (SAV) in PBS and incubated for 15 min at room temperature, producing a surface of Formula XLVI, where a first surface contact moiety is PEG-COOH and a second reactive moiety is SAV. The sample was washed and the thickness of the modified surface was measured.

The thicknesses of the modified layers are shown in Table 3, and vary as expected with the varying amount of streptavidin bound to available biotin surface contact moieties

TABLE 3

Measured thickness of modified surfaces.

| Sample | Surface of Formula XV (base surface) in angstroms | Total Modified surface having multi-arm PEG with biotin and PEG COOH in angstroms | Total Modified surface having multi-arm PEG with biotin/SAV and PEG COOH in angstroms | Increase of thickness due to added multi-arm PEG with biotin/SAV and PEG COOH in angstroms |
|---|---|---|---|---|
| 100% biotin | 11.8 | 33.7 | 60.6 | 26.9 |
| 50% biotin:50% PEG COOH | 11.8 | 31.8 | 51.6 | 19.8 |
| 10% biotin:90% PEG COOH | 12.0 | 30.8 | 44.2 | 13.4 |
| 1% biotin:99% PEG COOH | 12.2 | 30.8 | 34.3 | 3.4 |

The results show that a modulated surface having a combination of a streptavidin reactive moiety and a PEG COOH surface contact moiety was obtained. The streptavidin cam be modified further with biotinylated species such as biotin-fibronectin or any moiety capable of being biotinylated, to obtain a mixed surface of a first contact moiety (e.g., fibronectin) and a second contact moiety of PEG COOH, in any desired ratio.

Example 27. Introduction of Regioselective Surface Modifications of PEG5k in a First Region of the Microfluidic Device and Poly-L-Lysine within Sequestration Pens (Formula XLVII)

A previously prepared, dry and unprimed (e.g., not flushed with carbon dioxide gas) microfluidic device having a surface of Formula XV was treated with a 1.0 to 3.3 milllimolar aqueous solution of dibenzylcyclooctynyl (DBCO) modified-PEG, weight averaged molecular weight 5000 Da (Compound 8, Broadpharm, Cat. #BP-22461) by aspirating the solution through the microfluidic channel of the device at slightly lower than atmospheric pressure. The channel was resultingly filled with the reagent solution. However, due to the low pressure of the fluidic introduction and the unprimed nature of the surfaces within the microfluidic device, the DBCO modified PEG5 kDa solution does not enter the sequestration pens opening off of the microfluidic channel. After incubation for 30 min at room temperature, 80 microliters of water was aspirated at reduced pressure through the channel, washing any remaining reagent out of the microfluidic device. The solution was still controlled to flow only through the microfluidic channel. Additional flushing with water at 1 microliter/sec at low pressure was continued for about 5 min. The surface modified microfluidic channel was flushed with carbon dioxide gas repeatedly, while heating the device to 90° C.

The dried microfluidic device having a first surface modification of PEG5K was then primed with carbon dioxide as described above. The sequestration pens opening off of the microfluidic channel then were modified regioselectively by flowing in a 1.33 micromolar solution including a 1:1 stoichiometric mixture of alkyne-poly-L-lysine HBr salt (100mer unit, Alamanda Polymers) and alkyne-modified PEG (j=MW ~5000 Da, Compound 6, JenKem Technologies) along with copper sulfate (in excess), THPTA ligand, and sodium ascorbate. The excess copper sulfate prevents disulfide cleavage by ascorbate during the reaction, which was performed at 40° C. for about 15 min (and may alternatively be performed for about 1 hr at room temperature). After the incubation period was complete, the excess reagent and byproducts were removed by flushing with water. The interior of the microfluidic device was dried by flushing with carbon dioxide gas while heating the microfluidic device to 40° C., providing a microfluidic device with a regioselective introduction of a first surface modification, having only PEG5K, within the microfluidic channel and a second regioselective surface modification including poly-L-lysine, which provides positive charge for enhancing adherence of biological cells, only in the sequestration pens. (Formula XLV). Of note is the ability to modulate the ratios of the reagents used to modify the surface of the sequestration pens. The ratio of PEG-5K: poly-L-lysine was varied from 0:100 to 99.9999:0.0001% and adherence of HeLa cells was observed within the sequestration pens, while migration of the motile HeLa cells was inhibited by the presence of the merely hydrophilic surfaces within the channel.

A microfluidic device having inner surfaces modified with a first surface modification of PEG 5 kDa and a second surface modification of poly-L-lysine having a percentage of poly-L-lysine surface modifications of about 0.00001% or 0.000001% is expected to permit adhesion of adherent cells (such as HeLa cells) while still permitting export of cultured cells using dielectrophoretic forces, without laser initiation of displacement.

Further Generalization.

Any type of surface modifying reagent may be used in introduction of the second surface modification within the sequestration pen, and is not limited to a poly-L-lysine.

Secondary passivation of the microfluidic channel with a second surface modification only in the channel region. After the initial surface modification of the microfluidic channel as described above, there can be unreacted reactive moieties (e.g., azide) still present in the channel. Without wishing to be bound by theory, this may occur if the modifying reagent is bulky. Secondary passivation with a less sterically demanding surface modifying reagent may be able to access remaining reactive moieties to add a second surface modification to the modified surfaces of the channel without modifying the surfaces in the sequestration pen.

The microfluidic device, having a PEG5 kDa surface modification introduced to only to the microfluidic channel, was only rinsed with water after the surface introduction. A second treatment with DBCO-PEG4-OH (Aldrich Catalog #761982 at a concentration of 1.3 micromolar in an aqueous solution was performed similarly to the first treatment as described above. Since the microfluidic device was not primed, none of the second surface modifying reagent entered the sequestration pens and accordingly only the channel was further modified. After washing, drying and heating, followed by carbon dioxide priming, regioselective modification of the sequestration pens is then performed as above.

Example 28. Culturing of OKT3 Cells within a Microfluidic Device Having a PEG Modified Surface Materials:

OKT3 cells, a mouse B lymphocyte hybridoma, were obtained from the American Type Culture Collection (ATCC) (catalog ATCC® CRL-8001™), and were provided as a suspension cell line. Cultures were maintained by seeding $2\times10^5$ viable cells/mL and incubating at 37° C., using 5% carbon dioxide gaseous environment. Cells were split at $2\times10^4$ cells/mL or $1\times10^5$ cells/mL every 2-3 days. Cells were frozen in 5% dimethyl sulfoxide (DMSO)/95% complete growth medium.

Culture Medium:

IMDM (Gibco, catalog 12440053) was supplemented with 20% Fetal Bovine Serum (FBS) and 1% Penicillin-Streptomycin (10,000 U/mL) (Gibco, catalog 15140122). Complete media was then filtered through a 0.2 μm PES, sterile membrane filter unit (Nalgene, 567-0020).

Priming and Perfusion Procedures:

As above, in general experimental detail section.

System and Microfluidic Device:

As above, in the general experimental detail section The sequestration pens have a volume of about $7\times10^5$ cubic microns.

Modified Microfluidic Surface.

The microfluidic device had a covalently linked PEG modified surface, prepared as described above in Example 6 (Formula XVI).

An OKT3 cell suspension in the culture medium was introduced into the microfluidic device by flowing the suspension through a fluidic inlet and into the microfluidic channel. The flow was stopped and the cells were randomly loaded into sequestration pens by tilting the chip and allowing gravity to pull the cells into the sequestration pens.

Figure 6A:
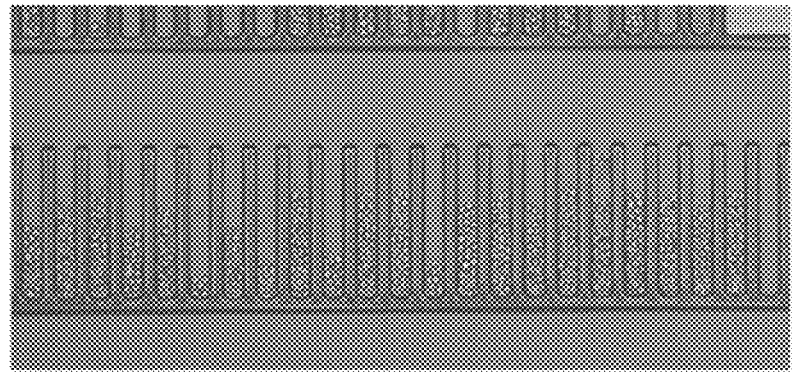
FIGS. 6A to 6B are photographic representations of cell culturing and cell unpenning according to an embodiment of the invention.

After loading the OKT3 cells into the sequestration pens, the culture medium was perfused through the microfluidic channel of the nanofluidic chip for a period of 3 days. FIG. 6A showed the growth of OKT3 cells on the PEG-modified surface of the sequestration pens of the microfluidic device. The growth of OKT3 cells on the PEG surface was improved relative to a non-modified surface of a similar microfluidic device (data not shown).

Figure 6B:
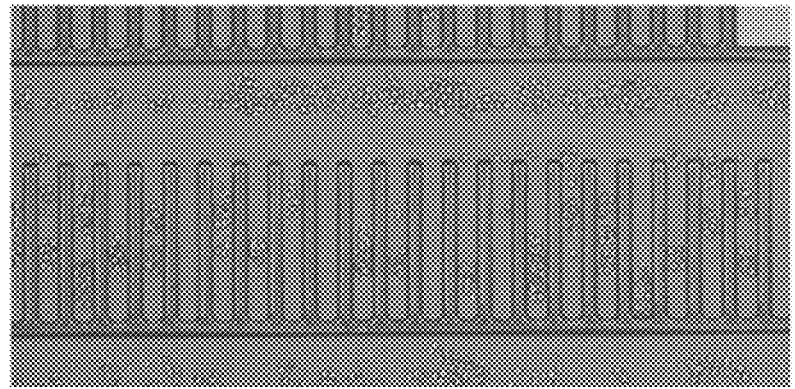

The OKT3 cells were then removed from the sequestration pens by OET. FIG. 6B showed the extent of removal from the sequestration pen at the end of a twenty minute period, demonstrating excellent ability to export the expanded OKT3 cells into the flow channel, which was improved over that of removal of OKT3 cells from a non-conditioned surface of a similar microfluidic device. The OKT3 cells were then exported from the microfluidic device (not shown).

Example 29: Culturing and Export of T Lymphocytes on a Dextran Modified Microfluidic Surface Materials. CD3+ cells from AllCells Inc. and mixed with anti-CD3/anti-CD28 magnetic beads (Dynabeads®, Thermofisher Scientific, Cat. No. 11453D) at a ratio of 1 bead/1 cell. The mixture was incubated in the same medium as the culturing experiment itself, for 5 hours in a 5% $CO_2$ incubator at 37° C. Following the incubation, the T cell/bead mixture was resuspended for use.

Culture Medium.

RPMI-1640 (GIBCO®, ThermoFisher Scientific, Cat. No. 11875-127), 10% FBS, 2% Human AB serum (50 U/ml IL2; R&D Systems).

Priming Procedure:

As above, in the general experimental detail section.

Perfusion Regime:

As above, in the general experimental detail section.

System and Microfluidic Device:

As above, in the general experimental detail section. The sequestration pens have a volume of about $7 \times 10^5$ cubic microns.

Modified Microfluidic Surface.

The microfluidic device had a covalently linked dextran modified surface, prepared as described above in Example 7.

The T cell (plus bead) suspension was introduced into the microfluidic device by flowing the resuspension through a fluidic inlet and into the microfluidic channel. The flow was stopped and T cells/beads were randomly loaded into sequestration pens by tilting the chip and allowing gravity to pull the T cells/beads into the growth chambers.

Figure 7A:
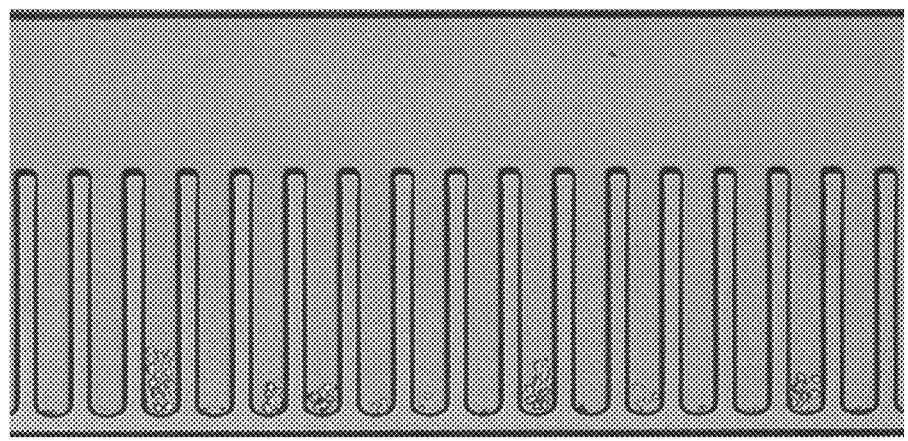
FIGS. 7A to 7B are photographic representations of cell culturing and cell unpenning according to another embodiment of the invention.

After loading the T cells/beads into the sequestration pens, the culture medium was perfused through the microfluidic channel of the nanofluidic chip for a period of 4 days. FIG. 7A showed the growth of T cells on the dextran modified surface of the sequestration pens of the microfluidic device. The growth of T cell on the dextran surface was improved relative to a non-conditioned surface of a similar microfluidic device (data not shown).

Figure 7B:
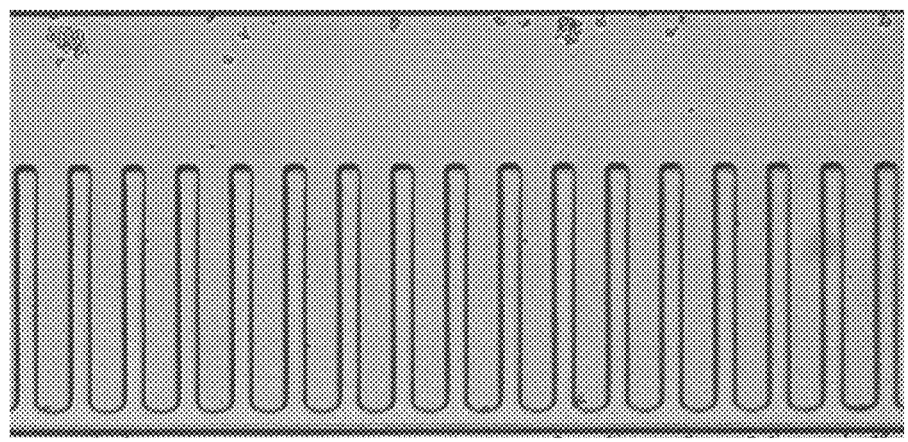

The T cells were then removed from the sequestration pens by gravity (e.g., tilting the microfluidic device). FIG. 7B showed the extent of removal from the sequestration pen at the end of a twenty minute period, demonstrating excellent ability to export the expanded T cells into the flow channel, which was improved over that of removal of T cells from a non-modified surface of a similar microfluidic device (data not shown). The T cells were then exported from the microfluidic device (not shown).

In addition to any previously indicated modification, numerous other variations and alternative arrangements may be devised by those skilled in the art without departing from the spirit and scope of this description. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. As used herein, the examples and embodiments, in all respects, are meant to be illustrative only and should not be construed to be limiting in any manner. It should also be noted, that while the term step is used herein, that term may be used to simply draw attention to different portions of the described methods and is not meant to delineate a starting point or a stopping point for any portion of the methods, or to be limiting in any other way.

Recitation of Some Embodiments of the Disclosure

1. A microfluidic device including: an enclosure including a base, a cover, and microfluidic circuit material defining a fluidic circuit therein, where at least one inner surface of the base, the cover and the microfluidic circuit material has a plurality of first covalently bound surface modifications, each including a first linking group and a first moiety, where the first moiety is a first surface contact moiety or a first reactive moiety; where at least one inner surface of the base, the cover and the microfluidic circuit material has a plurality of second covalently bound surface modifications, each including a second linking group and a second moiety, where the second moiety is a second surface contact moiety or second reactive moiety, and where the first linking group and the second linking group are different from each other and/or the first moiety is different from the second moiety.

2. The microfluidic device of embodiment 1, where the first moiety and the second moiety may each be covalently bound to the surface via a linking group LG independently selected from —W—Si(OZ)$_2$O— and —OP(O)$_2$O—, where W is O, S, or N, and where Z is a bond to a silicon atom in an adjacent linking group LG or is a bond to the surface.

3. The microfluidic device of embodiment 1 or 2, where the first surface contact moiety may include one or more of an alkyl, fluoroalkyl, monosaccharide, polysaccharide, alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety; and/or where the second surface contact moiety may include one or more of an alkyl, fluoroalkyl, monosaccharide, polysaccharide, alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety.

4. The microfluidic device of embodiment 1 or 2, where the first surface contact moiety may include a polyethylene glycol moiety, a dextran moiety, a proteinaceous moiety, a poly carboxylic acid, a polylysine moiety, or any combination thereof; and/or where the second surface contact moiety may include a polyethylene glycol moiety, a dextran moiety, a proteinaceous moiety, a poly carboxylic acid, a polylysine moiety, or any combination thereof.

5. The microfluidic device of any one of embodiments 1 to 4, where the first reactive moiety may be an alkyne moiety, an azide moiety, a carboxylic acid moiety, an amine moiety, an olefinic moiety, a tetrazinyl moiety, a trans-cyclooctenyl moiety, a thiol moiety, a maleimide moiety, a biotin moiety, a streptavidin moiety, a halide moiety, a cyano moiety, isocyanate moiety, an epoxide moiety, a hydroxyamine moiety, or a sulfonyl fluoride moiety; and/or where the second reactive moiety may be an alkyne moiety, an azide moiety, a carboxylic acid moiety, an amine moiety, an olefinic moiety, a tetrazinyl moiety, a trans-cyclooctenyl moiety, a thiol moiety, a maleimide moiety, a biotin moiety, a streptavidin moiety, a halide moiety, a cyano moiety, isocyanate moiety, an epoxide moiety, a hydroxyamine moiety, or a sulfonyl fluoride moiety.

6. The microfluidic device of any one of embodiments 1 to 5, where the first covalently bound surface modifications may include a linker, where the linker includes 1 to 200 non-hydrogen atoms selected from any combination of silicon, carbon, nitrogen, oxygen, sulfur and phosphorus atoms; and/or where the second covalently bound surface modifications may include a linker, where the linker may include 1 to 200 non-hydrogen atoms selected from any combination of silicon, carbon, nitrogen, oxygen, sulfur and phosphorus atoms.

7. The microfluidic device of embodiment 6, where the linker of the first covalently bound surface modifications may further include one or two coupling group CG moieties; and/or where the linker of the second covalently bound surface modifications may further include one or two coupling group CG moieties.

8. The microfluidic device of embodiment 1, where the first covalently bound surface modifications may have a structure selected from Formula XXX, Formula V, Formula VII, Formula XXXI, Formula VIII, and Formula IX:

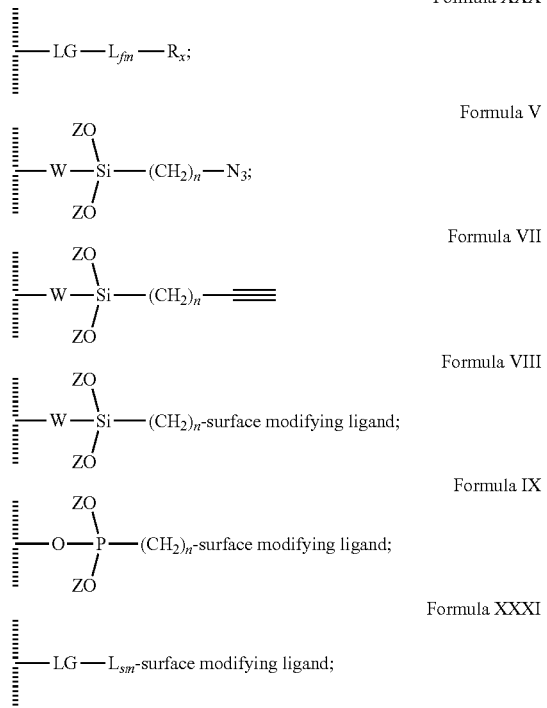

where: LG is —W—Si(OZ)$_2$O— or —OP(O)$_2$O—; $L_{fm}$ is a linker including 1 to 200 non-hydrogen atoms selected from any combination of silicon, carbon, nitrogen, oxygen, sulfur and phosphorus atoms and may further include 0 or 1 coupling groups CG; $R_x$ is a reactive moiety; W is O, S, or N; Z is a bond to an adjacent silicon atom or is a bond to the surface; n is an integer of 3 to 21; $L_{sm}$ is a linker including 1 to 200 non-hydrogen atoms selected from any combination of silicon, carbon, nitrogen, oxygen, sulfur and phosphorus atoms and further may include 0, 1, 2, or 3 coupling groups CG; and ⦀ is the surface.

9. The microfluidic device of embodiment 8, where LG may be —W—Si(OZ)$_2$O—, and where W may be O.

10. The microfluidic device of embodiment 8 or 9, where n is 7 to 21.

11. The microfluidic device of any one of embodiments 8 to 10, where the reactive moiety $R_x$ may be alkyne, azide, amine, carboxylic acid, biotin, streptavidin, olefin, trans cyclooctene, s-tetrazine, thiol, maleimide, halide, cyano, isocyanate, epoxide, hydroxyamine, a masked hydroxyl, or sulfonyl fluoride.

12. The microfluidic device of any one of embodiments 8 to 10, where the reactive moiety $R_x$ may be alkyne, azide, amine, carboxylic acid, biotin, or streptavidin.

13. The microfluidic device of any one of embodiments 1 or 8-12, where the second covalently bound surface modifications may have a structure selected from Formula XXX', Formula V', Formula VII', Formula XXXI', Formula VIII', and Formula IX':

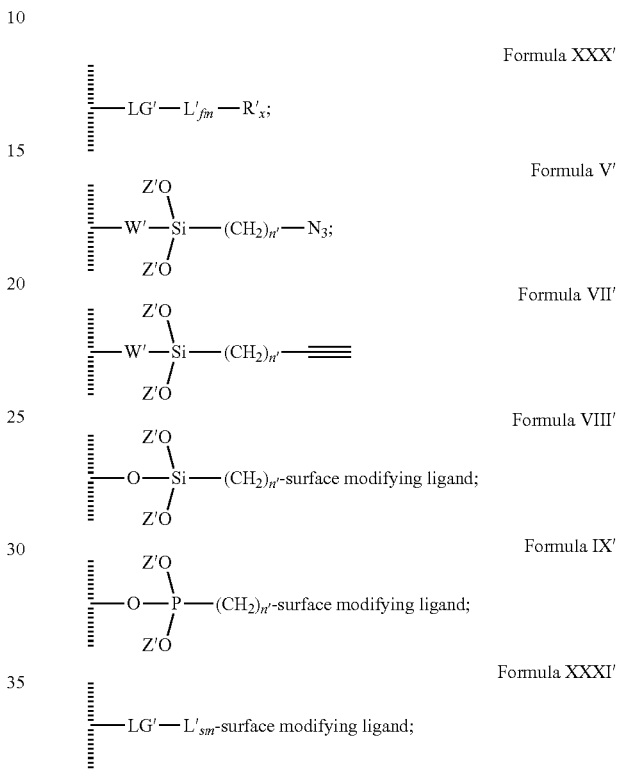

where: LG' is —W'—Si(OZ')$_2$O— or —OP(O)$_2$O—; $L'_{fm}$ is a linker including 1 to 200 non-hydrogen atoms selected from any combination of silicon, carbon, nitrogen, oxygen, sulfur and phosphorus atoms and may further include 0 or 1 coupling groups CG; $R_x'$ is a reactive moiety; W' is O, S, or N; Z' is a bond to an adjacent silicon atom or is a bond to the surface; n' is an integer of 3 to 21; $L'_{sm}$ is a linker including 1 to 200 non-hydrogen atoms selected from any combination of silicon, carbon, nitrogen, oxygen, sulfur and phosphorus atoms and further may include 0, 1, 2, or 3 coupling groups CG; and ⦀ is the surface.

14. The microfluidic device of embodiment 13, where LG' may be —W'—Si(OZ')$_2$O—, and where W' may be O.

15. The microfluidic device of embodiment 13 or 14, where n' may be 7 to 21.

16. The microfluidic device of any one of embodiments 13 to 15, where the reactive moiety $R_x'$ may be alkyne, azide, amine, carboxylic acid, biotin, streptavidin, olefin, trans cyclooctene, s-tetrazine, thiol, maleimide, halide, cyano, isocyanate, epoxide, hydroxyamine, a masked hydroxyl, or sulfonyl fluoride.

17. The microfluidic device of any one of embodiments 13 to 15, where the reactive moiety $R_x'$ may be alkyne, azide, amine, carboxylic acid, biotin, or streptavidin.

18. The microfluidic device of any one of embodiments 1 to 17, where the first moiety may be different from the second moiety.

19. The microfluidic device of any one of embodiments 13 to 17, where the first covalently bound surface modifications may have a structure selected from Formula XXX, Formula V, and Formula VII, and where the second covalently bound surface modifications may have a structure selected from Formula XXXI', Formula VIII', and Formula IX'.

20. The microfluidic device of embodiment 19, where the first covalently bound surface modifications and the second covalently bound surface modifications may be on a common inner surface of the base, the cover, and/or the microfluidic circuit material.

21. The microfluidic device of embodiment 20, where the first and second covalently bound surface modifications may be randomly distributed upon the common inner surface.

22. The microfluidic device of embodiment 20, where the common inner surface may include a first region including the first covalently bound surface modifications and a second region including the second covalently bound surface modifications, where the first region is adjacent to the second region.

23. The microfluidic device of embodiment 20, where the common inner surface may include a plurality of first regions including the first covalently bound surface modifications and a second region including the second covalently bound surface modifications, where the first regions of the plurality are separated from each other by or each adjacent to the second region.

24. The microfluidic device of embodiment 20, where the common inner surface may include a plurality of second regions including the second covalently bound surface modifications and a first region including the first covalently bound surface modifications, where the second regions of the plurality are separated from each other by or each adjacent to the first region.

25. The microfluidic device of any one of embodiments 13 to 18, where the first covalently bound surface modifications may have a structure selected from Formula XXXI, Formula VIII, and Formula IX, where the second covalently bound surface modifications may have a structure selected from Formula XXXI', Formula VIII' and Formula IX', and where the first covalently bound surface modifications are different from the second covalently bound surface modifications.

26. The microfluidic device of embodiment 25, where the surface modifying ligand of the first covalently bound surface modifications may have a structure of Formula X, and where the surface modifying ligand of the second covalently bound surface modifications may have a structure of Formula XI:

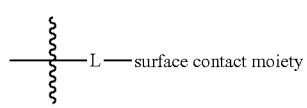

Formula X

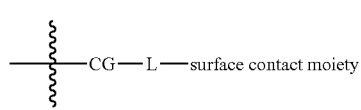

Formula XI where: CG is a coupling group; and L is a linker including a bond or 1 to 200 non-hydrogen atoms selected from any combination of silicon, carbon, nitrogen, oxygen, sulfur and phosphorus atoms.

27. The microfluidic device of embodiment 25 or 26, where the first covalently bound surface modifications and the second covalently bound surface modifications may be on a common inner surface of the base, the cover, and/or the microfluidic circuit material.

28. The microfluidic device of embodiment 27, where the first and second covalently bound surface modifications may be randomly distributed upon the common inner surface.

29. The microfluidic device of embodiment 27, where the common inner surface may have a first region including the first covalently bound surface modifications and a second region including the second covalently bound surface modifications, and where the first region is adjacent to the second region.

30. The microfluidic device of embodiment 27, where the common inner surface may include a plurality of first regions having the first covalently bound surface modifications and a second region having the second covalently bound surface modifications, where the first regions of the plurality are separated from each other by or each adjacent to the second region.

31. The microfluidic device of any one of embodiments 27 to 30, where the common inner surface may include more than one kind of proteinaceous moiety.

32. The microfluidic device of any one of embodiments 25 to 31, where the surface modifying ligand of the first covalently bound surface modifications may include a first proteinaceous moiety, and where the surface modifying ligand of the second covalently bound surface modifications may include a second proteinaceous moiety, and where the first and second proteinaceous moieties are different.

33. The microfluidic device of any one of embodiments 13 to 18, where the first covalently bound surface modifications may have a structure selected from Formula XXX, Formula V, and Formula VII, where the second covalently bound surface modifications may have a structure selected from Formula XXX', Formula V', and Formula VII', where the first covalently bound surface modifications are different from the second covalently bound surface modifications, and where the reactive moiety of the first covalently bound surface modifications does not react with the reactive moiety of the second covalently bound surface modifications.

34. The microfluidic device of embodiment 33, where the first covalently bound surface modifications and the second covalently bound surface modifications may be on a common inner surface of the base, the cover, and/or the microfluidic circuit material.

35. The microfluidic device of embodiment 34, where the common inner surface may include a first region including the first covalently bound surface modifications and a second region including the second covalently bound surface modifications, and where the first region is adjacent to the second region.

36. The microfluidic device of embodiment 34, where the common inner surface may include a plurality of first regions including the first covalently bound surface modifications and a second region including the second covalently bound surface modifications, where the first regions of the plurality are separated from each other by or each adjacent to the second region.

37. The microfluidic device of any one of embodiments 1 to 36, where the fluidic circuit may include a flow region and a sequestration pen, where the sequestration pen may include an isolation region and a connection region, where the connection region may include a proximal opening to the flow region and fluidically connects the isolation region to the flow region.

38. The microfluidic device of embodiment 37, where at least one surface of the flow region may be modified with the first covalently bound surface modifications, where at least one surface of the sequestration pen may be modified with the second covalently bound surface modifications.

39. The microfluidic device of embodiment 38, where the second covalently bound surface modifications may include a surface contact moiety configured to anchor adherent cells.

40. The microfluidic device of embodiment 38 or 39, where the first covalently bound surface modifications may include a surface contact moiety configured to inhibit or substantially prevent migration of motile cells out of the sequestration pen.

41. The microfluidic device of any one of embodiments 37 to 40, where the flow region may be fluidically connected to a fluidic inlet and a fluidic outlet, and may be configured to contain a flow of a first fluidic medium.

42. The microfluidic device of any one of embodiments 37 to 41, where the sequestration pen may include walls made of microfluidic circuit material.

43. The microfluidic device of embodiment 42, where the walls of the sequestration pen may extend from the inner surface of the base to the inner surface of the cover.

44. The microfluidic device of any one of embodiments 37 to 43, where the inner surface of the base may underlay the flow region and an interior of the sequestration pen.

45. The microfluidic device of any one of embodiments 37 to 44, where the fluidic circuit further may include a plurality of sequestration pens each having at least one inner surface modified with the first and/or second covalently bound surface modifications.

46. The microfluidic device of any one of embodiments 1 to 45, where the first covalently bound surface modifications and/or the second covalently bound surface modifications may form a monolayer.

47. The microfluidic device of any one of embodiments 1 to 46, where the inner surface of the base and/or the inner surface of the cover of the enclosure may include glass, silicon, silicon oxide, hafnium oxide, indium tantalum oxide, or aluminum oxide.

48. The microfluidic device of any one of embodiments 1 to 47, where the inner surface of the microfluidic circuit material may include polydimethylsiloxane (PDMS) or photopatternable silicone (PPS).

49. The microfluidic device of any one of embodiments 1 to 48, where substantially all of the inner surfaces of the enclosure may be covalently modified.

50. The microfluidic device of any one of embodiments 1 to 49, where at least one inner surface of the base, the cover and the microfluidic circuit material may have a plurality of third (fourth fifth, etc.) covalently bound surface modifications including a third (fourth, fifth, etc.) linking group, and a third (fourth, fifth, etc.) moiety, where the third (fourth, fifth, etc.) moiety is a third (fourth, fifth, etc.) surface contact moiety or a third (fourth, fifth, etc.) reactive moiety, where the third (fourth, fifth, etc.) linking group may be different from each of the first and second linking groups and/or the third (fourth, fifth, etc.) moiety may be different from each of the first and second moieties.

51. The microfluidic device of any one of embodiments 1 to 50, where none of the inner surfaces of the enclosure include gold metal.

52. The microfluidic device of any one of embodiments 1 to 51, where the cover and/or the base may include a semiconductor substrate.

53. The microfluidic device of embodiment 52, where the semiconductor substrate may include a dielectrophoresis (DEP) configuration.

54. The microfluidic device of embodiment 53, where the DEP configuration may be optically actuated.

55. The microfluidic device of any one of embodiments 52 to 54, where the semiconductor substrate may include an electrowetting (EW) configuration.

56. The microfluidic device of embodiment 55, where the fluidic circuit may include a flow region, fluidically connected to a EW fluidic inlet and an EW fluidic outlet, which is configured to contain a flow of an EW fluidic medium.

57. The microfluidic device of embodiment 56, which may further include a chamber including walls enclosing an internal region (which can include an isolation region) and an opening to the flow region.

58. The microfluidic device of embodiment 57, where the walls of the at least one chamber include microfluidic circuit material.

59. The microfluidic device of embodiment 57 or 58, where the walls of the at least one chamber may extend from the inner surface of the base to the inner surface of the cover.

60. The microfluidic device of any one of embodiments 1 to 59, where the cover may be an integral part of the microfluidic circuit material.

61. The microfluidic device of any one of embodiments 1 to 59, where the first or the second covalently bound surface modification may have a structure of one of the following formulae: Formula XV; Formula XVI; Formula XVII; Formula XVIII; Formula XIX; Formula XX; Formula XXI; Formula XXII; Formula XXIII; Formula XXIV; Formula XXV; Formula XXVI; Formula XXVII; Formula XXVIII; Formula XXIX; Formula XXXVI; Formula XXXVII; Formula XXXVIII; Formula XXXIX; and Formula XL.

62. The microfluidic device of embodiment 1, where at least one inner surface of the base, the cover and the microfluidic circuit material of the microfluidic device may have a plurality of first covalently bound surface modifications and a plurality of second covalently bound modifications of one of the following formulae: Formula XLI; Formula XLII; Formula XLIII; Formula XLIV; Formula XLV; Formula XLV; and Formula XLVII.

63. A method of forming a covalently modified surface on at least one inner surface of a microfluidic device including an enclosure having a base, a cover and microfluidic circuit material defining a fluidic circuit therein, the method including: contacting the at least one inner surface with a first modifying reagent and a second modifying reagent; reacting the first modifying reagent with a plurality of first nucleophilic moieties of the at least one inner surface; reacting the second modifying reagent with a plurality of second nucleophilic moieties of the at least one inner surface; and thereby forming at least one covalently modified surface including first covalently bound surface modifications, each including a first linking group and a first moiety that is a first surface contact moiety or a first reactive moiety, and second covalently bound surface modifications, each including a second linking group and a second moiety that is a second surface contact moiety or second reactive moiety, where the first linking group is different from the second linking group or the first moiety is different from the second moiety.

64. The method of embodiment 63, where reacting the first modifying reagent with the at least one inner surface may be performed at the same time as reacting the second modifying reagent with the at least one inner surface of the microfluidic device.

65. The method of embodiment 63, where reacting the first modifying reagent with the at least one inner surface may be performed before or after reacting the second modifying reagent with the at least one inner surface of the microfluidic device.

66. The method of any one of embodiments 63 to 65, where the first modifying reagent may be reacted under conditions allowing the first modifying reagent to react with any available nucleophilic moiety of the at least one inner surface, and where the second modifying reagent may be reacted under conditions allowing the second modifying reagent to react with any available nucleophilic moiety of the at least one inner surface, such that the first and second covalently bound surface modifications are positioned at random upon the at least one inner surface of the microfluidic device.

67. The method of any one of embodiments 63 to 66, where the first modifying reagent may be reacted under conditions that promote a reaction between the first modifying reagent and nucleophilic moieties located on a first region of the at least one surface, and where the second modifying reagent may be reacted under conditions that promote a reaction between the second modifying reagent and nucleophilic moieties located on a second region of the at least one surface, where the first region is adjacent to the second region.

68. The method of any one of embodiments 63 to 66, where the first modifying reagent is reacted under conditions that promote a reaction between the first modifying reagent and nucleophilic moieties located within any of a plurality of first regions separated from each other on the at least one surface, and where the second modifying reagent is reacted under conditions that promote a reaction between the second modifying reagent and nucleophilic moieties located within a second region, where the second region is adjacent to or surrounds each of the plurality of first regions.

69. The method of any one of embodiments 63 to 68, where the fluidic circuit includes a flow region and a sequestration pen having an isolation region and a connection region, where the connection region includes a proximal opening to the flow region and fluidically connects the isolation region to the flow region.

70. The method of embodiment 69 where the first modifying reagent may be reacted with first nucleophilic moieties located on a surface of the flow region to form first covalently bound surface modifications thereon, and where the second modifying reagent may be reacted with second nucleophilic moieties located on a surface of the sequestration pen to form second covalently bound surface modifications thereon.

71. The method of embodiment 70, where the first covalently bound surface modifications may include a first reactive moiety and the second covalently bound surface modifications may include a second reactive moiety.

72. The method of embodiment 71, where the first and the second reactive moieties do not react with each other.

73. The method of embodiment 70, where the second covalently bound surface modifications may include a surface contact moiety which is a support moiety for adherent cells.

74. The method of embodiment 70 or 73, where the first covalently bound surface modifications may include a surface contact moiety configured to inhibit or substantially prevent migration of motile cells out of the sequestration pen.

75. The method of any one of embodiments 63 to 74, where forming the covalently modified surface may include forming a covalently modified surface on substantially all the inner surfaces of the microfluidic device.

76. The method of any one of embodiments 63 to 75, where the first modifying reagent may have a structure of one of the following formulae:

$$V-(CH_2)_n-\text{surface modifying ligand;} \quad \text{Formula I}$$

$$\begin{array}{c} RO \\ RO-Si-(CH_2)_n-\text{surface modifying ligand;} \\ RO \end{array} \quad \text{Formula III}$$

$$V-L_{sm}-\text{surface modifying ligand;} \quad \text{Formula XXXII}$$

$$\begin{array}{c} RO \\ RO-Si-(CH_2)_n-N_3; \\ RO \end{array} \quad \text{Formula IV}$$

$$\begin{array}{c} RO \\ RO-Si-(CH_2)_n-\equiv; \quad \text{and} \\ RO \end{array} \quad \text{Formula VI}$$

$$V-L_{fm}-R_x; \quad \text{Formula XXXIII}$$

where: V is $-P(O)(OH)_2$ or $-Si(T)_2W$; W is -T, $-SH$, or $-NH_2$ and is the moiety configured to form a covalent bond with the at least one inner surface; T is independently OH, $OC_{1-6}$ alkyl, or halo; R is $C_{1-6}$ alkyl; $L_{fm}$ is a linker including 1 to 200 non-hydrogen atoms selected from any combination of silicon, carbon, nitrogen, oxygen, sulfur and phosphorus atoms, and further includes 0 or 1 coupling groups CG; $R_x$ is a reactive moiety; n is an integer of 3 to 21, and $L_{sm}$ is a linker including 1 to 200 non-hydrogen atoms selected from any combination of silicon, carbon, nitrogen, oxygen, sulfur and phosphorus atoms and further includes 0, 1, 2, or 3 coupling groups CG.

77. The method of embodiment 76, where W may be $OC_{1-6}$ alkyl or halo.

78. The method of embodiment 76 or 77, where n may be 7 to 21.

79. The method of any one of embodiments 76 to 78, where T is $OC_{1-3}$ alkyl or halo and/or R is $C_{1-3}$ alkyl.

80. The method of any one of embodiments 76 to 79, where the reactive moiety $R_x$ may be alkyne, azide, amine, carboxylic acid, biotin, or streptavidin.

81. The method of any one of embodiments 76 to 79, where the reactive moiety $R_x$ may be alkyne, azide, amine, carboxylic acid, biotin, streptavidin, olefin, trans cyclooctene, s-tetrazine, thiol, maleimide, halide, cyano, isocyanate, epoxide, hydroxyamine, masked hydroxyl, or sulfonyl fluoride.

82. The method of any one of embodiments 76 to 81, where the first modifying reagent may have a structure of Formula I, Formula III, or Formula XXXII, and where the surface modifying ligand of the first modifying reagent may have a structure of Formula X or Formula XI:

$$\}-L-\text{surface contact moiety} \quad \text{Formula X}$$

-continued

Formula XI

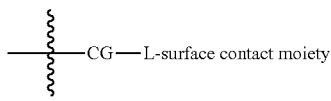

where: CG is a coupling group; L is a linker including a bond or 1 to 200 non-hydrogen atoms selected from any combination of silicon, carbon, nitrogen, oxygen, sulfur and phosphorus atoms; the sum of $L_{sm}$ and L is 1 to 200 non-hydrogen atoms, not including atoms of the CG if present; and the surface contact moiety is a moiety configured to support cell growth, viability, portability, or any combination thereof in the microfluidic device.

83. The method of embodiment 82, where the surface contact moiety of the first modifying reagent may include one or more of an alkyl, fluoroalkyl, monosaccharide, polysaccharide; alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety.

84. The method of embodiment 82, where the surface contact moiety of the first modifying reagent may include a polyethylene glycol, a dextran moiety, a proteinaceous moiety, a poly carboxylic acid, or a poly lysine moiety.

85. The method of any one of embodiments 63 to 84, where the second modifying reagent may have a structure of one of the following formulae:

   Formula I'

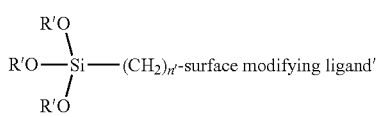   Formula III'

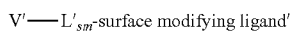   Formula XXXII'

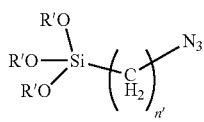   Formula IV'

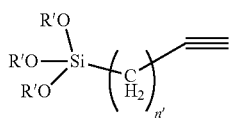   Formula VI'

   Formula XXXIII' where: V' is —P(O)(OH)$_2$ or —Si(T')$_2$W'; W' is -T', —SH, or —NH$_2$ and is the moiety configured to form a covalent bond with the at least one inner surface; T' is independently OH, OC$_{1-6}$ alkyl, or halo; R' is C$_{1-6}$ alkyl; L'$_{fm}$ is a linker including 1 to 200 non-hydrogen atoms selected from any combination of silicon, carbon, nitrogen, oxygen, sulfur and phosphorus atoms, and further includes 0 or 1 coupling groups CG; R'$_x$ is a reactive moiety; n is an integer of 3 to 21, and L'$_{sm}$ is a linker including 1 to 200 non-hydrogen atoms selected from any combination of silicon, carbon, nitrogen, oxygen, sulfur and phosphorus atoms and further includes 0, 1, 2, or 3 coupling groups CG.

86. The method of embodiment 85, where W' is OC$_{1-6}$ alkyl or halo.

87. The method of embodiment 85 or 86, where n' is 7 to 21.

88. The method of any one of embodiments 85 to 87, where T' is OC$_{1-3}$ alkyl or halo and/or R' is C$_{1-3}$ alkyl.

89. The method of any one of embodiments 85 to 88, where the reactive moiety R'$_x$ is alkyne, azide, amine, carboxylic acid, biotin, or streptavidin.

90. The method of any one of embodiments 85 to 88, where the reactive moiety R'$_x$ is alkyne, azide, amine, carboxylic acid, biotin, streptavidin, olefin, trans cyclooctene, s-tetrazine, thiol, maleimide, halide, cyano, isocyanate, epoxide, hydroxyamine, masked hydroxyl, or sulfonyl fluoride.

91. The method of any one of embodiments 85 to 90, where the second modifying reagent may have a structure of Formula I', Formula III', or Formula XXXII', and where the surface modifying ligand of the second modifying reagent may have a structure of Formula X or Formula XI:

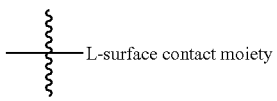   Formula X

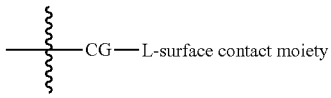   Formula XI where: CG is a coupling group; L is a linker including a bond or 1 to 200 non-hydrogen atoms selected from any combination of silicon, carbon, nitrogen, oxygen, sulfur and phosphorus atoms; the sum of $L_{sm}$ and L is 1 to 200 non-hydrogen atoms, not including atoms of the CG if present; and the surface contact moiety is a moiety configured to support cell growth, viability, portability, or any combination thereof in the microfluidic device.

92. The method of embodiment 91, where the surface contact moiety of the second modifying reagent may include one or more of an alkyl, fluoroalkyl, monosaccharide, polysaccharide; alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety.

93. The method of embodiment 91, where the surface contact moiety of the first modifying reagent may include a polyethylene glycol, a dextran moiety, a proteinaceous moiety, a poly carboxylic acid, or a poly lysine moiety.

94. The method of embodiment 82 or 91, where the surface contact moiety of the first modifying regent and/or the second modifying reagent may support expansion of adherent cells and/or permit export of adherent cells cultured thereupon.

95. The method of embodiment 82 or 91, where the surface contact moiety of the first modifying reagent and/or the second modifying reagent may inhibit motile cells from entering a selected region within the microfluidic device.

96. The method of any one of embodiments 76 to 95, where the first modifying reagent may have a structure of Formula I, Formula III, or Formula XXXII, and where the second modifying reagent may have a structure of Formula IV', Formula VI', or Formula XXXIII'.

97. The method of any one of embodiments 76 to 95, where the first modifying reagent may have a structure of Formula IV, Formula VI, or Formula XXXIII, and where the second modifying reagent may have a structure of Formula I', Formula III', or Formula XXXII'.

98. The method of any one of embodiments 74 to 95 further including contacting the at least one covalently modified surface with a secondary functionalizing reagent of Formula XXXIV

  Formula XXXIV; and reacting the secondary functionalizing reagent with reactive moieties on the first or second covalently bound surface modifications of the at least one covalently modified surface to form a further modified surface, where: RP is a reaction pair moiety for reacting with the reactive moiety of Formula XXXIII, Formula XXXIII', Formula IV, Formula IV', Formula VI, or Formula VI'; $R_{x2}$ is a reactive moiety selected to not react with the reactive moiety of Formula XXXIII, Formula XXXIII', Formula IV, Formula IV', Formula VI, or Formula VI'; and $L_{fm}$ is a linker including 1 to 200 non-hydrogen atoms selected from any combination of silicon, carbon, nitrogen, oxygen, sulfur and phosphorus atoms, and further includes 0 or 1 coupling groups CG.

99. The method of embodiment 98, wherein contacting the at least one covalently modified surface with the secondary functionalizing reagent of Formula XXXIV comprises contacting the at least one covalently modified surface with a solution comprising the secondary functionalizing reagent.

100. The method of any one of embodiments 76 to 99, further including contacting the at least one covalently modified surface with a surface modifying reagent, and reacting the surface modifying reagent with reactive moieties on the at least one covalently modified surface or the further modified surface.

101. The method of embodiment 100, where the surface modifying reagent may have a structure of Formula XII:

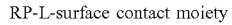  Formula XII where: RP is a reaction pair moiety; the surface contact moiety is a moiety configured to support cell growth, viability, portability, or any combination; and L is a linker including a bond or 1 to 200 non-hydrogen atoms selected from any combination of silicon, carbon, nitrogen, oxygen, sulfur and phosphorus atoms, and includes 0 or 1 coupling groups CG.

102. The method of any one of embodiments 63 to 101, where forming the at least one covalently modified surface may be performed after assembly of the microfluidic device.

103. The method of any one of embodiments 63 to 101, where forming the at least one covalently modified surface may be performed before assembly of the microfluidic device.

104. The method of any one of embodiments 63 to 101, further including: forming a first modified surface of one of the base or the cover before assembly of the microfluidic device; assembling the microfluidic device, where assembling includes assembling the first covalently modified surface of one of the base or the cover with the microfluidic circuit material and the unmodified one of the cover or base; and forming a second modified surface on an unmodified surface of the assembled microfluidic device.

105. The method of any one of embodiments 63 to 104, where the first nucleophilic moieties may be hydroxide, amino or thiol, and/or where the second nucleophilic moiety is hydroxide, amino or thiol.

106. The method of any one of embodiments 63 to 104, where an inner surface of the base and/or cover may be a metal, metal oxide, glass, polymer, or any combination thereof.

107. The method of any one of embodiments 63 to 106, where the microfluidic circuit material may be a polymer.

108. The method of embodiment 107, where the microfluidic circuit material may be polydimethoxysilane (PDMS) or photopatternable silicone (PPS).

109. The method of any one of embodiments 63 to 108, where contacting includes contacting the at least one inner surface with a liquid solution containing the first modifying reagent and/or the second modifying reagent.

110. The method of any one of embodiments 63 to 109, where contacting includes contacting the at least one inner surface with a vapor phase containing the first modifying reagent and/or the second modifying reagent.

111. The method of embodiment 110, where contacting may include contacting the at least one inner surface with the first and/or second modifying reagent in the vapor phase in the presence of a controlled amount of water vapor.

112. The method of embodiment 111, where magnesium sulfate heptahydrate may provide the controlled amount of water vapor.

113. The method of any one of embodiments 110 to 112, where contacting may include contacting the at least one inner surface with the first and/or second modifying reagent in the vapor phase, in an environment under reduced pressure relative to atmospheric pressure.

114. The method of any one of embodiments 63 to 113, where each of the at least one inner surface is pre-treated to introduce an oxide moiety.

115. The method of any one of embodiments 76 to 101, where n is 9, 14, or 16.

116. The method of any one of embodiments 76 to 101, where n is 9.

117. The method of any one of embodiments 85 to 101, where n' equals 9, 11, 14, 16, 18, or n+2.

118. The method of any one of embodiments 98 to 101, where reacting the at least one covalently modified surface with a surface modifying reagent or a secondary functionalizing reagent is performed by contacting the at least one covalently modified with a solution including the surface modifying reagent or the secondary functionalizing reagent.

119. The method of embodiment 118, where the solution including the surface modifying reagent or the functionalizing reagent may further include a Cu(I) salt.

120. The method of embodiment 118, where reacting the at least one covalently modified surface with the surface modifying reagent or the functionalizing reagent may be performed in the absence of copper.

121. The method of any one of embodiments 63 to 120, where forming the at least one covalently modified surface may include forming a monolayer including first covalently bound surface modifications and/or second covalently bound surface modifications.

122. The method of any one of embodiments 63 to 121, where forming the at least one covalently modified surface may include covalently binding more than one kind of proteinaceous moiety to the at least one covalently modified surface.

123. The method of any one of embodiments 63 to 122, where the cover of the microfluidic device may be an integral part of the microfluidic circuit material.

124. The method of any one of embodiments 63 to 123, where the cover or the base of the microfluidic device may include a DEP configuration.

125. The method of embodiment 124, where the DEP configuration may be optically actuated.

126. A method of forming different covalently modified surfaces in a regioselective manner within a microfluidic device, where the microfluidic device comprises an enclosure having a base, a cover, and a microfluidic circuit material defining a microfluidic circuit therein, where the microfluidic circuit comprises a flow region and a sequestration pen, and where the sequestration pen comprises an isolation region and a connection region, the connection region comprising a proximal opening to the flow region and fluidically connecting the isolation region to the flow region, the method comprising: flowing a first modifying reagent through the flow region under conditions such that the first modifying reagent does not enter the isolation region of the sequestration pen; reacting the first modifying reagent with nucleophilic moieties on at least one surface of the flow region, thereby forming a first modified surface within the flow region, where the first modified surface does not extend into the isolation region of the sequestration pen; flowing a second modifying reagent through the flow region under conditions such that the second modifying reagent enters into the isolation region of the sequestration pen; and reacting the second modifying reagent with nucleophilic moieties on at least one surface of the isolation region of the sequestration pen, thereby forming a second modified surface within the isolation region of the sequestration pen, where the first modifying reagent does not have the same structure as the second modifying reagent.

127. The method of embodiment 126, where the conditions for flowing the first modifying reagent through the flow region comprise applying a negative pressure to the flow region.

128. The method of embodiment 127, where flowing the first modifying reagent comprises flowing a solution that comprises the first modifying reagent through the flow region at a rate of about 10 mm/sec or higher (e.g., at least 1 mm/sec; at least 5 mm/sec; at least 10 mm/sec; at least 20 mm/sec; at least 40 mm/sec; at least 50 mm/sec; or any range defined by two of the foregoing values, for example, about 1 mm/sec to about 50 mm/sec, or about 10 mm/sec to about 20 mm/sec).

129. The method of embodiment 126, where the conditions for flowing the first modifying reagent through the flow region comprise applying a positive pressure to the flow region.

130. The method of embodiment 129, where flowing the first modifying reagent comprises flowing a solution that comprises the first modifying reagent through the flow region at a rate of about 2 mm/sec or less (e.g., less than about 1.5 mm/sec; less than about 1.0 mm/sec; less than about 0.5 mm/sec; or any range defined by two of the foregoing values, for example, about 0.5 mm/sec to about 2 mm/sec, or about 1 mm/sec to about 1.5 mm/sec).

131. The method of embodiment 129 or 130, where flowing the first modifying reagent comprises flowing a solution that comprises the first modifying reagent through the flow region, and where the solution comprises a surfactant (e.g., a non-ionic surfactant, such as a Brij surfactant (e.g., Brij L4); the surfactant can have a hydrophile-lipophile balance (HLB) of about 8 to about 12 (e.g., about 8 to about 10, or about 9).

132. The method of any one of embodiments 126 to 131, where the second modifying reagent does not substantially react with moieties on the surfaces of the flow region.

133. The method of any one of embodiments 126 to 132, where: the first modifying reagent comprises a first connecting moiety and a first modifying moiety, the first modifying moiety comprising a first surface contact moiety or a first reactive moiety; and the second modifying reagent comprises a second connecting moiety and a second modifying moiety, the second modifying moiety comprising a second surface contact moiety or a second reactive moiety, where the first connecting moiety is different than the second connecting moiety and/or the first modifying moiety is different from the second modifying moiety.

134. The method of any one of embodiments 126 to 133, wherein the first modifying reagent has a structure of one of the following formulae:

Formula I

Formula III

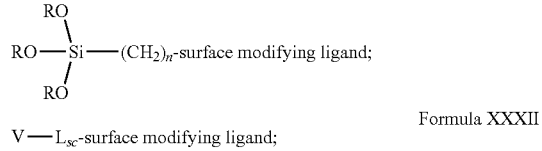

Formula XXXII

Formula IV

Formula VI

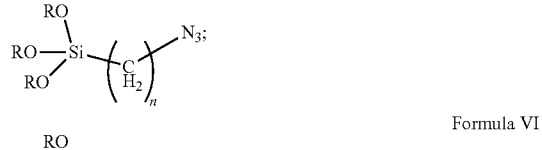

Formula XXXIII

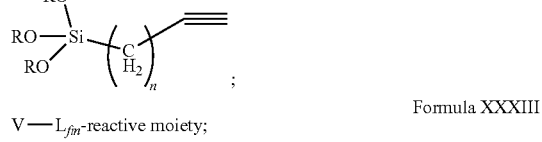

where: V is —P(O)(OH)$_2$ or —Si(T)$_2$W; W is -T, —SH, or —NH$_2$ and is the moiety configured to form a covalent bond with the at least one surface of the flow region; T is independently OH, OC$_{1-6}$ alkyl, or halo; R is C$_{1-6}$ alkyl; L$_{fm}$ is a linker comprising 1 to 200 non-hydrogen atoms selected from any combination of silicon, carbon, nitrogen, oxygen, sulfur and phosphorus atoms, and further comprises 0 or 1 coupling groups CG; R$_x$ is a reactive moiety; n is an integer of 3 to 21; and L$_{sm}$ is a linker comprising 1 to 200 non-hydrogen atoms selected from any combination of silicon, carbon, nitrogen, oxygen, sulfur and phosphorus atoms, and further comprises 0, 1, 2, or 3 coupling groups CG.

135. The method of embodiment 134, where W is OC$_{1-6}$ alkyl or halo.

136. The method of embodiment 134 or 135, where n is 7 to 21.

137. The method of any one of embodiments 134 to 136, where T is OC$_{1-3}$ alkyl or halo and/or R is C$_{1-3}$ alkyl.

138. The method of any one of embodiments 134 to 137, where the reactive moiety R$_x$ is alkyne, azide, amine, carboxylic acid, biotin, streptavidin, olefin, trans cyclooctene, s-tetrazine, thiol, maleimide, halide, cyano, isocyanate, epoxide, hydroxyamine, masked hydroxyl, or sulfonyl fluoride.

139. The method of any one of embodiments 134 to 137, where the reactive moiety R$_x$ is alkyne, azide, amine, carboxylic acid, biotin, or streptavidin.

140. The method of any one of embodiments 134 to 139, where the first modifying reagent has a structure of Formula I, Formula III, or Formula XXXII, and wherein the surface modifying ligand of the first modifying reagent has a structure of Formula X or Formula XI:

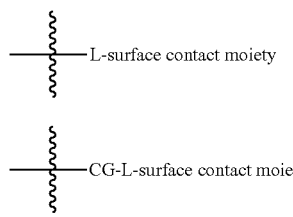

where: CG is a coupling group; L is a linker comprising a bond or 1 to 200 non-hydrogen atoms selected from any combination of silicon, carbon, nitrogen, oxygen, sulfur and phosphorus atoms; the sum of $L_{sm}$ and L is 1 to 200 non-hydrogen atoms, not including atoms of the CG if present; and the surface contact moiety is a moiety configured to support cell growth, viability, portability, or any combination thereof in the microfluidic device.

141. The method of embodiment 140, where the surface contact moiety comprises one or more of an alkyl, fluoroalkyl, monosaccharide, polysaccharide; alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety.

142. The method of embodiment 140, where the surface contact moiety comprises a polyethylene glycol, a dextran moiety, a proteinaceous moiety, a poly carboxylic acid, or a poly lysine moiety.

143. The method of any one of embodiments 126 to 142, where the second modifying reagent has a structure of one of the following formulae:

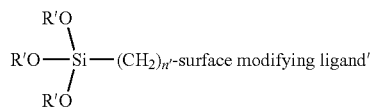

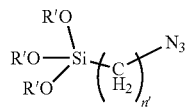

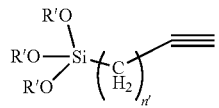

V'-L'$_{fm}$-R'$_x$                Formula XXXIII' where: V' is —P(O)(OH)$_2$ or —Si(T')$_2$W'; W' is -T', —SH, or —NH$_2$ and is the moiety configured to form a covalent bond with the at least one inner surface; T' is independently OH, OC$_{1-6}$ alkyl, or halo; R' is C$_{1-6}$ alkyl; L'$_{fm}$ is a linker comprising 1 to 200 non-hydrogen atoms selected from any combination of silicon, carbon, nitrogen, oxygen, sulfur and phosphorus atoms, and further comprises 0 or 1 coupling groups CG; R'$_x$ is a reactive moiety; n is an integer of 3 to 21, and L'$_{sm}$ is a linker comprising 1 to 200 non-hydrogen atoms selected from any combination of silicon, carbon, nitrogen, oxygen, sulfur and phosphorus atoms and further comprises 0, 1, 2, or 3 coupling groups CG.

144. The method of embodiment 143, where W' is OC$_{1-6}$ alkyl or halo.

145. The method of embodiment 143 or 144, where n' is 7 to 21.

146. The method of any one of embodiments 143 to 145, where T' is OC$_{1-3}$ alkyl or halo and/or R' is C$_{1-3}$ alkyl.

147. The method of any one of embodiments 143 to 146, where the reactive moiety R'$_x$ is alkyne, azide, amine, carboxylic acid, biotin, or streptavidin.

148. The method of any one of embodiments 143 to 147, where the reactive moiety R'$_x$ is alkyne, azide, amine, carboxylic acid, biotin, streptavidin, olefin, trans cyclooctene, s-tetrazine, thiol, maleimide, halide, cyano, isocyanate, epoxide, hydroxyamine, masked hydroxyl, or sulfonyl fluoride.

149. The method of any one of embodiments 143 to 147, where the second modifying reagent has a structure of Formula I', Formula III', or Formula XXXII', and where the surface modifying ligand' of the second modifying reagent has a structure of Formula X or Formula XI:

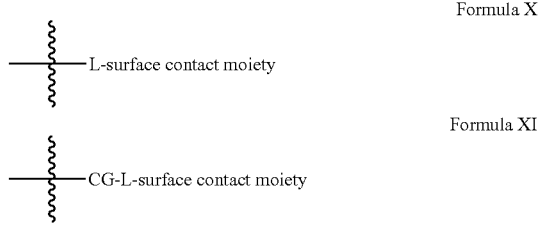

where: CG is a coupling group; L is a linker comprising a bond or 1 to 200 non-hydrogen atoms selected from any combination of silicon, carbon, nitrogen, oxygen, sulfur and phosphorus atoms; the sum of $L_{sm}$ and L is 1 to 200 non-hydrogen atoms, not including atoms of the CG if present; and the surface contact moiety is a moiety configured to support cell growth, viability, portability, or any combination thereof in the microfluidic device.

150. The method of embodiment 149, where the surface contact moiety of the second modifying reagent comprises one or more of an alkyl, fluoroalkyl, monosaccharide, polysaccharide; alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety.

151. The method of embodiment 149, where the surface contact moiety of the second modifying reagent comprises a polyethylene glycol, a dextran moiety, a proteinaceous moiety, a poly carboxylic acid, or a poly lysine moiety.

152. The method of any one of embodiments 134 to 151, where the surface contact moiety of the second modifying reagent supports expansion of adherent cells and/or permits export of adherent cells cultured thereupon.

153. The method of any one of embodiments 134 to 151, where the surface contact moiety of the first modifying reagent inhibits or substantially prevents motile cells from entering the flow region of the microfluidic device.

154. The method of any one of embodiments 143 to 153, where the first modifying reagent has a structure of Formula I, Formula III, or Formula XXXII, and where the second modifying reagent has a structure of Formula IV', Formula VI', or Formula XXXIII'.

155. The method of any one of embodiments 143 to 153, where the first modifying reagent has a structure of Formula IV, Formula VI, or Formula XXXIII, and where the second modifying reagent has a structure of Formula I', Formula III', or Formula XXXII'.

156. The method of any one of embodiments 126 to 154, where the second modified surface within the isolation region of the sequestration pen comprises second covalently bound surface modifications each having a structure of Formula XXX', Formula V', or Formula VII'.

157. The method of embodiment 156 further comprising contacting the second modified surface with a surface modifying reagent of Formula XII $$\text{RP-L-surface contact moiety} \quad \text{Formula XII;}$$

and reacting the second covalently bound surface modifications of the second modified surface with the surface modifying reagent to form a further modified surface within the isolation region of the sequestration pen, where: RP is a reaction pair moiety; the surface contact moiety is a moiety configured to support cell growth, viability, portability, or any combination thereof; and L is a linker, wherein L comprises a bond or 1 to 200 non-hydrogen atoms selected from any combination of silicon, carbon, nitrogen, oxygen, sulfur and phosphorus atoms, and further comprises 0 or 1 coupling groups CG.

158. The method of embodiment 157, where contacting the second modified surface with the surface modifying reagent of Formula XII comprises: flowing a solution comprising the surface modifying reagent into the flow region; and allowing the surface modifying reagent to diffuse into the isolation region of the sequestration pen and contact the second modified surface.

159. The method of any one of embodiments 156 to 158, where the first modified surface in the flow region comprises first covalently bound surface modifications each having a structure of Formula XXXI, Formula VIII, or Formula IX.

160. The method of embodiment 156, further comprising contacting the second modified surface with a secondary functionalizing reagent of Formula XXXIV $$\text{RP-}L_{fm}\text{-reactive moiety}_2 \quad \text{Formula XXXIV;}$$

and reacting the secondary functionalizing reagent with reactive moieties on the second covalently bound surface modifications of the second modified surface to form a further modified surface within the isolation region of the sequestration pen, where: RP is a reaction pair moiety for reacting with the reactive moiety of Formula XXX, Formula V, or Formula VII; $R_{x2}$ is a reactive moiety selected to not react with the reactive moiety of the second modified surface; and $L_{fm}$ is a linker comprising 1 to 200 non-hydrogen atoms selected from any combination of silicon, carbon, nitrogen, oxygen, sulfur and phosphorus atoms and further comprises 0 or 1 coupling groups CG.

161. The method of embodiment 160, where contacting the second modified surface with the secondary functionalizing reagent of Formula XXXIV comprises: flowing a solution comprising the secondary functionalizing reagent into the flow region; and allowing the secondary functionalizing reagent to diffuse into the isolation region of the sequestration pen and contact the second modified surface.

162. The method of embodiment 160 or 161, where the second covalently bound surface modifications that reacted with the secondary functionalizing reagent each comprise 1 or 2 CG.

163. The method of any one of embodiments 126 to 162, where the nucleophilic moieties on the surface(s) of the flow region are selected from hydroxide, amino, and thiol; and/or where the nucleophilic moieties on the surface(s) of the sequestration pen are selected from hydroxide, amino, and thiol.

164. The method of any one of embodiments 126 to 163, where the microfluidic circuit comprises a plurality of sequestration pens, each treated to form at least one second modified or further modified surface therein.

165. The method of any one of embodiments 126 to 164, where an inner surface of the base and/or cover is a metal, metal oxide, glass, polymer, or any combination thereof.

166. The method of any one of embodiments 126 to 165, where the microfluidic circuit material is a polymer.

167. The method of embodiment 166, where the microfluidic circuit material is polydimethoxysilane (PDMS) or photopatternable silicone (PPS).

168. The method of any one of embodiments 126 to 167, where the cover of the microfluidic device is an integral part of the microfluidic circuit material.

169. The method of any one of embodiments 126 to 168, where each of the inner surfaces of the base, cover, and microfluidic circuit material is pre-treated to introduce an oxide moiety.

170. The method of any one of embodiments 134 to 162, where n is 9, 14, or 16.

171. The method of any one of embodiments 134 to 162, where n is 9.

172. The method of any one of embodiments 143 to 162, where n' equals 9, 11, 14, 16, 18, or n+2.

173. The method of embodiment 158 or 161, where the solution comprising the surface modifying reagent or the secondary functionalizing reagent further comprises a Cu(I) salt.

174. The method of embodiment 158 or 161, where the solution comprising the surface modifying reagent or the secondary functionalizing reagent is a copper solution.

175. The method of embodiment 156 or 159, where the first covalently bound surface modifications form a monolayer on the at least one surface of the flow region and/or the second covalently bound surface modifications form a monolayer on the at least one surface of the isolation region of the sequestration pen.

176. The method of any one of embodiments 126 to 175, where forming the first modified surface and/or forming the second modified surface comprises introducing more than one kind of proteinaceous moiety.

177. The method of any one of embodiments 126 to 176, where the cover or the base of the microfluidic device comprises a DEP configuration.

178. The method of embodiment 177, where the DEP configuration is optically actuated.

179. The method of any one of embodiments 126 to 178, where forming the first modified surface comprises forming a covalently modified surface on substantially all the inner surfaces of the flow region.

180. The method of any one of embodiments 126 to 179, where forming the second modified surface comprises forming a covalently modified surface on substantially all the inner surfaces of the isolation region of the sequestration pen.

300. A kit including a microfluidic device of any one of embodiments 1 to 62.

301. The kit of embodiment 300, further including a surface modifying reagent having a structure of Formula XII:

RP-L-surface contact moiety  Formula XII:

wherein RP is a reaction pair moiety; surface contact moiety is a moiety configured to support cell growth, viability, portability, or any combination thereof; L is a linker; wherein L may be a bond or 1 to 200 non-hydrogen atoms selected from any combination of silicon, carbon, nitrogen, oxygen, sulfur and phosphorus atoms, and may further include 0 or 1 coupling groups CG.

302. The kit of embodiment 300 or 301, further including a secondary functionalizing reagent having a structure of Formula XXXIV:

RP-$L_{fm}$-$R_{x2}$  Formula XXXIV, where RP is a reaction pair moiety for reacting with the reactive moiety of Formula XXX, Formula V, or Formula VII; $R_{x2}$ is a reactive moiety selected to not react with the reactive moiety of the functionalized surface of Formula XXX, Formula V or Formula VII; and, $L_{fm}$ is a linker comprising 1 to 200 non-hydrogen atoms selected from any combination of silicon, carbon, nitrogen, oxygen, sulfur and phosphorus atoms and may further include 0 or 1 coupling groups CG.

400. A method of synthesizing a compound of Formula IV:

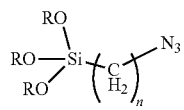

Formula IV including the step of: reacting a compound having a structure of Formula XIII:

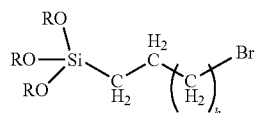

Formula XIII where h is 1 to 19 with azide ion, thereby producing the compound of Formula IV, where n is 3 to 21 and R is H or $C_1$-$C_6$ alkyl.

401. The method of embodiment 400, where a counter ion to the azide ion may be sodium.

402. The method of embodiment 400 or 401, where the reaction may be performed in acetonitrile or DMF.

403. The method of any one of embodiments 400 to 402, where the reaction is performed at ambient temperature.

404. The method of any one of embodiments 400 to 403, where the reaction is performed under an inert atmosphere.

405. A method of synthesizing a compound having a structure of Formula XIII

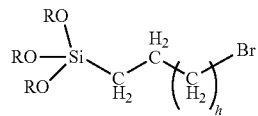

Formula XIII including: reacting a compound having a structure of the following formula:

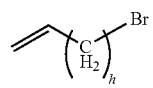

with a compound having a structure of the formula HSi(OR)$_3$, in the presence of a catalyst or an initiator, thereby producing the compound of Formula XIII, where h is an integer of 1 to 19 and each instance of R is independently H or $C_1$ to $C_6$ alkyl.

406. The method of embodiment 405, where the catalyst is a hydrosilylation catalyst.

407. The method of embodiment 406, where the catalyst is platinum(0)-1,3-divinyl-1,1,3,3-tetramethyldisiloxane complex, $H_2PtCl_6$·$6H_2O$/iPrOH, or tris(triphenylphosphine)rhodium(I) chloride.

408. The method of any one of embodiments 405 to 407, where the catalyst is a platinum (0) catalyst.

409. The method of embodiment 408, where the initiator is trialkylborane.

410. The method of any one of embodiments 405 to 409, where the reaction may be performed in a solution of toluene.

411. The method of any one of embodiments 405 to 410, where the reaction may be performed under an inert atmosphere.

412. The method of any one of embodiments 405 to 411, where the reaction may be performed at a temperature in a range of about 60° C. to about 110° C.

413. The method of any one of embodiments 405 to 412, where each instance of R is Me or Et.

414. The method of any one of embodiments 405 to 413, where h may be 7, 12, or 14.

415. The method of any one of embodiments 405 to 414, where each instance of R is Me and h is 7.

416. A compound having a structure of Formula IV:

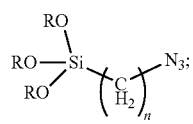

Formula IV where n is an integer of 7 to 21, and R is independently H or $C_1$ to $C_6$ alkyl.

417. The compound of embodiment 416, where R is Me, Et or Pr.

418. The compound of embodiment 416 or 417, where each instance of R may be Me.

419. The compound of any one of embodiments 416 to 418, where n is 9 to 21.

420. The compound of any one of embodiments 416 to 419, where n is 9, 14 or 16.

421. The compound of any one of embodiments 416 to 420, where n is 9 and each instance of R is Me.

422. A compound having a structure of Formula XIII:

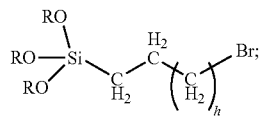

Formula XIII where h is an integer of 5 to 19 and R is selected independently from the group consisting of H and $C_1$-$C_6$ alkyl.

423. The compound of embodiment 422, where n is 9 to 21.

424. The compound of embodiment 422 or 423, where h is 7, 12, or 14.

425. The compound of any one of embodiments 422-424, where h is 14 or 16.

426. The compound of any one of embodiments 422-425, where each instance of R may be Me or Et.

427. A compound having a structure of Formula LI:

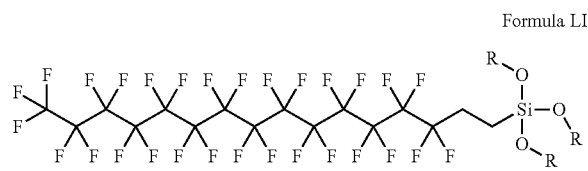

Formula LI wherein R is selected independently from the group consisting of H and $C_1$-$C_6$ alkyl.

428. A compound having a structure of the Formula LII:

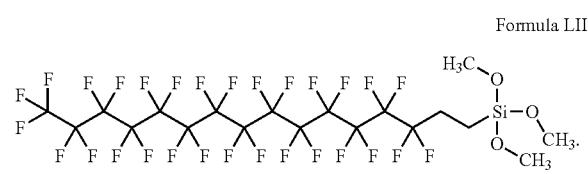 [SMILES: CO[Si](CCC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)(OC)OC]

Formula LII

429. A method of synthesizing a compound of Formula L

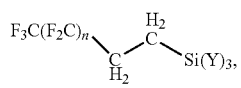

Formula L comprising the step of:
reacting a compound having a structure of the following formula:

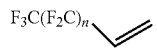

with a compound having the formula $SiH(Y)_3$ in the presence of a catalyst or an initiator, thereby producing the compound of Formula I, wherein n is an integer of 13 to 25; each instance of Y is independently halo, OH, or OR; and R is $C_1$ to $C_6$ alkyl.

430. The method of embodiment 429, where the catalyst is a hydrosilylation catalyst.

431. The method of embodiment 429, where the catalyst is selected from platinum(0)-1,3-divinyl-1,1,3,3-tetramethyldisiloxane complex, $H_2PtCl_6.6H_2O$/iPrOH, and tris(triphenylphosphine)rhodium(I) chloride.

432. The method of any one of embodiments 429 to 431, where the catalyst is a platinum (0) catalyst.

433. The method of embodiment 429, where the initiator is trialkylborane.

434. The method of any one of embodiments 429 to 433, where the step of reacting is performed in a solution of 1, 3-bis-trifluoromethyl benzene.

435. The method of any one of embodiments 429 to 434, where the step of reacting is performed under an inert atmosphere.

436. The method of any one of embodiments 429 to 435, where the step of reacting is performed at a temperature in a range of about 60° C. to about 110° C.

437. The method of any one of embodiments 429 to 436, where each instance of Y is Cl, OMe, or OEt.

438. The method of any one of embodiments 429 to 437, where n is 13, 15, 16, or 19.

439. A method of synthesizing a compound having a structure of Formula LII,

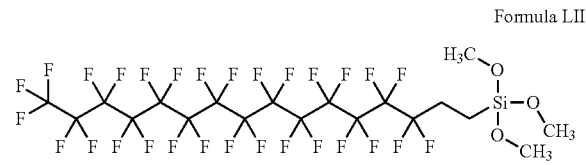 [SMILES: CO[Si](CCC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F)(OC)OC]

Formula LII comprising the step of:
reacting 3, 3, 4, 4, 5, 5, 6, 6, 7, 7, 8, 8, 9, 9, 10, 10, 11, 11, 12, 12, 13, 13, 14, 14, 15, 15, 16, 16, 16-nonacosafluorohexadec-1-ene with trimethoxysilane in the presence of a catalyst or initiator; thereby producing the molecule of Formula LII (trimethoxy (3, 3, 4, 4, 5, 5, 6, 6, 7, 7, 8, 8, 9, 9, 10, 10, 11, 11, 12, 12, 13, 13, 14, 14, 15, 15, 16, 16, 16-nonacosafluorohexadecyl)-silane).

440. The method of embodiment 439, where the catalyst is a hydrosilylation catalyst.

441. The method of embodiment 439, where the catalyst is selected from platinum(0)-1,3-divinyl-1,1,3,3-tetramethyldisiloxane complex, $H_2PtCl_6.6H_2O$/iPrOH, and tris(triphenylphosphine)rhodium(I) chloride.

442. The method of any one of embodiments 439 to 441, where the catalyst is a platinum (0) catalyst.

443. The method of embodiment 439, where the initiator is trialkylborane.

444. The method of any one of embodiments 439 to 443, where the step of reacting is performed in a solution of 1, 3-bis trifluoromethyl benzene.

445. The method of any one of embodiments 439 to 444, where the step of reacting is performed under an inert atmosphere.

446. The method of any one of embodiments 439 to 445, where the step of reacting is performed at a temperature in a range of about 60° C. to about 110° C.

What is claimed:
1. A microfluidic device comprising:
an enclosure comprising a base, a cover, and microfluidic circuit material defining a fluidic circuit therein, wherein the fluidic circuit comprises a flow region and sequestration pens, wherein at least one surface of the flow region is modified with a plurality of first covalently bound surface modifications, each comprising:

a first linking group, and a first moiety, wherein the first moiety is a first surface contact moiety covalently linked to the first linking group, and the first surface contact moiety is configured to inhibit self-propelled movement of cells from one sequestration pen to another sequestration pen or;

wherein at least one surface of the sequestration pens is modified with a plurality of second covalently bound surface modifications, each comprising a second linking group, and a second moiety, wherein the second moiety is a reactive moiety, the first moiety is different from the second moiety.

2. The microfluidic device of claim 1, wherein the first moiety and the second moiety are each covalently bound to the surface via a linking group LG independently selected from —W—Si(OZ)$_2$O— and —OP(O)$_2$O—, wherein W is O, S, or N, and wherein Z is a bond to a silicon atom in an adjacent linking group LG or is a bond to the surface.

3. The microfluidic device of claim 1, wherein the first surface contact moiety comprises one or more of an alkyl, fluoroalkyl, monosaccharide, polysaccharide, alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety; and/or wherein the second surface contact moiety comprises one or more of an alkyl, fluoroalkyl, monosaccharide, polysaccharide, alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety.

4. The microfluidic device of claim 1, wherein the first surface contact moiety comprises a polyethylene glycol moiety, a dextran moiety, a proteinaceous moiety, a poly carboxylic acid, a polylysine moiety, or any combination thereof; and/or wherein the second surface contact moiety comprises a polyethylene glycol moiety, a dextran moiety, a proteinaceous moiety, a poly carboxylic acid, a polylysine moiety, or any combination thereof.

5. The microfluidic device of claim 1, wherein the reactive moiety is an alkyne moiety, an azide moiety, a carboxylic acid moiety, an amine moiety, an olefinic moiety, a tetrazinyl moiety, a trans-cyclooctenyl moiety, a thiol moiety, a maleimide moiety, a biotin moiety, a streptavidin moiety, a halide moiety, a cyano moiety, isocyanate moiety, an epoxide moiety, a hydroxyamine moiety, or a sulfonyl fluoride moiety.

6. The microfluidic device of claim 1, wherein each first covalently bound surface modification comprises a linker, wherein the linker comprises 1 to 200 non-hydrogen atoms selected from any combination of silicon, carbon, nitrogen, oxygen, sulfur and phosphorus atoms; and/or wherein each second covalently bound surface modification comprises a linker, wherein the linker comprises 1 to 200 non-hydrogen atoms selected from any combination of silicon, carbon, nitrogen, oxygen, sulfur and phosphorus atoms.

7. The microfluidic device of claim 6, wherein the linker of the first covalently bound surface modifications further comprises one or two coupling group CG moieties; and/or wherein the linker of the second covalently bound surface modifications further comprises one or two coupling group CG moieties.

8. The microfluidic device of claim 1, wherein the first covalently bound surface modifications have a structure selected from Formula XXXI, Formula VIII, and Formula IX:

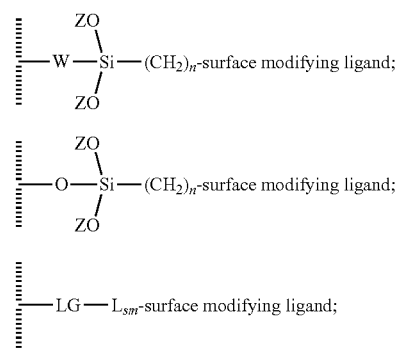

wherein:

LG is —W—Si(OZ)$_2$O— or —OP(O)$_2$O—;

W is O, S, or N;

Z is a bond to an adjacent silicon atom or is a bond to the surface;

n is an integer of 3 to 21;

L$_{sm}$ is a linker comprising 1 to 200 non-hydrogen atoms selected from any combination of silicon, carbon, nitrogen, oxygen, sulfur and phosphorus atoms and further comprises 0, 1, 2, or 3 coupling groups CG; and ⦀ is the surface.

9. The microfluidic device of claim 8, wherein LG is —W—Si(OZ)$_2$O—, and wherein W is O.

10. The microfluidic device of claim 8, wherein n is 7 to 21.

11. The microfluidic device of claim 8, wherein the second covalently bound surface modifications have a structure selected from Formula XXX', Formula V', Formula VII':

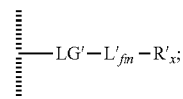

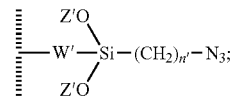

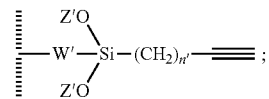

wherein:

LG' is —W—Si(OZ')$_2$O— or —OP(O)$_2$O—;

L'$_{fm}$ is a linker comprising 1 to 200 non-hydrogen atoms selected from any combination of silicon, carbon, nitrogen, oxygen, sulfur and phosphorus atoms and further comprises 0 or 1 coupling groups CG;

R'$_x$ is a reactive moiety;

W' is O, S, or N;

Z' is a bond to an adjacent silicon atom or is a bond to the surface;

n' is an integer of 3 to 21;

L'$_{sm}$ is a linker comprising 1 to 200 non-hydrogen atoms selected from any combination of silicon, carbon, nitrogen, oxygen, sulfur and phosphorus atoms and further comprises 0, 1, 2, or 3 coupling groups CG; and ≡ is the surface.

12. The microfluidic device of claim 11, wherein LG' is —W—Si(OZ')$_2$O—, and wherein W' is O.

13. The microfluidic device of claim 11, wherein n' is 7 to 21.

14. The microfluidic device of claim 11, wherein the reactive moiety R'$_x$ is alkyne, azide, amine, carboxylic acid, biotin, or streptavidin.

15. The microfluidic device of claim 1, wherein the first moiety is different from the second moiety.

16. The microfluidic device of claim 1, wherein the sequestration pen comprises an isolation region and a connection region, wherein the connection region comprises a proximal opening to the flow region and fluidically connects the isolation region to the flow region.

17. The microfluidic device of claim 1, wherein the second covalently bound surface modifications comprises a surface contact moiety configured to anchor adherent cells.

18. The microfluidic device of claim 1, wherein the first covalently bound surface modifications comprises a surface contact moiety configured to inhibit migration of motile cells out of the sequestration pen.

19. The microfluidic device of claim 16, wherein the fluidic circuit further comprises a plurality of sequestration pens each having at least one inner surface modified with the first and/or second covalently bound surface modifications.

20. The microfluidic device of claim 1, wherein the first covalently bound surface modifications and/or the second covalently bound surface modifications form a monolayer.

21. The microfluidic device of claim 1, wherein the inner surface of the base and/or the inner surface of the cover of the enclosure comprises glass, silicon, silicon oxide, hafnium oxide, indium tantalum oxide, or aluminum oxide.

22. The microfluidic device of claim 1, wherein the inner surface of the microfluidic circuit material comprises polydimethylsiloxane (PDMS) or photopatternable silicone (PPS).

23. The microfluidic device of claim 1, wherein substantially all of the inner surfaces of the enclosure are covalently modified.

24. The microfluidic device of claim 1, wherein the first or the second covalently bound surface modification has a structure of one of the following formulae:

Formula XV

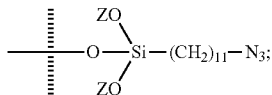

Formula XVI

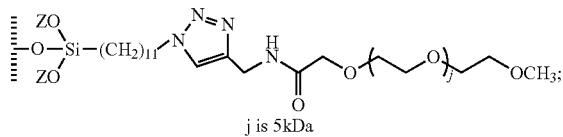

j is 5kDa

Formula XVII

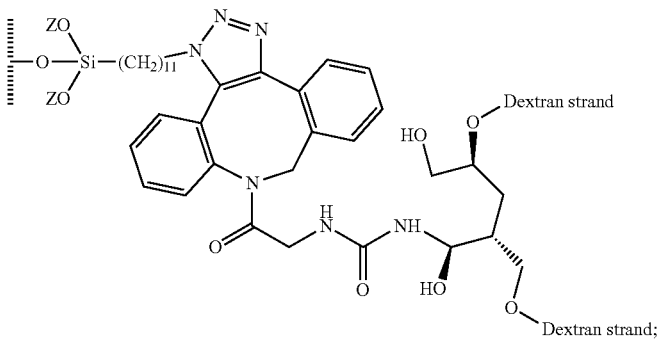

Formula XVIII

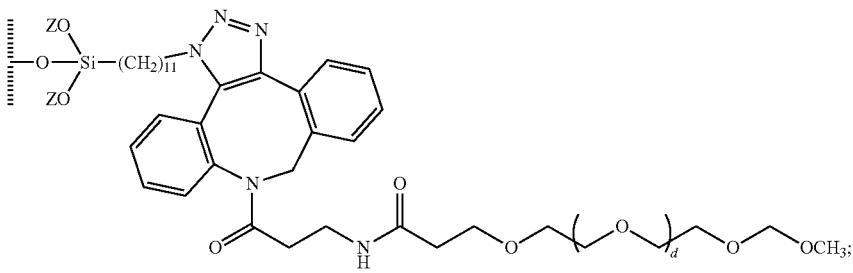

d = 5kDa

Formula XIX
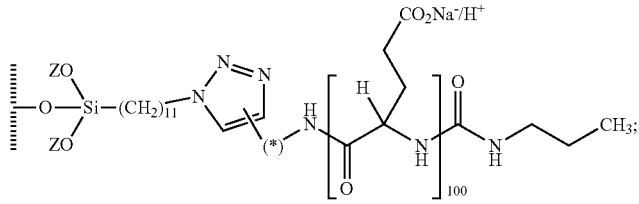
Formula XX
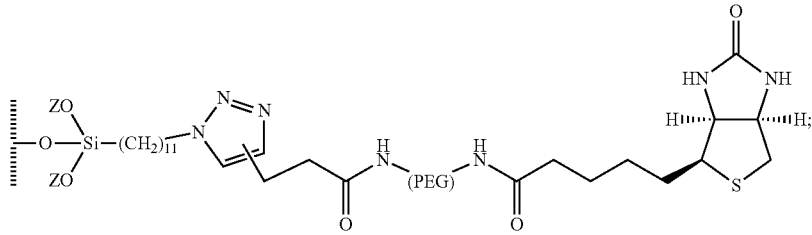
Formula XXI
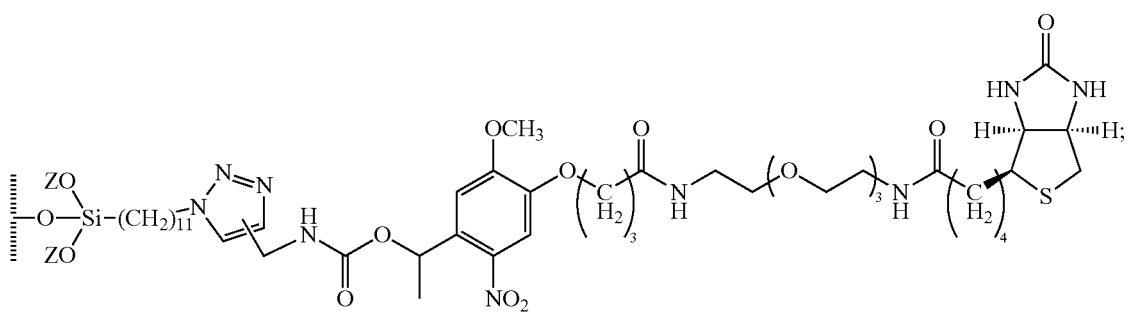
Formula XXII
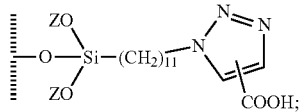
Formula XXIII
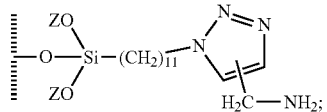
Formula XXIV
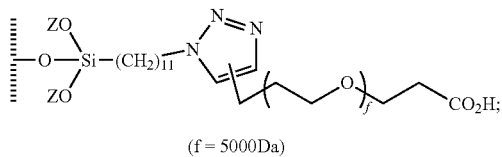
(f = 5000Da)
Formula XXV
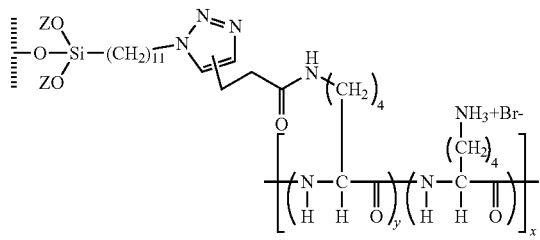
x = 100
y = 20%

-continued
Formula XXVI
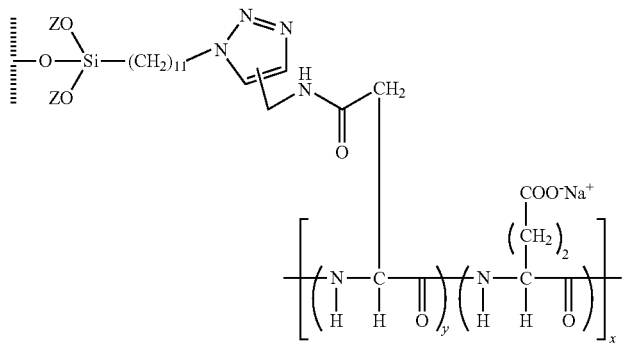
x = 100
y = 20%
Formula XXVII
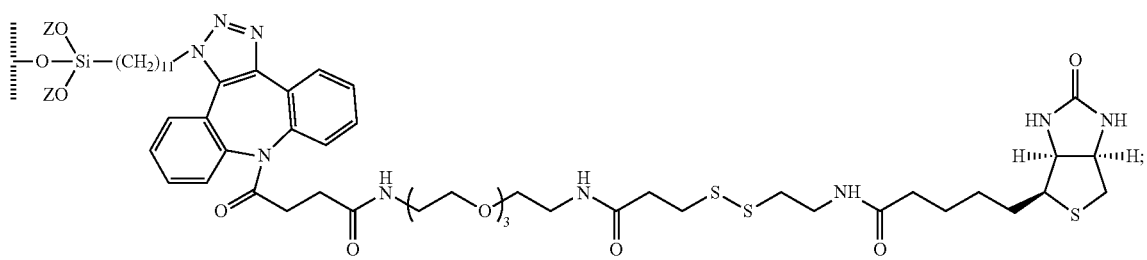
Formula XXVIII
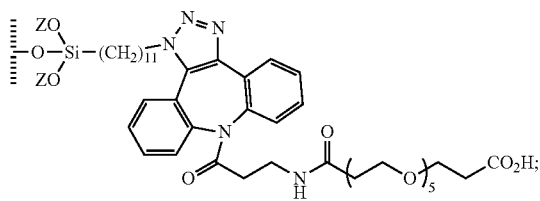
Formula XXIX
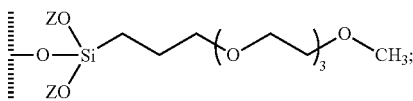
Formula XXXVI
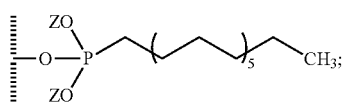
Formula XXXVII
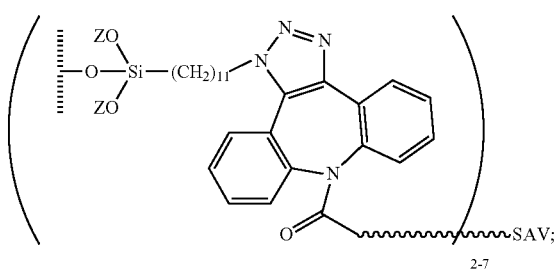
Formula XXVIII
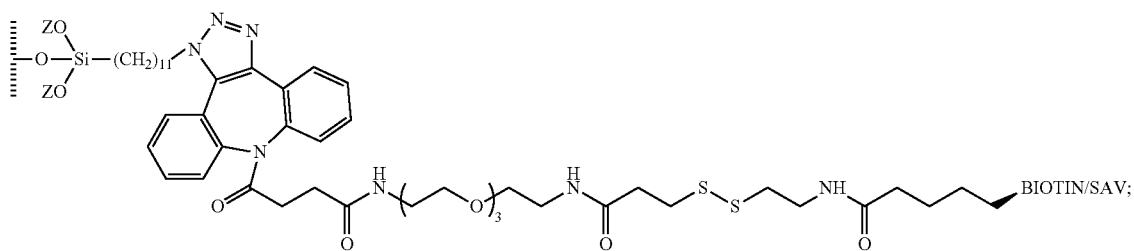

Formula XXIX

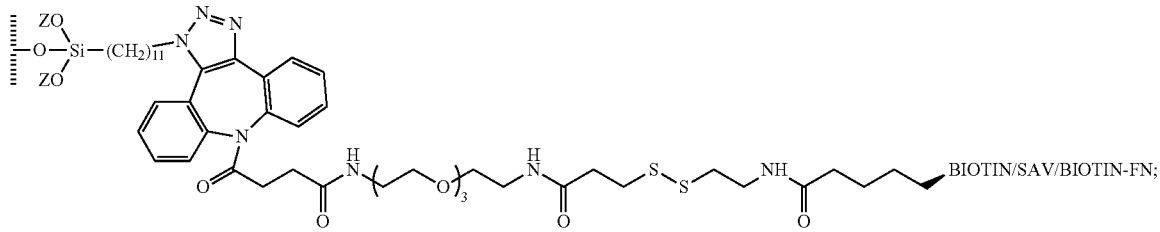

Formula XL

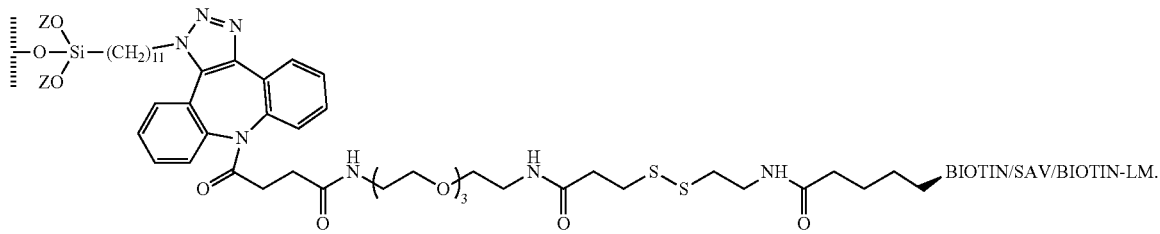

25. A method of forming different covalently modified surfaces in a regioselective manner within a microfluidic device, wherein the microfluidic device comprises an enclosure having a base, a cover, and a microfluidic circuit material defining a microfluidic circuit therein, wherein the microfluidic circuit comprises a flow region and a sequestration pen, and wherein the sequestration pen comprises an isolation region and a connection region, the connection region comprising a proximal opening to the flow region and fluidically connecting the isolation region to the flow region, the method comprising:
flowing a first modifying reagent through the flow region under conditions such that the first modifying reagent does not enter the isolation region of the sequestration pen;
reacting the first modifying reagent with reactive moieties on at least one surface of the flow region, thereby forming a first modified surface within the flow region, wherein the first modified surface does not extend into the isolation region of the sequestration pen;
flowing a second modifying reagent through the flow region under conditions such that the second modifying reagent enters into the isolation region of the sequestration pen; and
reacting the second modifying reagent with reactive c moieties on at least one surface of the isolation region of the sequestration pen, thereby forming a second modified surface within the isolation region of the sequestration pen,
wherein the first modifying reagent does not have the same structure as the second modifying reagent.

26. The method of claim 25, wherein the conditions for flowing the first modifying reagent through the flow region comprise applying a negative pressure to the flow region.

27. The method of claim 26, wherein flowing the first modifying reagent comprises flowing a solution that comprises the first modifying reagent through the flow region at a rate of about 10 mm/sec or higher.

28. The method of claim 25, wherein the conditions for flowing the first modifying reagent through the flow region comprise applying a positive pressure to the flow region.

29. The method of claim 28, wherein flowing the first modifying reagent comprises flowing a solution that comprises the first modifying reagent through the flow region at a rate of about 2 mm/sec or less.

30. The method of claim 25, wherein the second modifying reagent does not substantially react with moieties on the surfaces of the flow region.

31. The method of claim 25, wherein the first modifying reagent has a structure of Formula XII:

RP-L-surface contact moiety            Formula XII wherein RP is a reaction pair moiety configured to react with the reactive moieties on at least
one surface of the flow region, comprising an azide, an alkyne, a biotin or a streptavidin moiety; and
L is a linker comprising a bond or from 1 to 200 non-hydrogen atoms selected from silicon, carbon, nitrogen, oxygen, sulfur and phosphorus atoms.

32. The method of claim 31, wherein the surface contact moiety comprises one or more of an alkyl, fluoroalkyl, monosaccharide, polysaccharide, alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety.

33. The method of claim 31, wherein the surface contact moiety comprises a polyethylene glycol, a dextran moiety, a proteinaceous moiety, a poly carboxylic acid, or a poly lysine moiety.

34. The method of claim 25, wherein the second modifying reagent has a structure of Formula XII:

RP-L-surface contact moiety            Formula XII wherein RP is a reaction pair moiety comprising an azide, an alkyne, a biotin or a streptavidin moiety configured to react with the reactive moieties on the at least one surface of the isolation region; and
L is a linker comprising a bond or from 1 to 200 non-hydrogen atoms selected from silicon, carbon, nitrogen, oxygen, sulfur and phosphorus atoms.

35. The method of claim 34, wherein the surface contact moiety comprises one or more of an alkyl, fluoroalkyl, monosaccharide, polysaccharide, alcohol, polyalcohol, alkylene ether, polyelectrolytes, amino, carboxylic acid, phosphonic acid, sulfonate anion, carboxybetaines, sulfobetaine, sulfamic acid, amino acid moiety, or cleavable moiety.

36. The method of claim 34, wherein the surface contact moiety comprises a polyethylene glycol, a dextran moiety, a proteinaceous moiety, a poly carboxylic acid, or a poly lysine moiety.

37. The method of claim 25, wherein the conditions such that the second modifying reagent enters into the isolation region of the sequestration pen comprises priming the microfluidic device with carbon dioxide prior to flowing a second modifying reagent through the flow region but after reacting the first modifying reagent with nucleophilic moieties on at least one surface of the flow region.

38. The method of claim 25, wherein the reactive moieties of the at least one surface of the flow region and/or the reactive moieties of the at least one surface of the isolation region are nucleophilic moieties.

* * * * *

UNITED STATES PATENT AND TRADEMARK OFFICE
CERTIFICATE OF CORRECTION

| | |
|---|---|
| PATENT NO. | : 11,007,520 B2 |
| APPLICATION NO. | : 16/196649 |
| DATED | : May 18, 2021 |
| INVENTOR(S) | : Randall D. Lowe, Jr. et al. |

It is certified that error appears in the above-identified patent and that said Letters Patent is hereby corrected as shown below:

In the Claims

Claim 11, Column 123, Line 6: after "n′ is an integer of 3 to 21;" and before "and $\equiv$ is the surface.", delete "$L'_{sm}$ is a linker comprising 1 to 200 non-hydrogen atoms selected from any combination of silicon, carbon, nitrogen, oxygen, sulfur and phosphorus atoms and further comprises 0, 1, 2, or 3 coupling groups CG;".

Claim 25, Column 129, Line 49: after "reacting the second modifying reagent with reactive" and before "moieties on at least one", delete "c".

Signed and Sealed this
First Day of August, 2023

Katherine Kelly Vidal
*Director of the United States Patent and Trademark Office*